US010004831B2

(12) United States Patent
Mani et al.

(10) Patent No.: US 10,004,831 B2
(45) Date of Patent: Jun. 26, 2018

(54) FORMULATIONS FOR TAILORED DRUG RELEASE

(71) Applicants: South Dakota Board of Regents, Pierre, SD (US); SANFORD HEALTH, Sioux Falls, SD (US)

(72) Inventors: Gopinath Mani, Pierre, SD (US); Sujan Lamichhane, Pierre, SD (US); Jordan Anderson, Pierre, SD (US); Tyler Remund, Sioux Falls, SD (US); Patrick W. Kelly, Sioux Falls, SD (US)

(73) Assignees: South Dakota Board of Regents, Pierre, SD (US); Sanford Health, Sioux Falls, SD (US)

( * ) Notice: Subject to any disclaimer, the term of this patent is extended or adjusted under 35 U.S.C. 154(b) by 10 days.

(21) Appl. No.: 15/598,544

(22) Filed: May 18, 2017

(65) Prior Publication Data

US 2017/0252489 A1 Sep. 7, 2017

Related U.S. Application Data

(63) Continuation of application No. 14/921,531, filed on Oct. 23, 2015.

(60) Provisional application No. 62/067,847, filed on Oct. 23, 2014, provisional application No. 62/196,707, filed on Jul. 24, 2015.

(51) Int. Cl.
| | |
|---|---|
| *A61L 29/08* | (2006.01) |
| *A61L 29/16* | (2006.01) |
| *A61L 31/10* | (2006.01) |
| *A61M 25/10* | (2013.01) |

(52) U.S. Cl.
CPC ............ *A61L 29/085* (2013.01); *A61L 29/16* (2013.01); *A61L 31/10* (2013.01); *A61L 2300/416* (2013.01); *A61L 2300/608* (2013.01); *A61L 2420/02* (2013.01); *A61L 2420/06* (2013.01); *A61L 2420/08* (2013.01); *A61M 25/10* (2013.01); *A61M 2025/105* (2013.01)

(58) Field of Classification Search
CPC .... A61L 29/085; A61L 29/16; A61L 2420/06; A61L 2420/02; A61L 2420/08; A61L 2300/416; A61L 2300/608; A61L 31/10; A61L 29/145; A61L 31/145; A61L 33/0064; A61L 31/16; A61L 33/068; A61M 2025/105; A61M 25/10; A61M 2025/0046; C08L 71/02
See application file for complete search history.

(56) References Cited

U.S. PATENT DOCUMENTS

| | | | | | |
|---|---|---|---|---|---|
| 4,487,808 | A | * | 12/1984 | Lambert | A61L 29/085 428/423.1 |
| 4,994,047 | A | * | 2/1991 | Walker | A61L 29/06 600/581 |
| 5,041,100 | A | * | 8/1991 | Rowland | A61L 29/085 604/264 |
| 5,084,315 | A | * | 1/1992 | Karimi | A61L 29/085 264/171.27 |
| 5,179,174 | A | * | 1/1993 | Elton | A61L 29/085 428/423.1 |
| 5,416,131 | A | * | 5/1995 | Wolff | A61L 29/085 424/78.24 |
| 5,447,724 | A | * | 9/1995 | Helmus | A61L 27/54 424/423 |
| 5,509,899 | A | * | 4/1996 | Fan | A61L 29/06 604/103.14 |
| 5,529,914 | A | * | 6/1996 | Hubbell | A61K 9/1635 435/182 |
| 5,558,900 | A | * | 9/1996 | Fan | A61L 29/049 427/2.28 |
| 5,993,972 | A | * | 11/1999 | Reich | A61K 8/87 2/161.7 |
| 6,176,849 | B1 | * | 1/2001 | Yang | A61L 29/085 604/265 |
| 6,221,467 | B1 | * | 4/2001 | Nazarova | A61L 29/085 428/213 |
| 6,306,144 | B1 | * | 10/2001 | Sydney | A61F 2/958 604/265 |
| 6,663,662 | B2 | * | 12/2003 | Pacetti | A61F 2/07 623/1.13 |
| 6,790,228 | B2 | * | 9/2004 | Hossainy | A61L 27/306 424/422 |
| 7,279,175 | B2 | * | 10/2007 | Chen | A61K 9/0024 424/423 |
| 8,287,890 | B2 | * | 10/2012 | Elton | A61L 29/085 424/400 |

(Continued)

OTHER PUBLICATIONS

Liu, Xi, et al. "Evaluation of two polymeric blends (EVA/PLA and EVA/PEG) as coating film materials for paclitaxel-eluting stent application." Journal of Materials Science: Materials in Medicine 22.2 (2011): 327-337.*
Yang, Luo, et al. "Ureteral stent technology: Drug-eluting stents and stent coatings." Asian journal of urology 2.4 (2015): 194-201.*
Baba M, Pauwels R, Balzarini J, Arnout J, Desmyter J. Mechanism of inhibitory effect of dextran sulfate and heparin on replication of human immunodeficiency virus in vitro. Proc. Natl. Acad. Sci. USA 1988;85:6132-6136.

(Continued)

*Primary Examiner* — Bethany P Barham
*Assistant Examiner* — Peter Anthopolos
(74) *Attorney, Agent, or Firm* — McDonnell Boehnen Hulbert & Berghoff LLP

(57) ABSTRACT

The present invention provides formulations comprising polymers and therapeutics and methods for their manufacture. The present invention also provides medical devices coated with such formulations and methods for their manufacture. The drug-loaded polymer formulations, solutions, and films tailor the drug release characteristics for medical devices.

14 Claims, 24 Drawing Sheets

(56) References Cited

U.S. PATENT DOCUMENTS

| | | | |
|---|---|---|---|
| 8,469,943 B2* | 6/2013 | Bates | A61F 2/06 604/523 |
| 2004/0087901 A1* | 5/2004 | Rice | A61L 29/085 604/96.01 |
| 2006/0093771 A1* | 5/2006 | Rypacek | A61L 31/10 428/36.91 |
| 2006/0240253 A1* | 10/2006 | Bavaro | A61L 31/10 428/375 |
| 2009/0297584 A1* | 12/2009 | Lim | A61L 31/10 424/426 |
| 2010/0233236 A1 | 9/2010 | Zhao | |
| 2010/0324645 A1* | 12/2010 | Stankus | A61L 29/085 623/1.11 |
| 2011/0143014 A1* | 6/2011 | Stankus | A61F 2/958 427/2.14 |
| 2011/0160659 A1 | 6/2011 | Clarke et al. | |
| 2012/0015019 A1* | 1/2012 | Pacetti | A61K 31/337 424/422 |
| 2013/0303983 A1 | 11/2013 | Barbick et al. | |
| 2014/0277399 A1* | 9/2014 | Pacetti | A61L 27/3604 623/1.42 |

OTHER PUBLICATIONS

Byrne RA, Joner M, Alfonso F, Kastrati A. Drug-coated balloon therapy in coronary and peripheral artery disease. Nat Rev Cardiol 2014;11:13-23.

Cakic M, Nikolic G, Ilic L, Stankovic S. Synthesis and FTIR characterization of some dextran sulphates. Chemical Industry and Chemical Engineering Quarterly 2005;11:74-78.

De Labriolle A, Pakala R, Bonello L, Lemesle G, Scheinowitz M, Waksman R. Paclitaxeleluting balloon: from bench to bed. Catheter Cardiovasc Interv 2009;73:643-52.

De Raucourt E, Mauray S, Chaubet F, Magia-Revel O, Jozefowicz M, Fischer Am. Anticoagulant activity of dextran derivatives. J Biomed Mater Res 1998;41:49-57.

Gallo, A, & Mani, G. (2013). A stent for co-delivering paclitaxel and nitric oxide from abluminal and luminal surfaces: Preparation, surface characterization, and in vitro drug release studies. Applied Surface Science, 279, 216-232.

Granada JF, Stenoien M, Buszman PP, Tellez A, Langanki D, Kaluza GL, Leon MB, Gray W, Jaff MR, Schwartz RS. Mechanisms of tissue uptake and retention of paclitaxel-coated balloons: impact on neointimal proliferation and heafing. Open Heart 2014;1:e000117.

Huang P, Dong A, Caughey WS. Effects of dimethyl sulfoxide, glycerol, and ethylene glycol on secondary structures of cytochrome c and lysozyme as observed by infrared spectroscopy. J Pharm Sci 1995;84:387-392.

Kakade S, Mani G. A comparative study of the effects of vitamin C, sirolimus, and paclitaxel on the growth of endothelial and smooth muscle cells for cardiovascular medical device applications. Drug Des Devel Ther 2013;7:529-544.

Lamichhane S, Gallo A, Mani G. A polymer-free paclitaxel eluting coronary stent: effects of solvents, drug concentrations and coating methods. Ann Biomed Eng 2014;42:1170-84.

Lamichhane S, Lancaster S, Thiruppathi E, Mani G. Interaction of endothelial and smooth muscle cells with cobalt-chromium alloy surfaces coated with paclitaxel deposited selfassembled monolayers. Langmuir 2013;29:14254-14264.

International Search Report for PCT/US2015/057103, dated Mar. 23, 2016.

Lancaster S, Kakade S, Mani G. Microrough cobalt-chromium alloy surfaces for paclitaxel delivery: preparation, characterization, and in vitro drug release studies. Langmuir 2012;28:11511-11526.

Mani, G.; Macias, C. E.; Feldman, M. D.; Marton, D.; Oh, S.; Agrawal, C. M., Delivery of paclitaxel from cobalt-chromium alloy surfaces without polymeric carriers. Biomaterials 2010, 31 (20), 5372-5384.

Mori T, Kinoshita Y, Watanabe A, Yamaguchi T, Hosokawa K, Honjo H. Retention of paclitaxel in cancer cells for 1 week in vivo and in vitro. Cancer Chemotherapy and Pharmacology 2006;58:665-672.

Nikolic GS, Cakic M, Mitic Z, Ilic L. Deconvoluted Fourier-transform LNT-IR study of coordination copper (II) compounds with dextran derivatives. Russian Journal of Coordination Chemistry 2008;34:322-328.

Pastormerlo LE, Ciardetti M, Trianni G, Ravani M, Shlueter M, Vaghetti M, Coceani M, Rizza A, Berti S, Palmieri C. Drug Eluting Balloon: A Multipurpose Tool for Coronary Revascularization With Optimal Long-Term Follow-Up Results. Journal of Interventional Cardiology 2014;27:574-579.

Scheller B, Speck U, Abramjuk C, Bernhardt U, Bohm M, Nickenig G. Paclitaxel balloon coating, a novel method for prevention and therapy of restenosis. Circulation 2004;110:810-814.

Stoebner, S. E., & Mani, G. (2012). Effect of processing methods on drug release profiles of anti-restenotic self-assembled monolayers. Applied Surface Science, 258(12), 5061-5072.

Thiruppathi E, Mani G. Vitamin-C Delivery from CoCr Alloy Surfaces Using Polymer-Free and Polymer-Based Jlatforms for Cardiovascular Stent Applications. Langmuir 2014;30:6237-6249.

Thukkani AK, Kinlay S. Endovascular Intervention for Peripheral Artery Disease. Circulation Research 2015;116:1599-1613.

Waksman R, Pakala R. Drug-eluting balloon: the comeback kid? Circ Cardiovasc Interv 2009;2:352-8.

* cited by examiner

| Sample | Width (cm) | Thickness (μm) | Tensile Strength (MPa) | Strain At Break (%) | Modulus (MPa) |
|---|---|---|---|---|---|
| Ctrl-DS-1 | 1 | 600.7 ± 121.9 | 0.58 ± 0.09 | 391.16 ± 48.40 | 8.85 ± 2.89 |
| PAT-DS-1 | 1 | 618 ± 30.9 | 0.44 ± 0.05 | 388.44 ± 13.75 | 4.45 ± 1.12 |
| Ctrl-DS-2 | 1 | 699.6 ± 128.9 | 0.12 ± 0.01 | 523.80 ± 90.41 | 0.88 ± 0.49 |
| PAT-DS-2 | 1 | 777.5 ± 40.9 | 0.14 ± 0.04 | 417.45 ± 69.93 | 1.87 ± 1.53 |

FORMULATIONS FOR TAILORED DRUG RELEASE

CROSS REFERENCE

This application is a continuation of U.S. application Ser. No. 14/921,531 filed Oct. 23, 2015, which claims priority to U.S. Provisional Patent Application Ser. Nos. 62/067,847 filed Oct. 23, 2014 and 62/196,707 filed Jul. 24, 2015, incorporated by reference herein in their entireties.

BACKGROUND

One of the most important problems with drug-eluting medical devices, such as drug-eluting balloons (DEB) is that a significant amount of drug coated on the balloon is lost (i.e. washed away in the blood stream) before the balloon is positioned at the diseased site for inflation. It is estimated that 80% of the drug is lost before the balloon is inflated at the diseased site. Hence, if the carrier used to hold the drug onto the balloon catheter is loose, most drug will be lost during the passage to the diseased site, and the concentration of the drug at the target site may be too low to be effective. This not only results in delivery of a subtherapeutic level of drug at the treatment site, but also may cause systemic toxicity. Alternatively, if the carrier used is firm and stable to prevent the drug loss during the passage, then there is a risk of not delivering enough drug at the diseased site during the short time of balloon inflation. In this case, the amount of drug delivered may be too small to have any beneficial effect.

SUMMARY OF THE INVENTION

In a first aspect, the invention provides formulations comprising:
  a biocompatible hydrophilic polymer having a thickness of between about 1 µm and about 1 mm and an elastic modulus of between about 0.05 MPa and about 1000 MPa; and
  a therapeutic disposed within the hydrophilic polymer,
  wherein the polymer provides for release of about 0% to about 30% the therapeutic within about 1 minute after introduction of the formulation into physiological conditions, and wherein the polymer provides for release of at least about 50% to about 100% of the therapeutic within about 20 minutes after introduction of the formulation into physiological conditions.

In one embodiment, the release is measured using high performance liquid chromatography (HPLC). In another embodiment, the polymer comprises poly(ethylene oxide) (PEO), heparin, dextran, dextran sulfate (DS), polyethylene glycol (PEG), butyryl trihexyl citrate (BTC), heparin sulfate (HS), hyaluronic acid (HA), chondroitin sulfate (CS), or combinations thereof. In a further embodiment, wherein the polymer is present at a concentration of between about 1 µg/mm² and 2000 µg/mm². In another embodiment, the polymer thickness is between about 50 µm and about 500 µm. In a still further embodiment, the polymer thickness is between about 50 µm and about 200 µm.

In one embodiment, the polymer is PEO, and wherein the PEO has an average molecular weight range of between about 100 Daltons (Da) and about 10,000,000 Da. In another embodiment, the PEO has an average molecular weight range of between about 50,000 Da and about 200,000 Da. In another embodiment, one or more of the following is true:

(a) the elastic modulus is between about 308 MPa and about 485 MPa;
(b) the formulation possesses a strain at break of between about 2.3% and about 4.2%; and
(c) the formulation possesses a tensile strength of between about 4.1 MPa and about 7.4 MPa.

In a further embodiment, the polymer comprises DS, and wherein the DS has an average molecular weight of between about 100 Da and about 10,000,000 Da. In one embodiment, the DS has an average molecular weight of between about 100,000 Da and about 1,000,000 Da. In another embodiment, one or more of the following is true:

(a) the elastic modulus is between about 0.34 MPa and about 5.7 MPa;
(b) the formulation possesses a strain at break of between about 347% and about 490%; and
(c) the formulation possesses a tensile strength of between about 0.10 MPa and about 0.5 MPa.

In another aspect, the invention provides formulations comprising:
  poly(ethylene oxide) (PEO) having (a) a thickness of between about 1 µm and about 1 mm; (b) an average molecular weight range of between about 50,000 Da and about 200,000 Da; and (c) an elastic modulus of between about 0.05 MPa and about 1000 MPa; and
  a therapeutic disposed within the PEO.

In a further aspect, the invention provides formulations comprising:
  dextran sulfate (DS) having (a) a thickness of between about 1 µm and about 1 mm; (b) an average molecular weight range of between about 100,000 Da and about 1,000,000 Da; and (c) an elastic modulus of between about 0.05 MPa and about 1000 MPa; and
  a therapeutic disposed within the DS.

In one embodiment of any aspect of the formulations of the invention, the polymer comprises a single polymer layer, and wherein the polymer provides for release of about 1% to about 30% of the therapeutic within about one minute after introduction of the formulation into physiological conditions, and release of at least about 50% to about 100% of the therapeutic within 4-12 minutes after introduction of the formulation into physiological conditions. In various embodiments, polymer is between about 10 µm and about 500 µm in thickness or between about 100 µm and about 500 µm in thickness.

In another embodiment of any aspect of the formulations of the invention, the polymer comprises a plurality of polymer layers including at least a first polymer layer and a second polymer layer, wherein the first polymer layer provides for release of about 10% to about 60% of the therapeutic within about 4 minutes after introduction of the formulation into physiological conditions, and the second polymer layer provides for release of at least about another 10% to about 60% of the therapeutic within 8 minutes after introduction of the formulation into physiological conditions. In one embodiment, the polymer further comprises a third polymer layer, wherein the third polymer layer provides for release of at least about another about 10% to about 60% of the therapeutic within about 12 minutes after introduction of the formulation into physiological conditions. In one embodiment, each polymer layer comprises the same polymer, such as PEO or DS. In another embodiment, the first polymer layer, the second polymer layer, and the third polymer layer, when present, do not all comprise the same polymer.

In a further embodiment, the formulation further comprises an inert polymer layer, wherein the insert polymer layer is (a) disposed over the single polymer layer in single polymer layer embodiments, or (b) disposed between the first polymer layer and the second polymer layer and/or between the second polymer layer and the third polymer layer, when present, in the polymer comprising a plurality of polymer layers.

In various embodiments, the inert polymer payer is between about 0.1 µm and about 50 µm in thickness, or between about 1 µm and about 35 µm in thickness. In various embodiments, the inert polymer layer comprises the same polymer as, or a different polymer than, as the single polymer layer in the single polymer layer embodiment, or the first polymer layer, the second polymer layer, and the third polymer layer when present in the embodiment with a plurality of polymer layers.

In various embodiments, the polymer further comprises a plasticizer and/or an excipient. In one embodiment, the therapeutic is selected from the group consisting of alkylating agents, angiogenesis inhibitors, antibodies, antimetabolites, antimitotics, antiproliferatives, aurora kinase inhibitors, apoptosis promoters, activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPB) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), and topoisomerase inhibitors, and derivatives and combinations thereof. In another embodiment, the therapeutic comprises paclitaxel and/or paclitaxel albumin bound particles.

In another aspect the invention provides medical devices comprising the formulation of any embodiment or combination of embodiments of the formulations of the invention disposed on a surface of the medical device. In one embodiment, the medical device is selected from the group consisting of: balloon catheters, drug-eluting stents, vascular grafts, heart valves, pacemakers, artificial heart, ventricular assist devices, cardiopulmonary bypass, orthopedic devices, fracture fixation devices, dental devices, neural devices, stent grafts, heart-lung machines, hemodialysis machines, ocular implants and devices, and cochlear implants and devices. In a further embodiment, the medical device comprises a balloon portion of a balloon catheter. In another embodiment, the polymer comprises a single layer of PEO, and wherein the thickness of the PEO layer is between about 50 µm and about 500 µm. In a further embodiment, the polymer comprises a single layer of DS, and wherein the thickness of the DS layer is between about 50 µm and about 500 µm. In another embodiment, the therapeutic comprises paclitaxel and/or paclitaxel albumin bound particles.

In another aspect, the invention provides medical devices comprising an array of the formulation of any embodiment or combination of embodiments of the invention on a surface of the medical device, wherein the array comprises:

one or more positions comprising a first formulation position; and one or more positions comprising a second formulation position;

wherein the first formulation position provides for release of about 10% to about 60% of the therapeutic within about 4 minutes after introduction of the formulation into physiological conditions, and the second formulation position provides for release of at least about another about 10% to about 60% of the therapeutic within about 8 minutes after introduction of the formulation into physiological conditions.

In one embodiment the array further comprises one or more positions comprising a third formulation position, wherein third formulation position provides for release of at least about another 10% to about 60% of the therapeutic within about 12 minutes after introduction of the formulation into physiological conditions. In another embodiment, each formulation position comprises the same polymer, wherein the concentration of the polymer in the first formulation position is less than the concentration of the polymer in the second formulation position, and wherein the concentration of the polymer in the second formulation position is less than the concentration of the polymer in the third formulation position when present. In a further embodiment, each formulation position comprises PEO, wherein:

the first formulation position comprises PEO at a concentration of between about 1 µg/mm$^2$ and 200 µg/mm$^2$;

the second formulation position comprises PEO at a concentration of between about 10 µg/mm$^2$ and 300 µg/mm$^2$; and the third formulation position, when present, comprises PEO at a concentration of between about 25 µg/mm$^2$ and 500 µg/mm$^2$.

In another embodiment, each formulation position comprises DS, and wherein:

the first formulation position comprises DS at a concentration of between about 1 µg/mm$^2$ and 200 µg/mm$^2$;

the second formulation position comprises DS at a concentration of between about 10 µg/mm$^2$ and 300 µg/mm$^2$; and the third formulation position, when present, comprises DS at a concentration of between about 25 µg/mm$^2$ and 500 µg/mm$^2$.

In a further embodiment, the first formulation position, the second formulation position, and the third formulation position when present do not all comprise the same polymer.

In another aspect, the invention provides methods of using the medical device of any embodiment or combination of embodiments of the invention, wherein the method comprises:

inflating the balloon at a first location in a target blood vessel in a subject in need thereof for a first time period such that a first amount of the therapeutic is delivered to the first location in the target vessel;

deflating the balloon and moving the balloon catheter to a second location in the target blood vessel; and inflating the balloon at the second location for a second time period such that a second amount of the therapeutic is delivered to the second location in the target vessel.

In one embodiment, the subject is suffering from one or more of coronary artery disease, peripheral vascular disease, carotid artery disease, or cerebral artery disease.

In a further aspect, the invention provides methods of manufacturing a drug-coated medical device comprising:

(a) dipping a medical device into a solution comprising between about 10 weight percent and about 25 weight percent of a hydrophilic polymer and between about 0.6 weight percent and about 1.5 weight percent of a therapeutic to form a dipped medical device; and (b) drying the dipped medical device at about 50 degrees Celsius for between about 1 minute and about 96 hours to form the drug-coated medical device.

In one embodiment, the method further comprises repeating steps (a) and (b) a desired number of times to form a multi-layer drug-coated medical device. In another embodiment, the medical device is a balloon portion of a balloon catheter, and wherein the balloon is inflated prior to step (a). In a further embodiment, the balloon is inflated with a water/saline solution and wherein the water/saline solution is at a temperature of between about 37° C. to about 80° C.

In another aspect, the invention provides methods of manufacturing a drug-coated medical device comprising:

(a) placing a mask with a design on a surface of the medical device;

(b) applying a coating of a drug to the surface of the medical device to form a wet coated medical delivery device;

(c) drying the coated medical delivery device at about 50° C. for between about 1 minute and about 96 hours to form a dry coated medical device; and (d) removing the mask from the surface of the medical device thereby forming a drug-coated medical device.

In one embodiment, the coating of the drug is sprayed on the surface of the medical device to form the wet coated medical delivery device. In another embodiment, the medical device is dipped in the drug to form the wet coated medical delivery device.

In a further aspect, the invention provides methods of manufacturing a drug-coated balloon portion of a balloon catheter comprising:

(a) inflating the balloon with a pressure of about 1-8 atm;

(b) dipping the balloon in a coating solution comprising a biocompatible hydrophilic polymer and a therapeutic for about 1 second to 4 hours to form a wet coated balloon;

(c) drying the wet coated balloon in air at about 50° C. for about 10 minutes to about 4 hours to form a dry coated balloon;

(d) dipping the dry coated balloon in the coating solution of step (b) for about 1 second to about 1 hour to form a doubly wet coated balloon;

(e) drying the doubly wet coated balloon in air at about 50° C. for about 10 minutes to about 4 hours to for a doubly dry coated balloon; and (f) repeating steps (d) and (e) 1 more time to 20 more times to form the drug-coated balloon.

In a still further aspect, the invention provides methods of manufacturing a drug-coated balloon portion of a balloon catheter comprising:

(a) inflating the balloon with a pressure of about 1-8 atm;

(b) dipping the balloon in a coating solution comprising a biocompatible hydrophilic polymer and an therapeutic for about 1 second to about 4 hours to form a first wet coated balloon;

(c) removing the wet coated balloon from the coating solution;

(d) dipping the wet coated balloon in a solvent selected from the group consisting of ethanol, dimethyl sulfoxide (DMSO), methanol, acetone, dimethyl formamide (DMF), acetonitrile, chloroform, methylene chloride, tetrahydrofuran, ethyl acetate, or a mixture thereof for about 1 second to 4 hours;

(e) repeating step (d) 1-10 more times, wherein new solvent is used each time, in order to form a coated and dehydrated balloon;

(f) dipping the coated and dehydrated balloon in a solution of solvent and glycerol for about 1 second to 4 hours;

(g) repeating step (f) with a solution of solvent and glycerol to form a second wet coated balloon; and (h) drying the second wet coated balloon for about 1 minute to 4 hours in order to for the drug-coated balloon.

In another aspect, the invention provides drug delivery balloon apparatuses comprising:

a housing having a first lumen and a second lumen;

a catheter having a first end coupled to the housing;

a balloon inflation port coupled to one or more of the housing and the first lumen;

a guidewire port coupled to one or more of the housing and the second lumen;

a drug delivery balloon coupled to a second end of the catheter and configured for fluid communication with the first lumen of the housing; and one or more indicators coupled to the housing, wherein the one or more indicators are configured to provide a visual representation of one or more inflation periods for the drug delivery balloon.

In one embodiment, an outer surface of the drug delivery balloon comprises a drug formulation. In another embodiment, the one or more inflation periods for the drug delivery balloon comprise at least two inflation periods. In a further embodiment, the one or more indicators comprises a timer; in one embodiment, the timer comprises a control configured to start the timer. In further embodiments, the apparatus may further comprise a pressure sensor coupled to the catheter, wherein the one or more indicators is configured to provide the one or more visual representations in response to a change in pressure detected by the pressure sensor, and/or may further comprise comprising a thermometer coupled to the catheter, wherein the one or more indicators is configured to provide the one or more visual representations in response to a change in temperature detected by the thermometer. In another embodiment, at least one of the one or more indicators is configured to display one or more colors. In one such embodiment, at least one indicator of the one or more indicators is configured to display a first color during a first portion of a given inflation period, and wherein the at least one indicator is configured to display a second color during a second portion of the given inflation period. In another embodiment, the one or more indicators comprise:

a first indicator configured to provide a visual representation of a first inflation period for the drug delivery balloon;

a second indicator configured to provide a visual representation of a second inflation period for the drug delivery balloon; and a third indicator configured to provide a visual representation of a third inflation period for the drug delivery balloon.

In various embodiments, the drug delivery balloon has an inflated diameter in the range from about 1 mm to about 40 mm, ranges in length from about 20 mm to about 300 mm, and/or the second lumen has a diameter in the range of about 0.008 inches to about 0.05 inches. In another embodiment, the drug formulation comprises the formulation of any embodiment or combination of embodiments of the invention disposed on a surface of the drug delivery balloon. In one such embodiment, the polymer comprises a single layer of PEO, and wherein the thickness of the PEO layer is between about 50 μm to 500 μm. In another embodiment, the polymer comprises a single layer of DS, and wherein the thickness of the DS layer is between about 50 µm to 500 µm. In a further embodiment, the therapeutic comprises paclitaxel and/or paclitaxel albumin bound particles.

In another embodiment, the invention provides methods for administering at least one drug to a subject in need thereof using the drug delivery balloon apparatus of any embodiment or combination of embodiments of the invention, the method comprising:

advancing the drug delivery balloon apparatus according to any embodiment or combination of embodiments of the invention to a first location in a desired treatment vessel via the catheter;

inflating the drug delivery balloon at the first location via the balloon inflation port;

receiving a visual representation of a completion of a first inflation period from a first indicator;

advancing the drug delivery balloon to a second location in the desired treatment vessel;

inflating the drug delivery balloon at the second location via the balloon inflation port; and receiving a visual representation of a completion of a second inflation period from a second indicator.

In another embodiment, the method further comprises:

advancing the drug delivery balloon apparatus to a third location in the desired treatment vessel;

inflating the drug delivery balloon at the third location via the balloon inflation port; and receiving a visual representation of a completion of a third inflation period from a third indicator.

In another aspect, the invention provides devices comprising:

a housing defining a chamber, wherein the housing includes a distal end and a proximal end;

a plunger rod positioned at the distal end of the housing, wherein the plunger is axially moveable within the chamber;

a tube coupled to the proximal end of the housing and having a lumen configured for fluid communication with the housing;

a pressure gauge positioned between the housing and the lumen;

a heating element positioned coupled to the housing.

In one embodiment, the heating element comprises a resistance wire surrounding the housing. In one such embodiment, the resistance wire comprises a material selected from the group consisting of nichrome, iron-chromium-aluminum alloys, copper alloys, or nickel-chrome alloys. In another embodiment, the device further comprises comprising a power source coupled to the heating element. In a further embodiment, the device further comprises one or more indicators coupled to the device, wherein the one or more indicators are configured to provide a visual representation of one or more time periods. In one such embodiment, the one or more indicators comprise a timer, and the timer may comprise a control configured to start the timer. In another embodiment at least one of the one or more indicators is configured to display one or more colors; in this embodiment, at least one indicator of the one or more indicators may be configured to display a first color during a first portion of a given time period, and the at least one indicator may be configured to display a second color during a second portion of the given time period. In a further embodiment, the device further comprises a thermometer positioned within the chamber; in this embodiment, the one or more indicators may be configured to provide the one or more visual representations in response to a change in temperature detected by the thermometer. In another embodiment, the device may further comprise a temperature readout display coupled to the housing to provide a visual representation of a temperature detected by the thermometer.

In another embodiment, the device further comprises
a balloon inflation port coupled to and configured for fluid communication with the lumen; and
a drug delivery balloon coupled to and configured for fluid communication with the lumen.

In one such embodiment, an outer surface of the drug delivery balloon may comprise a drug formulation. In another embodiment, the one or more time periods comprise one or more inflation periods for the drug delivery balloon. In another embodiment, the one or more indicators comprise:

a first indicator configured to provide a visual representation of a first inflation period for the drug delivery balloon;

a second indicator configured to provide a visual representation of a second inflation period for the drug delivery balloon; and a third indicator configured to provide a visual representation of a third inflation period for the drug delivery balloon.

In various embodiments, the drug delivery balloon may have an inflated diameter in the range from about 1 mm to about 40 mm, and/or the drug delivery balloon may range in length from about 20 mm to about 300 mm. In a further embodiment, the formulation comprises the formulation of any embodiment or combination of embodiments of the invention disposed on a surface of the drug delivery balloon. In one such embodiment, the polymer comprises a single layer of PEO, and wherein the thickness of the PEO layer is between about 50 µm to 500 µm. In another embodiment, the polymer comprises a single layer of DS, and wherein the thickness of the DS layer is between about 50 µm to 500 µm. In a further embodiment, the therapeutic comprises paclitaxel and/or paclitaxel albumin bound particles.

In another embodiment, the invention provides methods for administering at least one drug to a subject in need thereof using a drug delivery balloon apparatus, the method comprising:

heating a solution in the chamber of the device according to any embodiment or combination of embodiments of the invention to a desired temperature via the heating element;

delivering the drug delivery balloon apparatus to a first location in a desired treatment vessel;

inflating the drug delivery balloon at the first location via a balloon inflation port; and receiving a visual representation of a completion of a first inflation period from one or more indicators coupled to the device.

In another embodiment, the method may further comprise
delivering the drug delivery balloon apparatus to a second location in the desired treatment vessel;
inflating the drug delivery balloon at the second location via the balloon inflation port; and
receiving a visual representation of a completion of a second inflation period from the one or more indicators coupled to the device.

In another embodiment, the method may further comprise
delivering the drug delivery balloon apparatus to a third location in the desired treatment vessel;
inflating the drug delivery balloon at the third location via the balloon inflation port; and
receiving a visual representation of a completion of a third inflation period from the one or more indicators coupled to the device.

Balloon coated with formulation. (B) Therapeutic release from the formulation coated on the balloon. PAT is paclitaxel, PEO is poly(ethylene) oxide, and DS is dextran sulfate.

Figure 2:
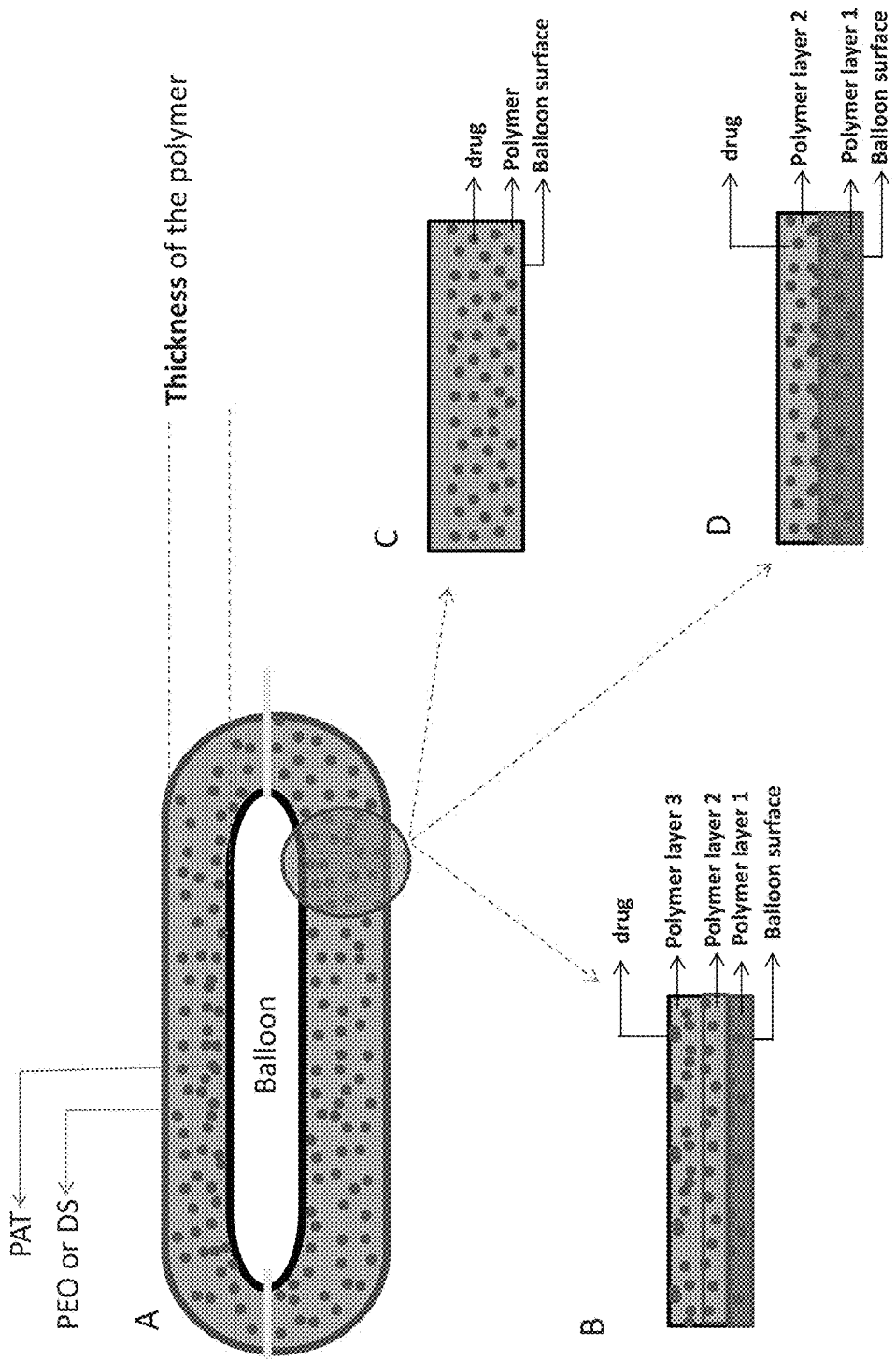

FIG. 2 is a drawing of a multi-use embodiment of the formulations of the invention coated on a balloon. (A) Balloon coated with formulation, showing polymer thickness. (B) Three-polymer layer embodiment. (C) One polymer layer embodiment, with a thick polymer layer to provide for extended release. (D) Two polymer layer embodiment. PAT is paclitaxel, PEO is poly(ethylene) oxide, and DS is dextran sulfate.

Figure 3:
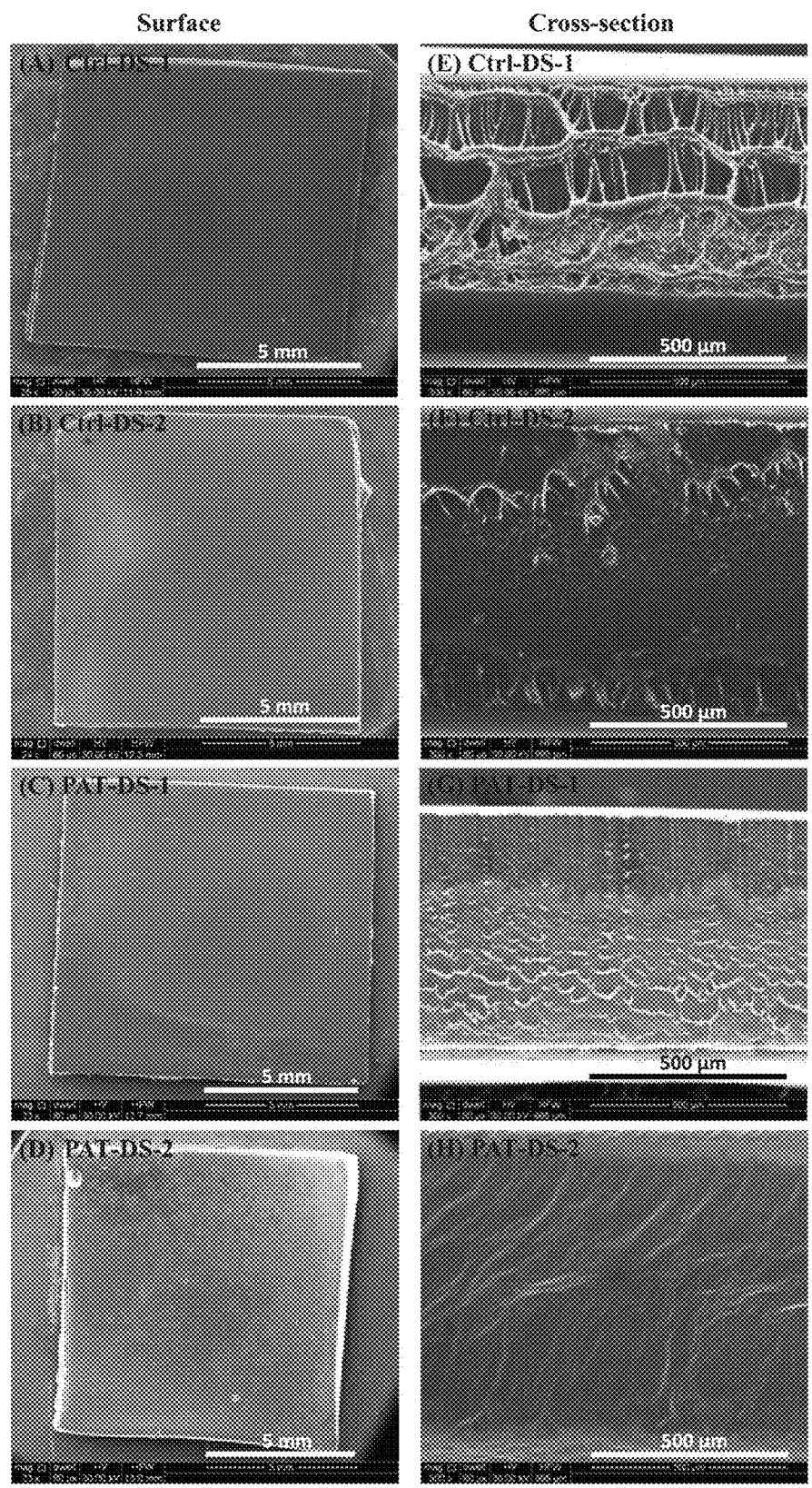

FIG. 3. SEM images of surfaces (A, B, C, D) and cross sections (E, F, G,-H) of Ctrl-DS-1, Ctrl-DS-2, PAT-DS-1, and PATDS-2 films.

Figure 4:
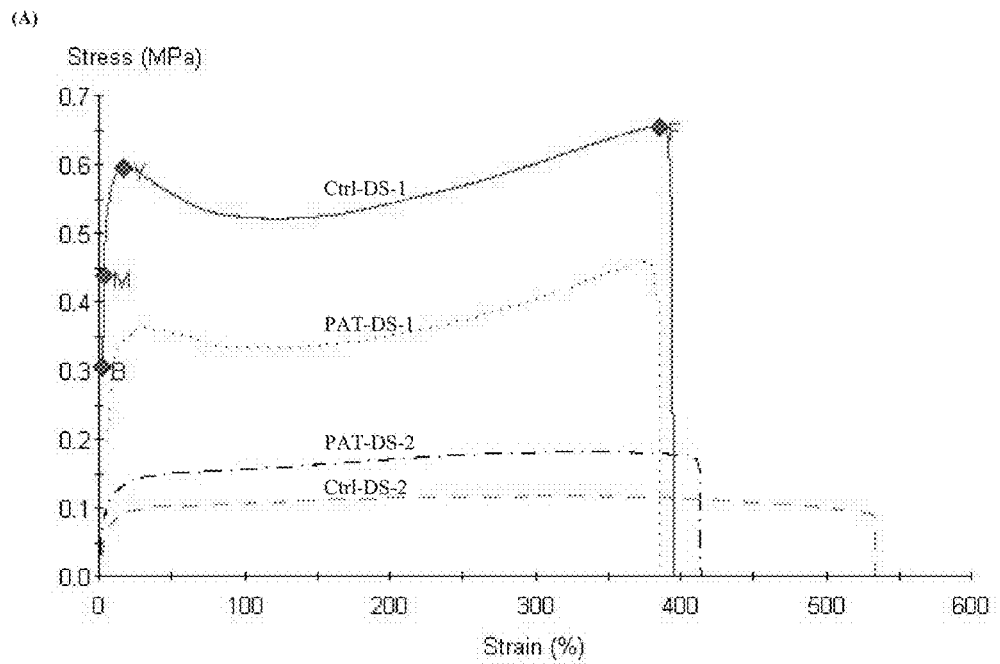

FIG. 4. Stress-strain curves (A) and mechanical properties (B) of Ctrl-DS-1, Ctrl-DS-2, PAT-DS-1, and PAT-DS-2 films.

Figure 5:
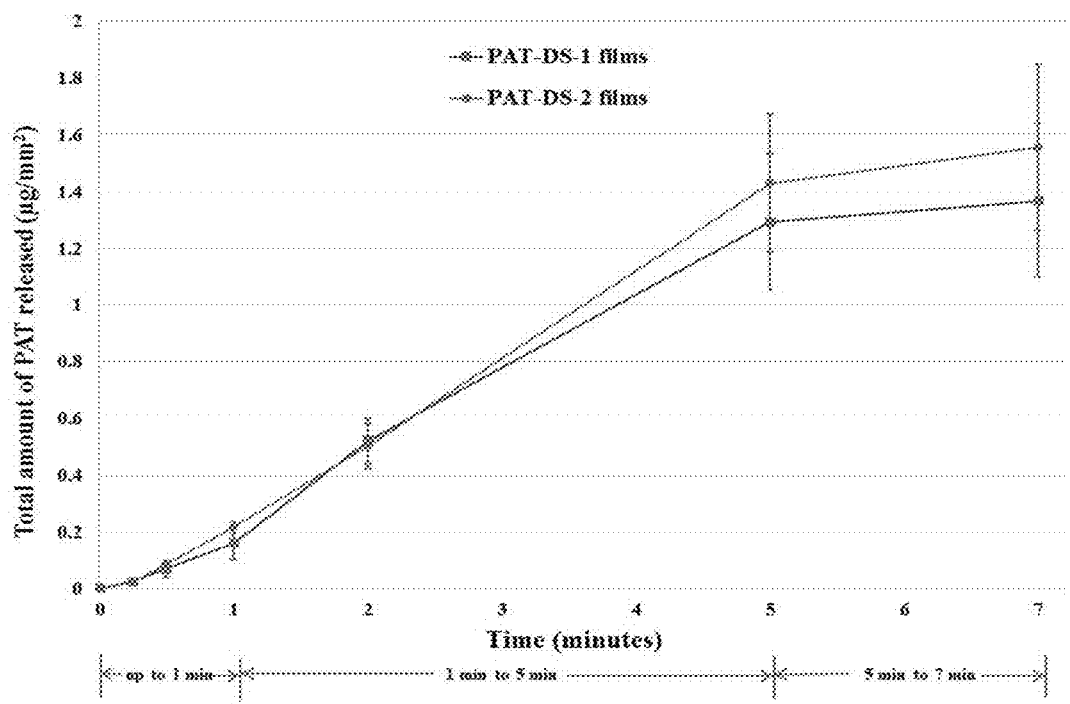

FIG. 5. Cumulative PAT release ($\mu g/mm^2$) for PAT-DS-1 and PAT-DS-2.

Figure 6:
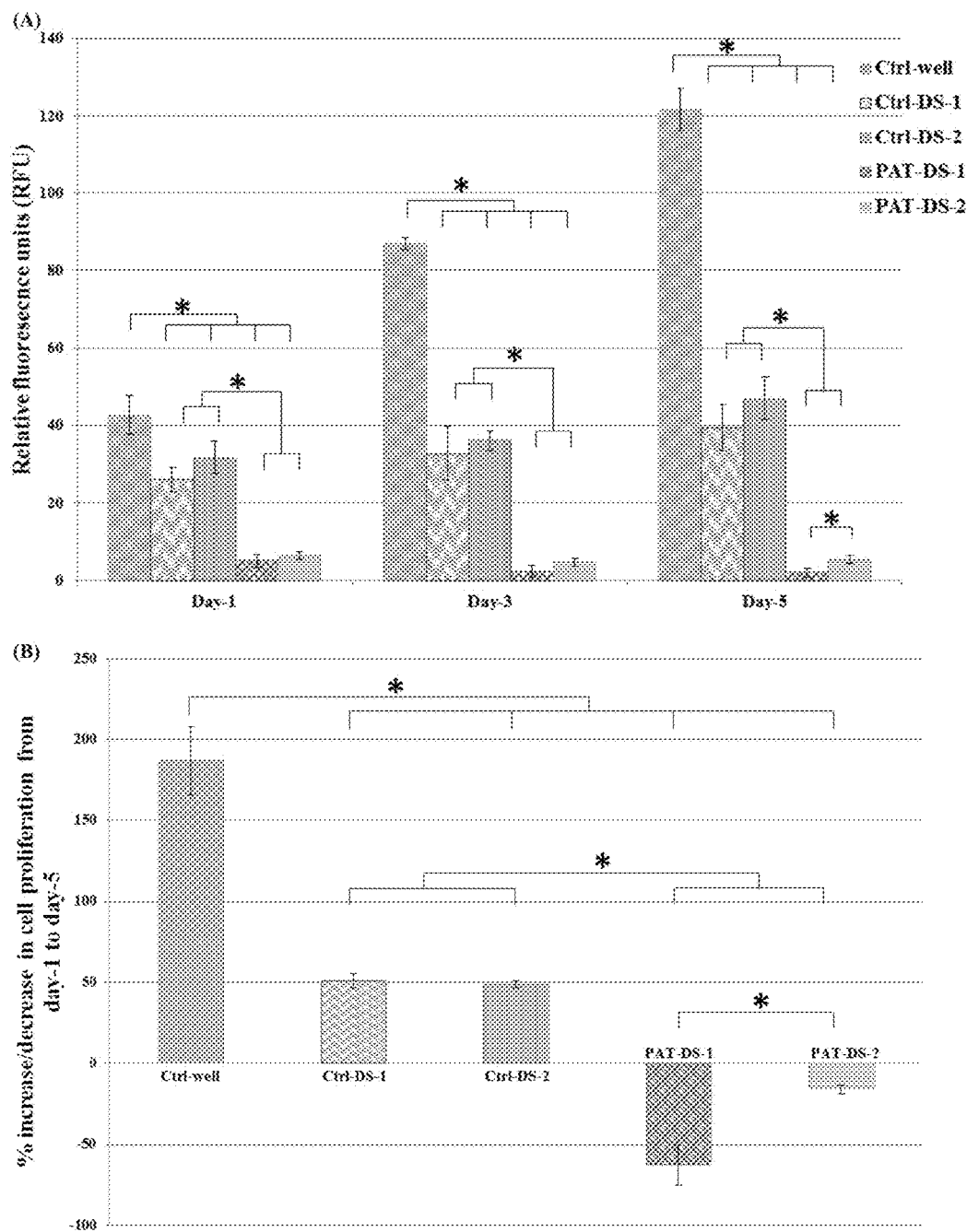

FIG. 6. Viability and proliferation of SMCs on 1, 3, and 5 days (A), percentage of increase or decrease of SMC proliferation from day-1 to day-5 (B) for Ctrl-well, Ctrl-DS-1, Ctrl-DS-2, PAT-DS-1, and PAT-DS-2 films (specimen size: 0.5 cm×0.5 cm). Cells grown in well plate without adding any films is used as control (Ctrl-well). * denotes statistical significance at $p<0.05$.

Figure 7:
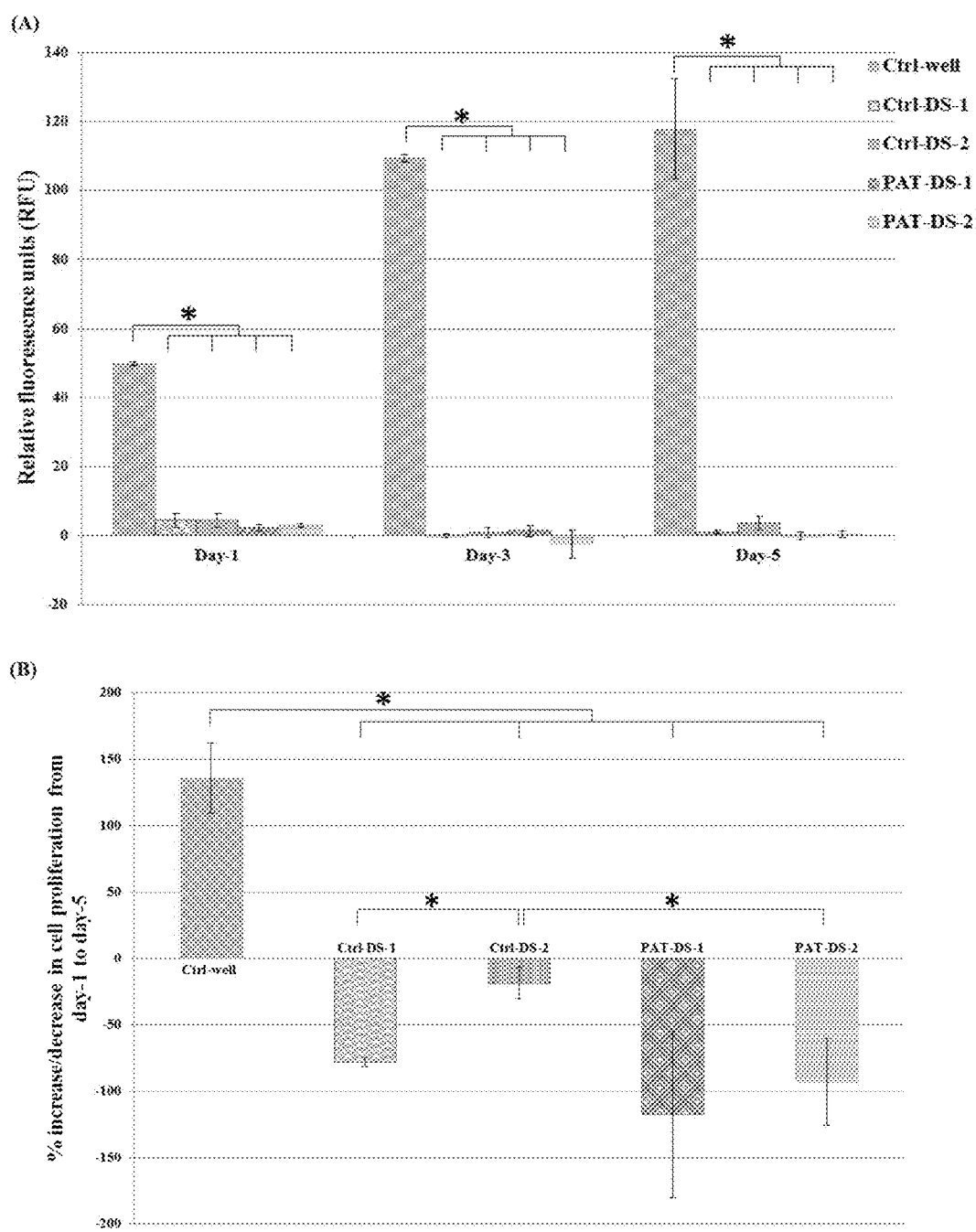

FIG. 7. Viability and proliferation of SMCs on 1, 3, and 5 days (A), percentage of increase or decrease of SMC proliferation from day-1 to day-5 (B) for Ctrl-well, Ctrl-DS-1, Ctrl-DS-2, PAT-DS-1, and PAT-DS-2 films (specimen size: 1 cm×1 cm). Cells grown in well plate without adding any films is used as control (Ctrlwell). * denotes statistical significance at $p<0.05$.

Figure 8:
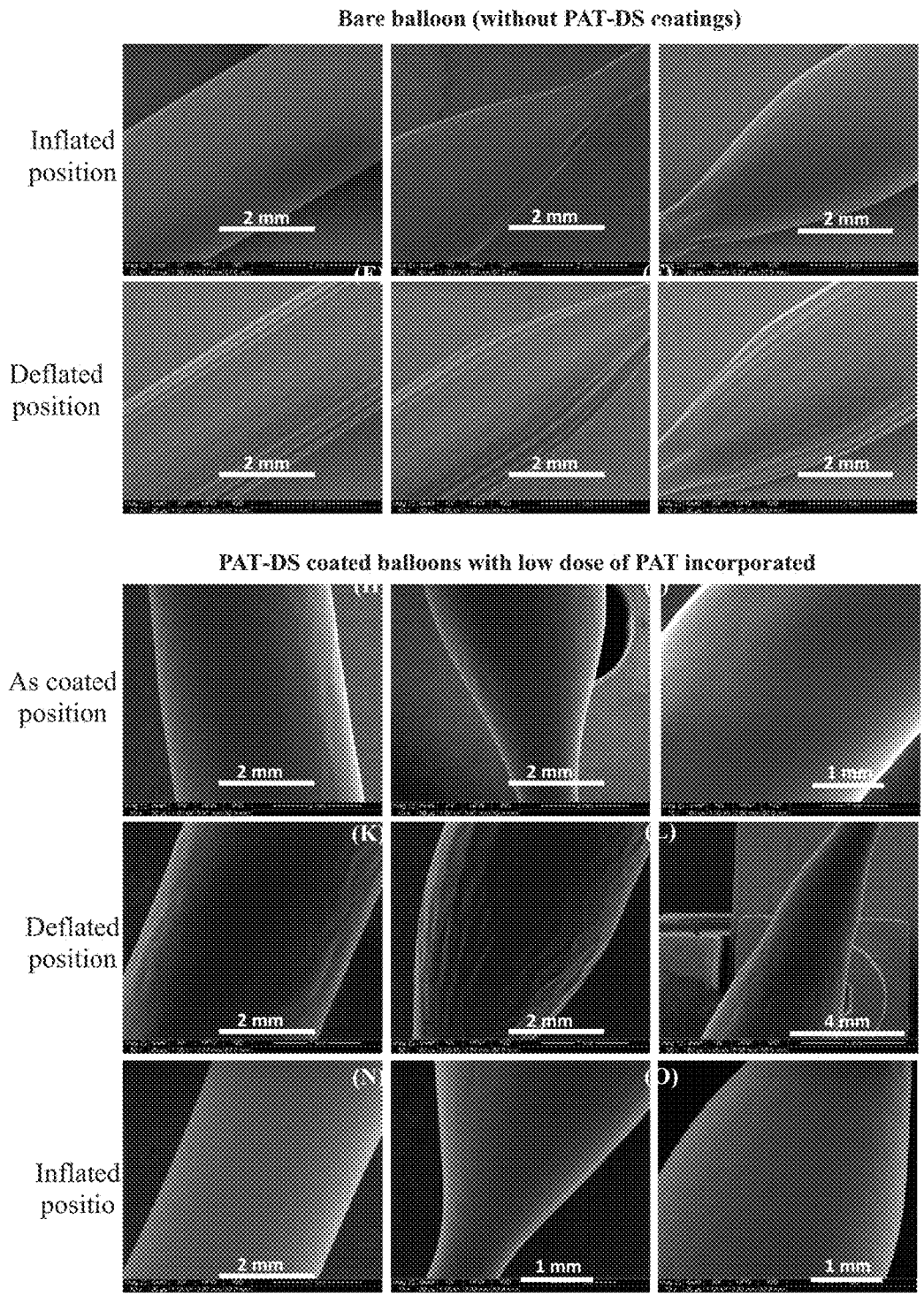

FIG. 8. SEM images of bare balloon (A, B, C, D, E, and -F), and PAT-DS coated balloons with low dose of PAT incorporated (G, H, I, J, K, L, M, N, and -O). The images were acquired at as-coated, deflated, and inflated positions of the balloons.

Figure 9:
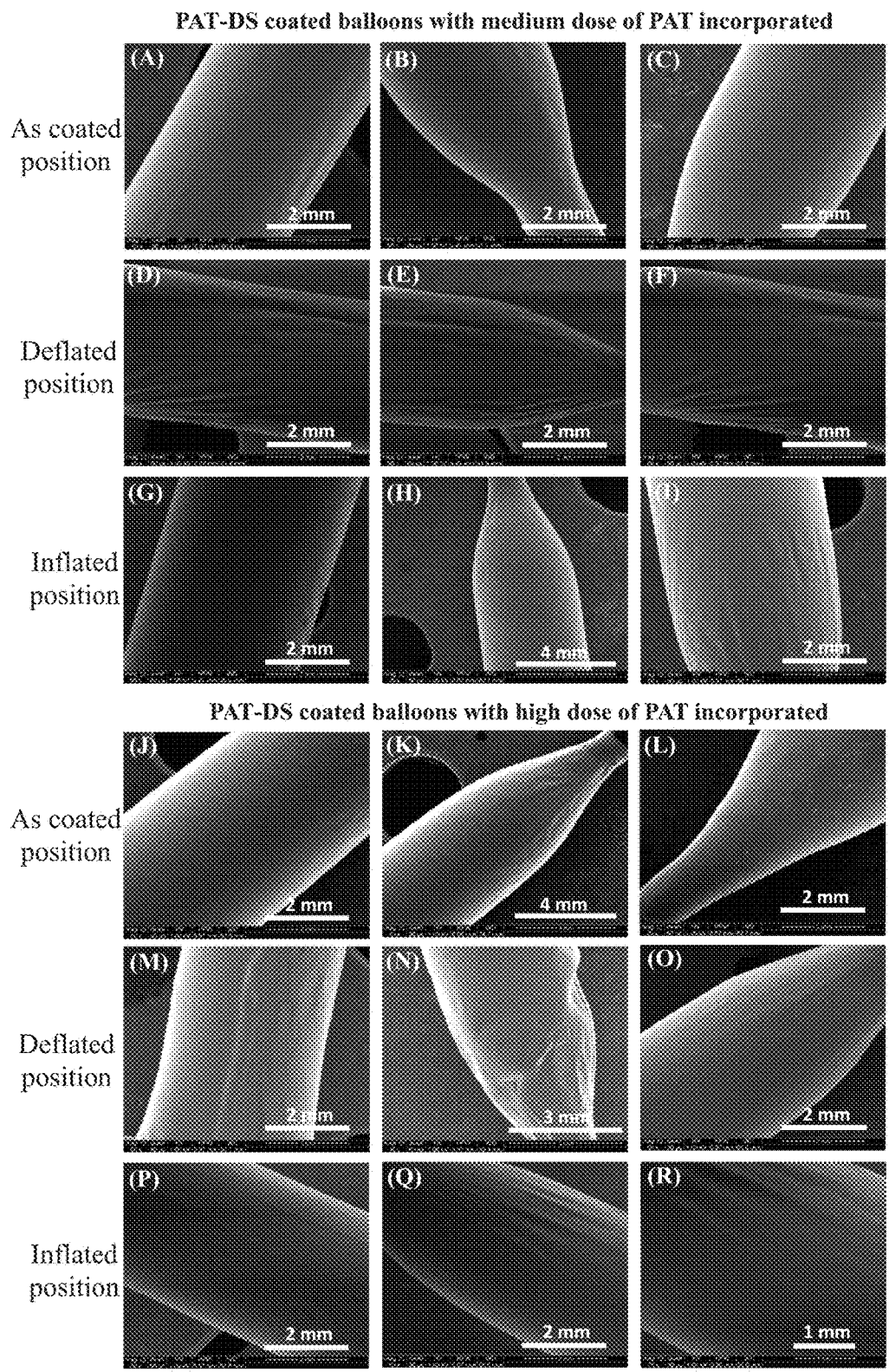

FIG. 9. SEM images of PAT-DS coated balloons with medium dose of PAT (A, B, C, D, E, F, G, H, and I), and high dose of PAT (J, K, L, M, N, O, P, Q and R) incorporated. The images were acquired at as-coated, deflated, and inflated positions of the balloons.

Figure 10:
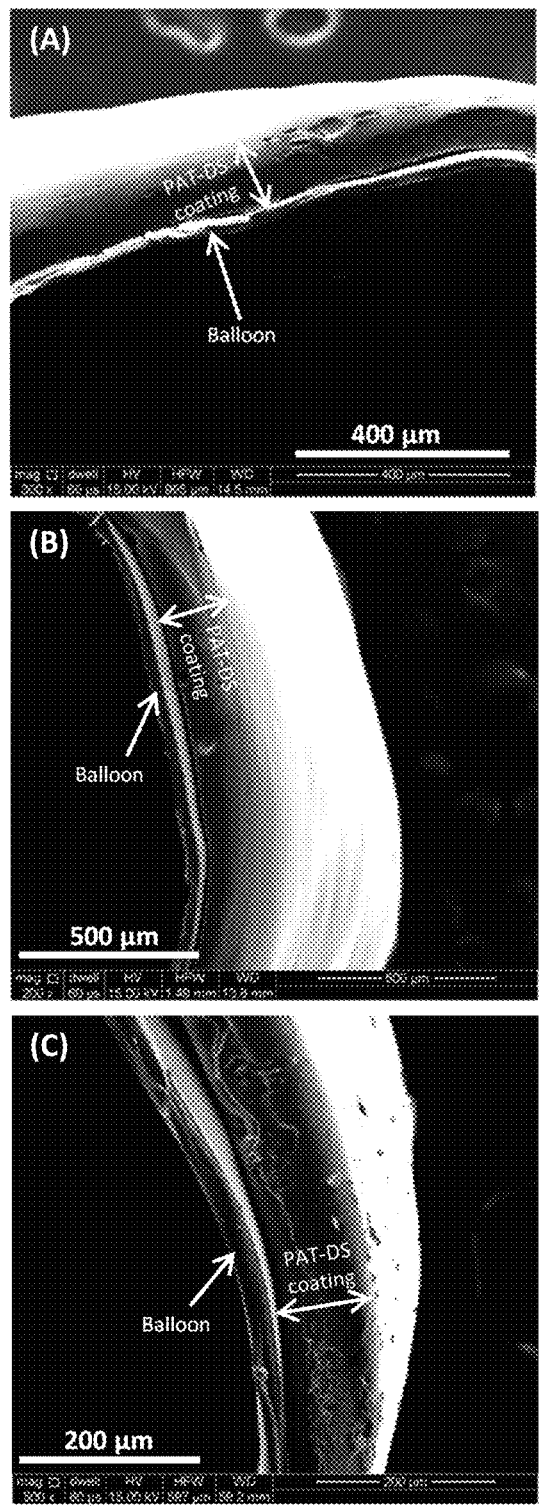

FIG. 10. SEM images of cross-sections of PAT-DS coated balloons with low (A), medium (B), and high (C) doses of PAT incorporated.

Figure 11:
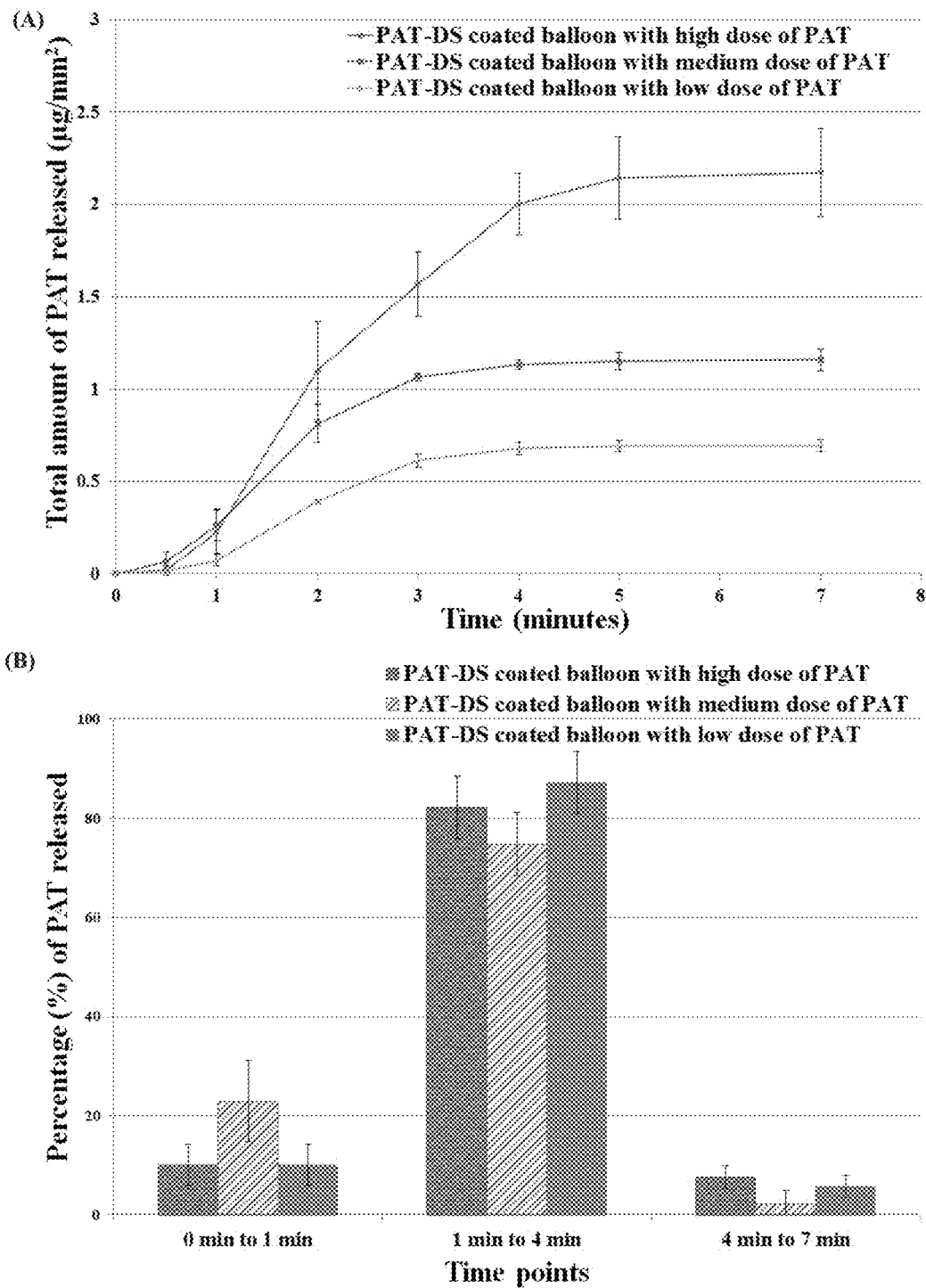

FIG. 11. Cumulative PAT released ($\mu m/mm^2$) (A), and percentage of PAT released (B) from PAT-DS coated balloons with low, medium, and high doses of PAT incorporated.

Figure 12:
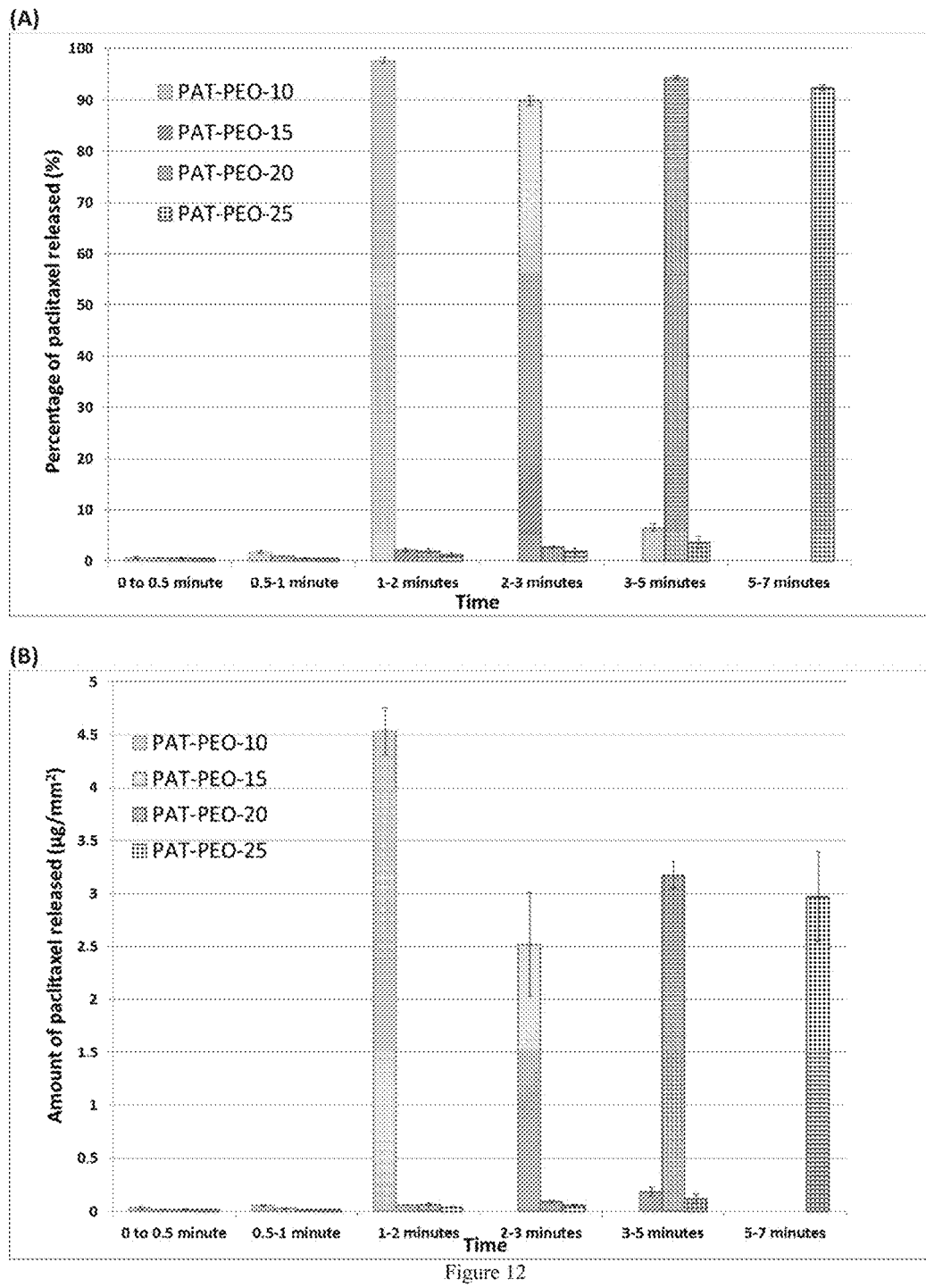

FIG. 12. Percentage (A) and amount (B) of paclitaxel released from PAT-PEO-10, PAT-PEO-15, PAT-PEO-20, and PAT-PEO-25 films.

Figure 13:
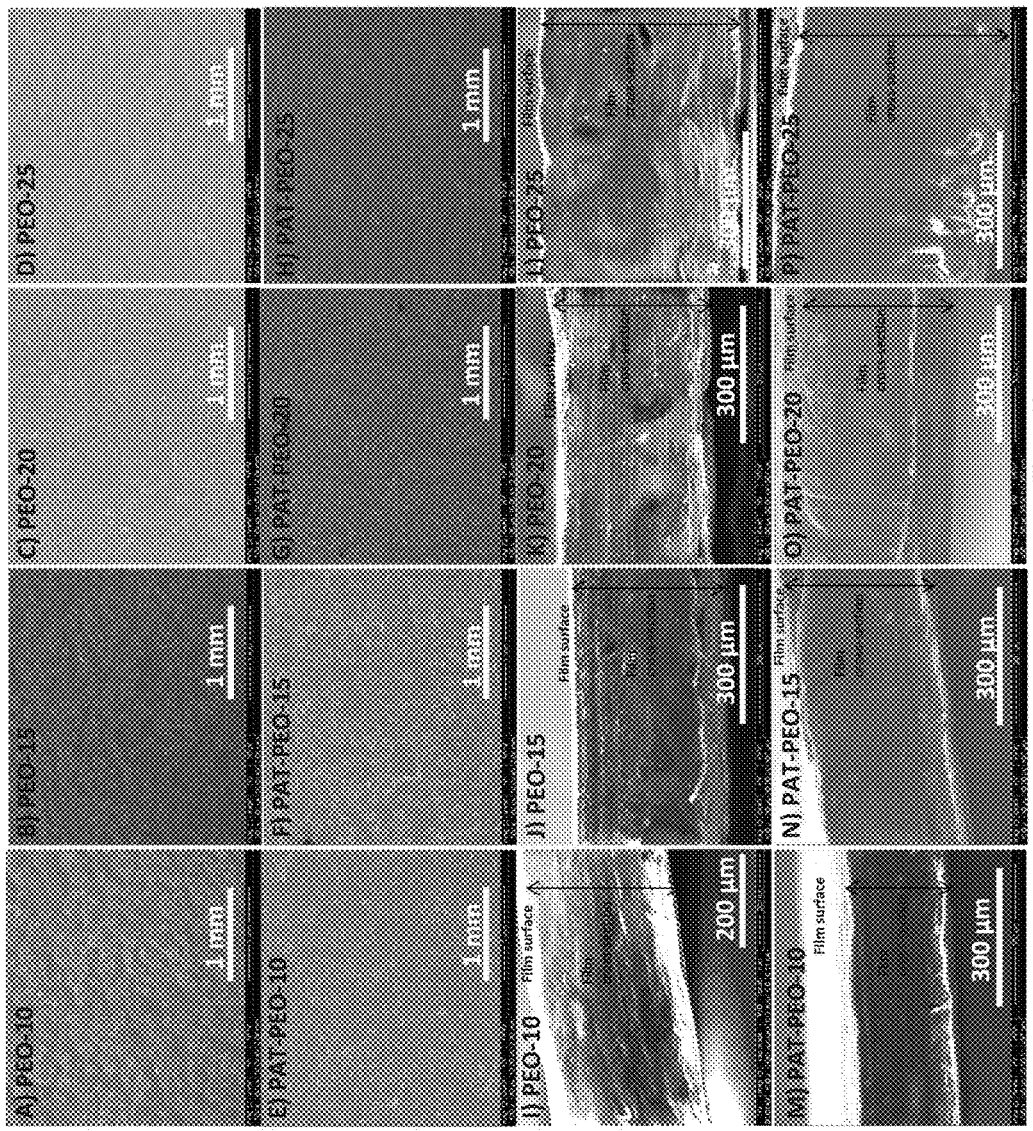

FIG. 13. SEM images of surfaces (A, B, C, D, E, F, G and H) and cross-sections (I, J, K, L, M, N, O, and P) of control PEO films and PAT-PEO films.

Figure 14:
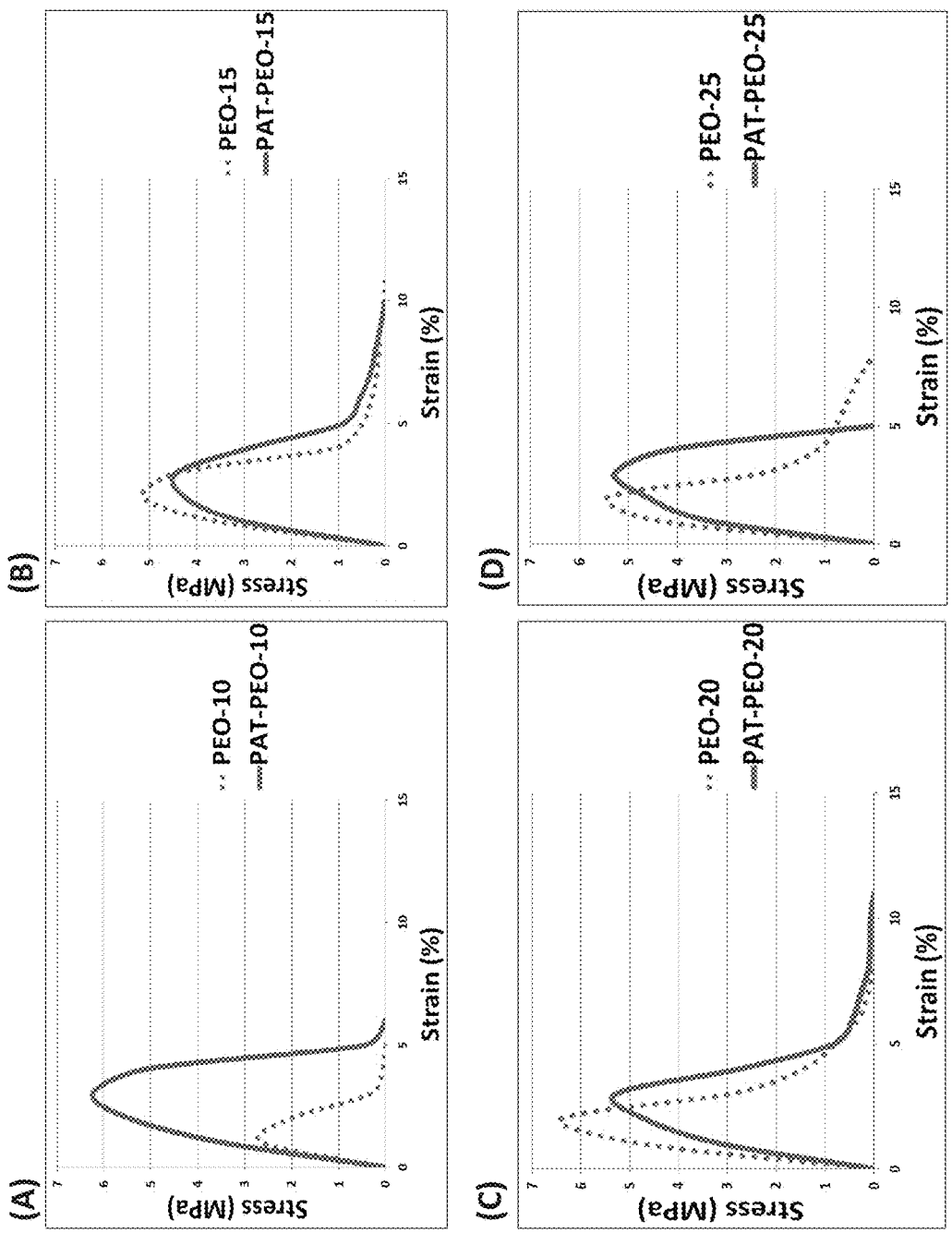

FIG. 14. Stress-strain curves of PEO-10 and PAT-PEO-10 (A), PEO-15 and PAT-PEO-15 (B), PEO-20 and PAT-PEO-20 (C), and PEO-25 and PAT-PEO-25 (D).

Figure 15:
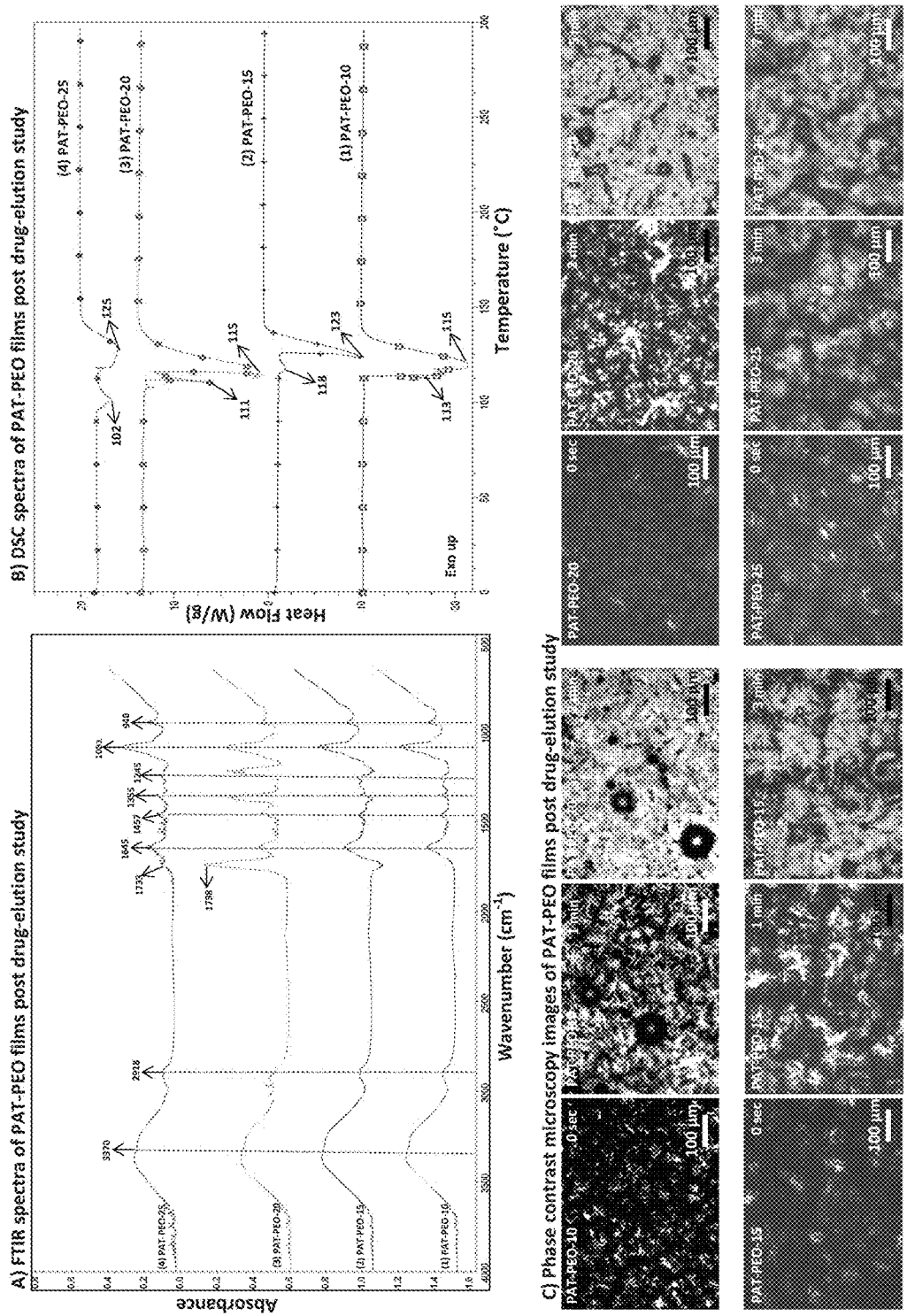

FIG. 15. FTIR spectra (A), DSC spectra (B), and Phase Contrast Microscopy images (C) of PAT-PEO films post drug-elution study.

Figure 16:
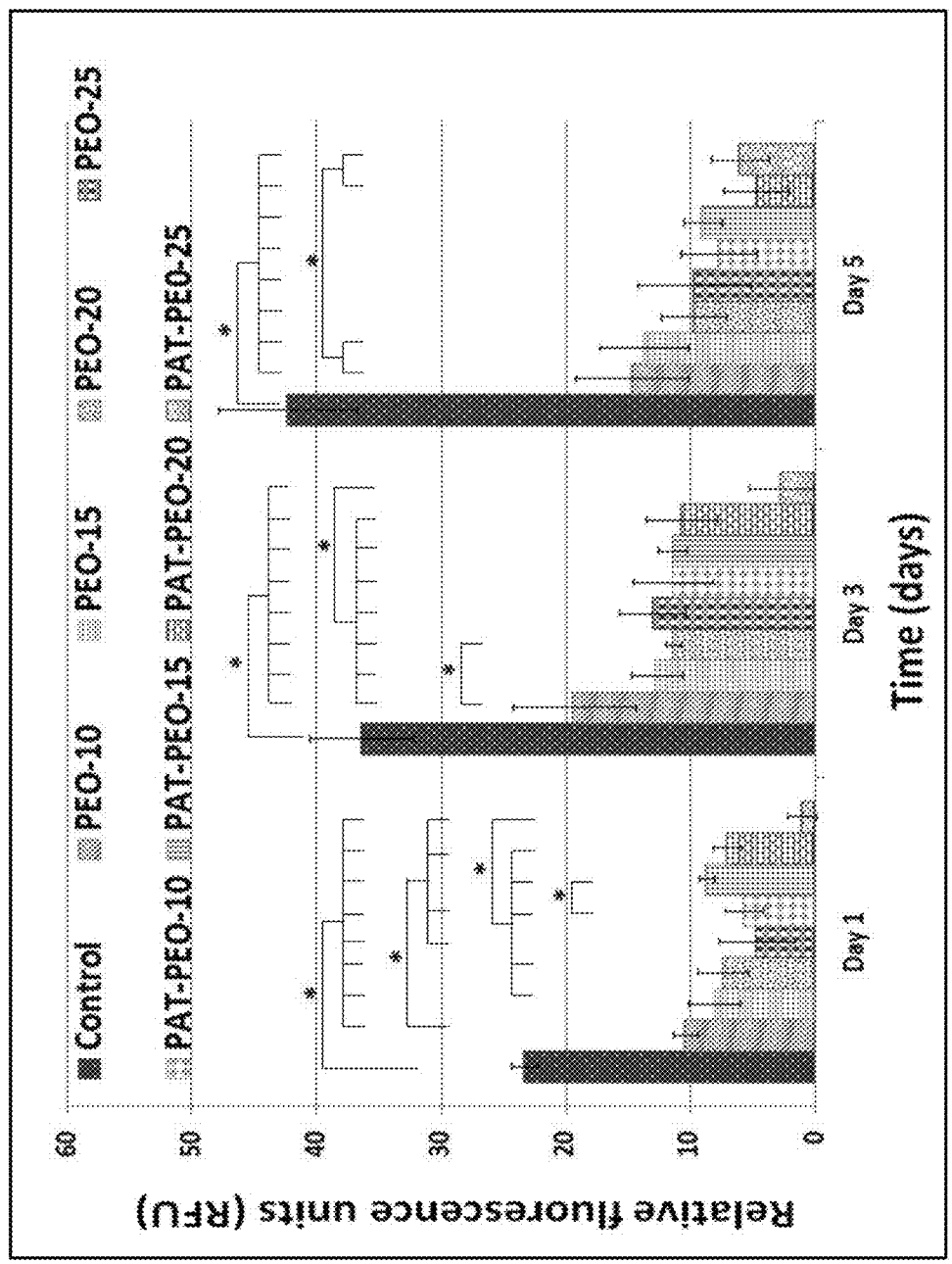

FIG. 16. Viability and proliferation of human aortic smooth muscle cells for control wells (no films), control PEO films, and PAT-PEO films.

Figure 17:
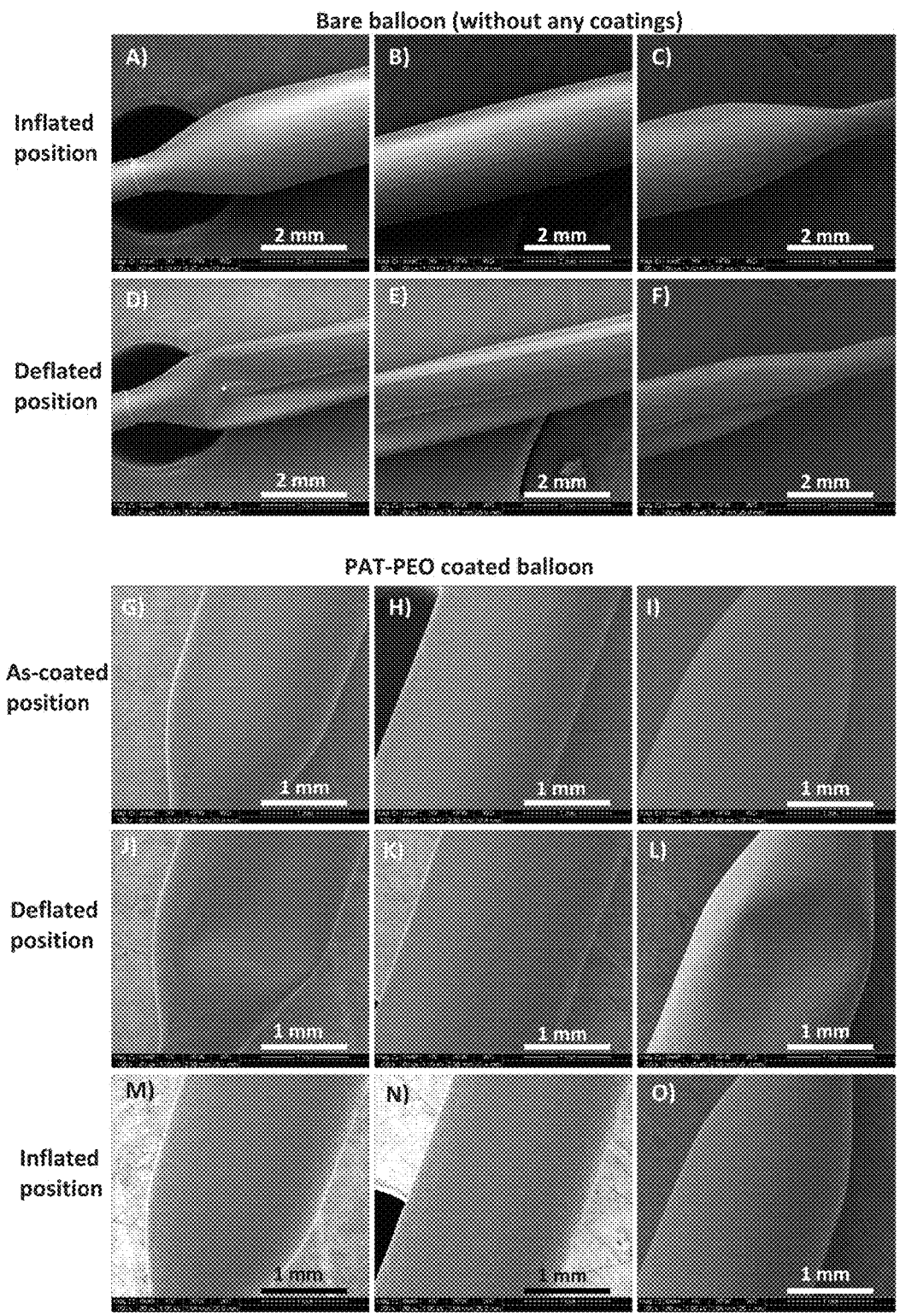

FIG. 17. SEM images of bare balloon (A, B, C, D, E, and, F) and PAT-PEO coated balloon (G, H, I, J, K, L, M, N, and O).

Figure 18:
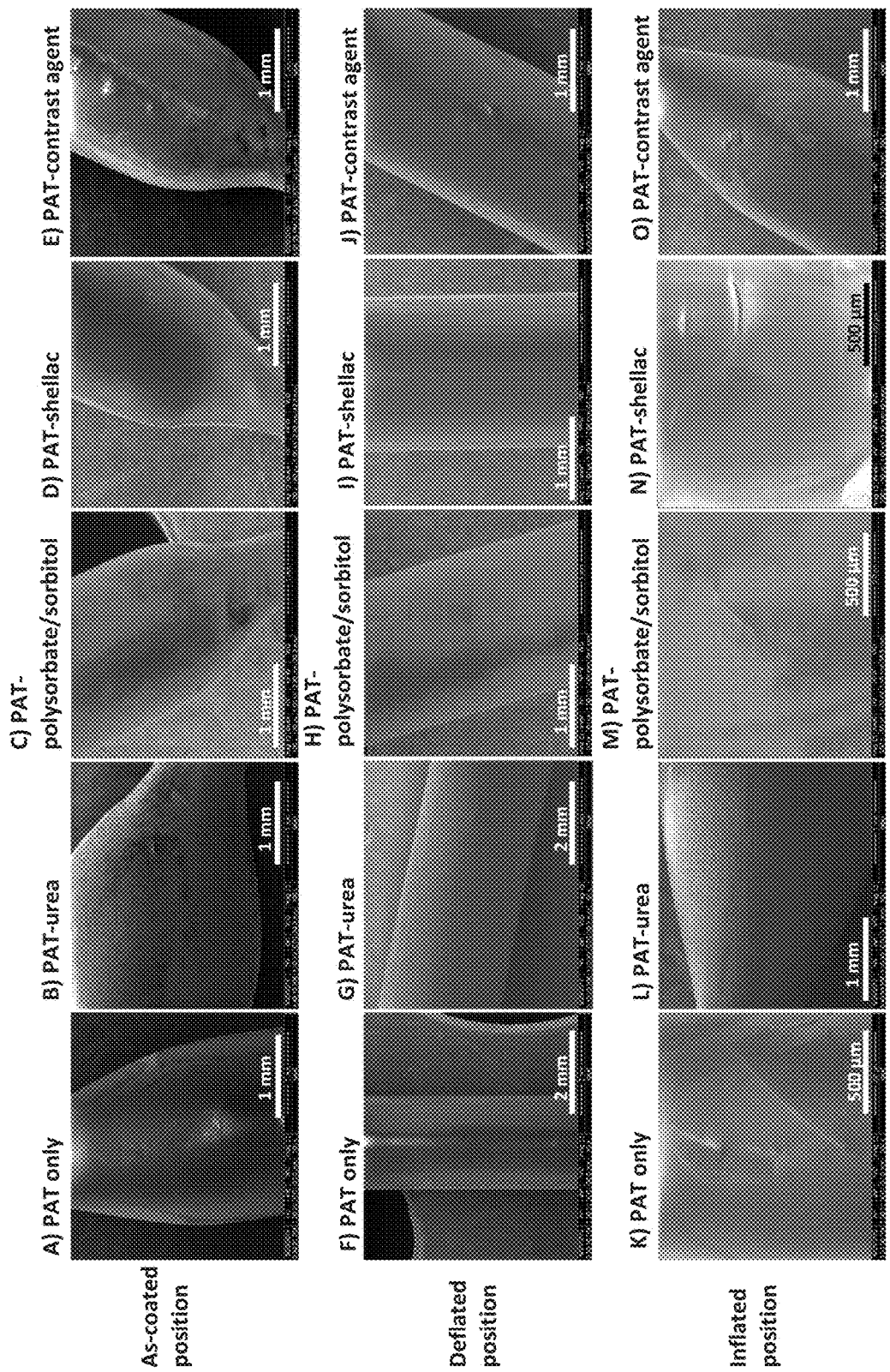

FIG. 18. SEM images of control drug-coated balloons prepared using PAT only (A, F, K), PAT-urea (B, G, L), PAT-polysorbate/sorbitol (C, H, M), PAT-shellac (D, I, N), and PAT-iodixanol (E, J, O).

Figure 19:
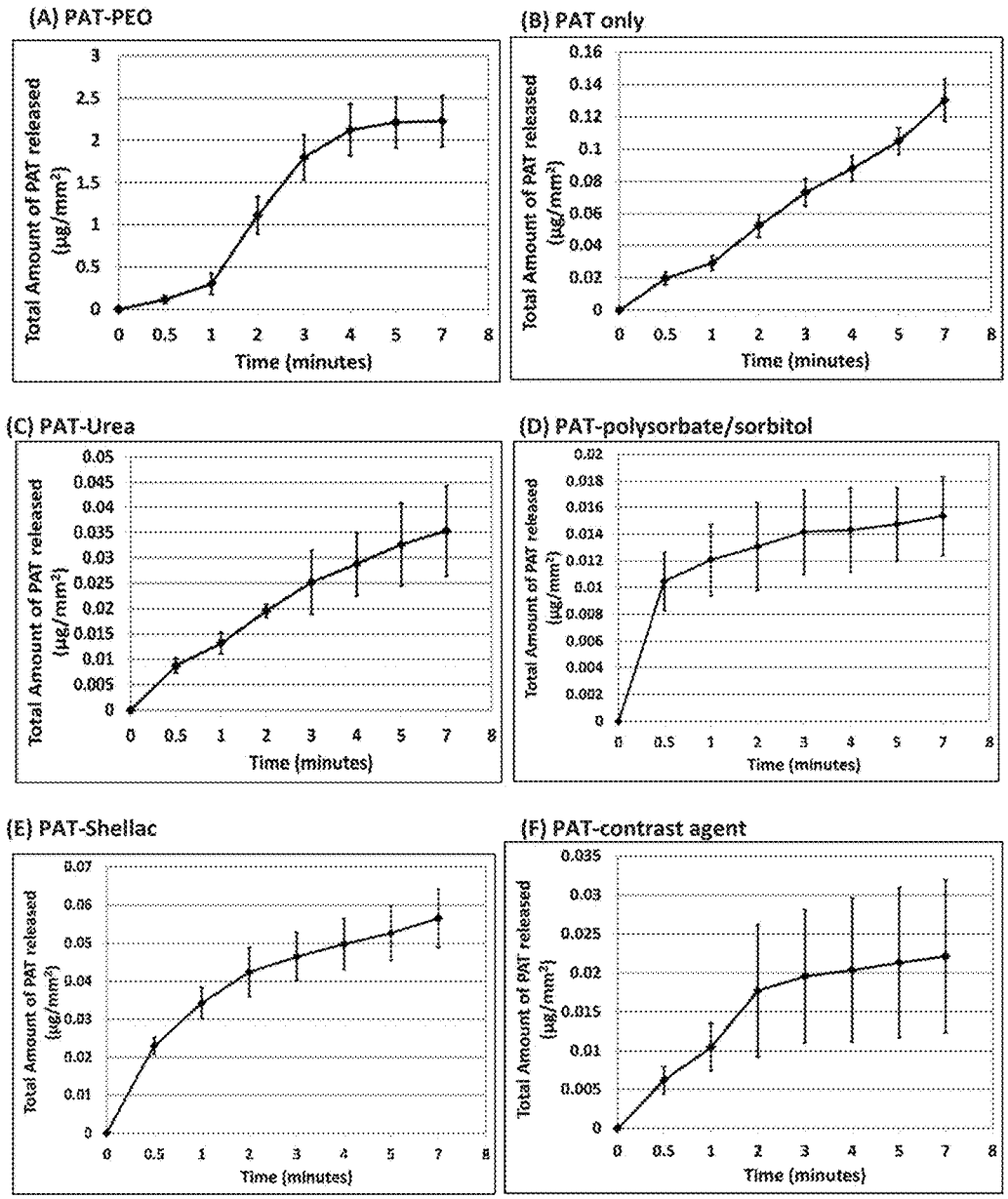

FIG. 19. Cumulative PAT released ($\mu m/mm^2$) from PAT-PEO coated balloons (A) and control drug-coated balloons (B, C, D, E, and, F).

Figure 20:
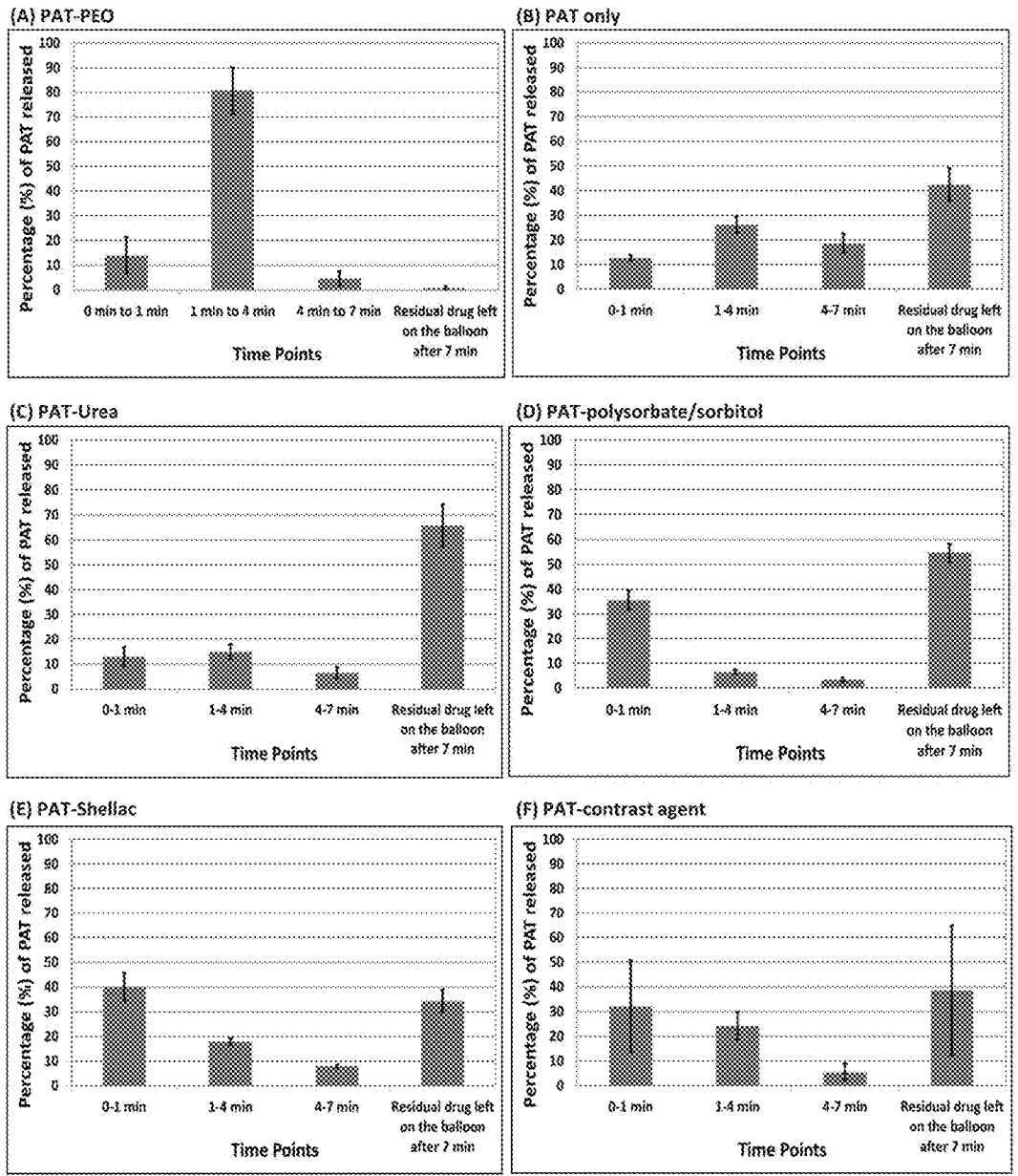

FIG. 20. Percentage of PAT released from PAT-PEO coated balloons (A) and control drug-coated balloons (B, C, D, E, and, F).

Figure 21:
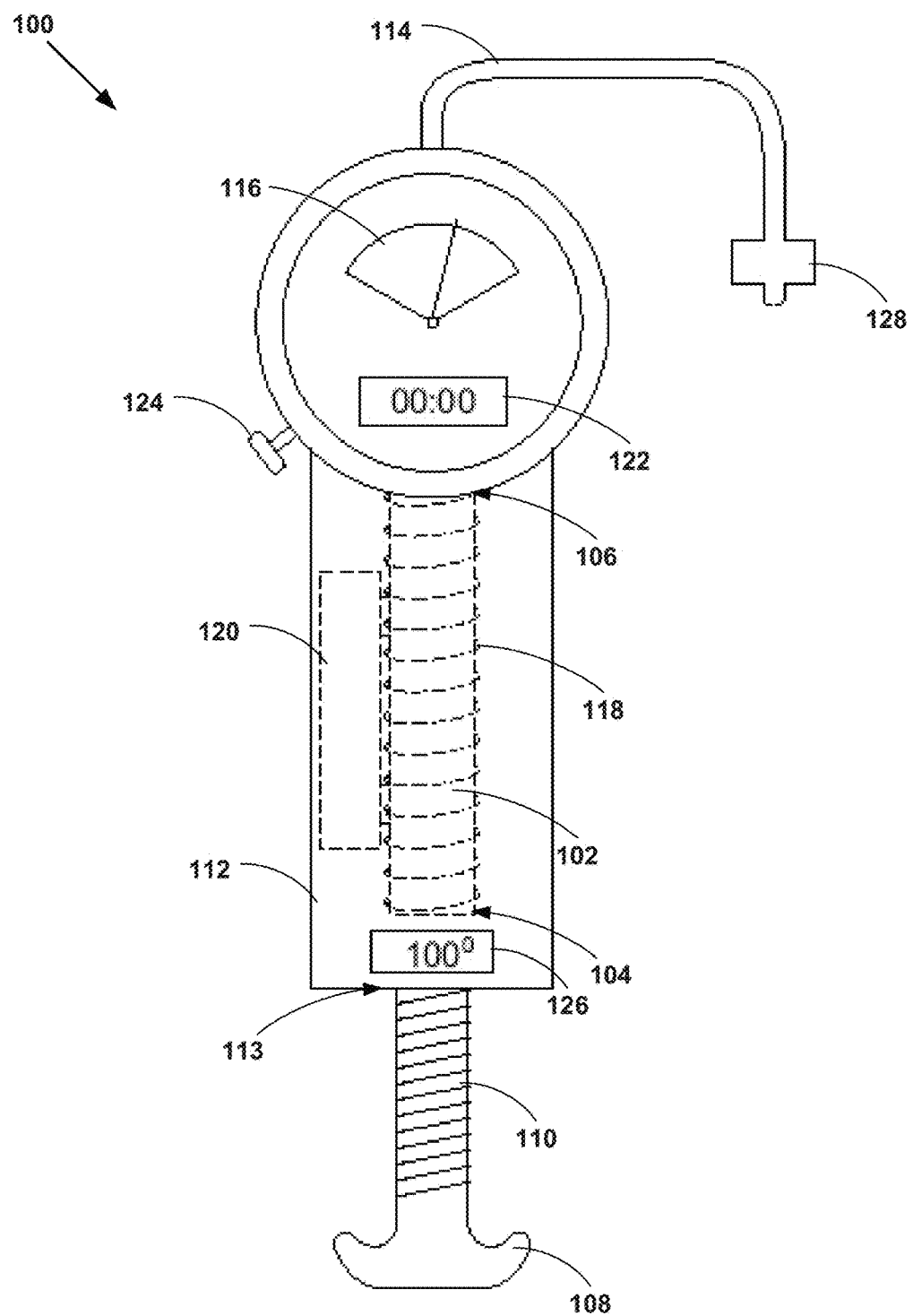

FIG. 21 illustrates a device used to inflate a drug delivery balloon, in accordance with one embodiment of the invention.

Figure 22:
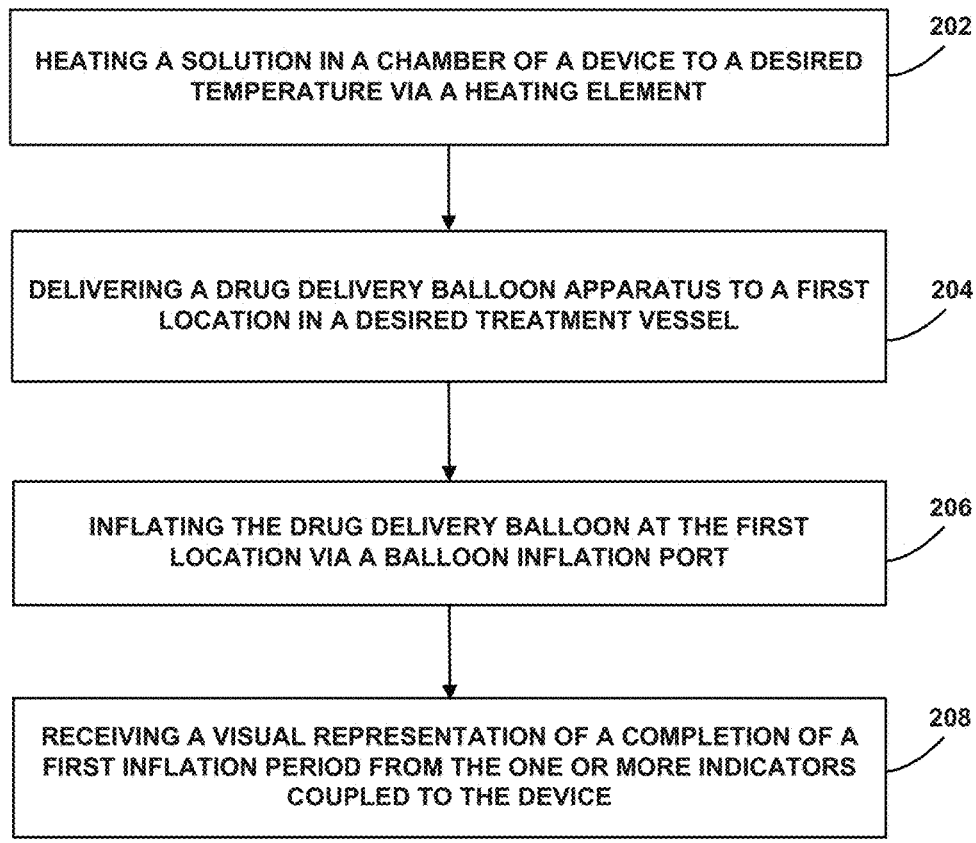

FIG. 22 is a flow chart depicting functions that can be carried out in accordance with example embodiments of the disclosed methods.

Figure 23:
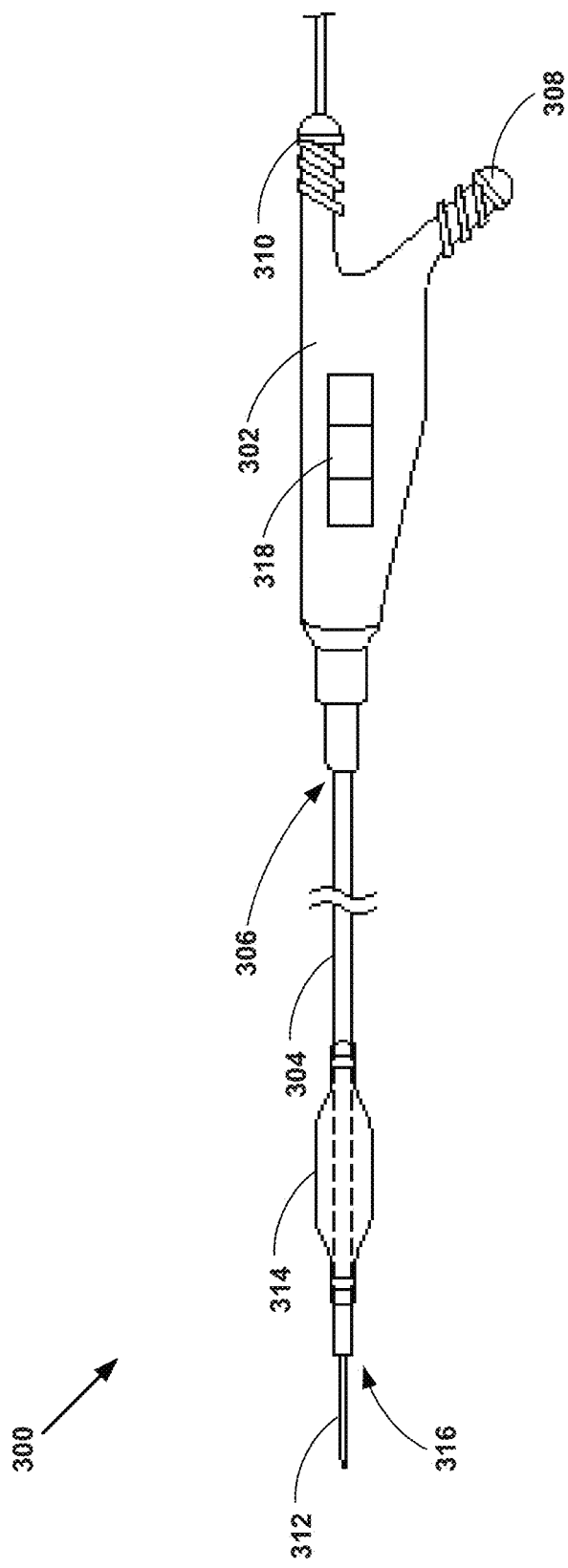

FIG. 23 illustrates a drug delivery balloon apparatus, in accordance with one embodiment of the invention.

Figure 24:
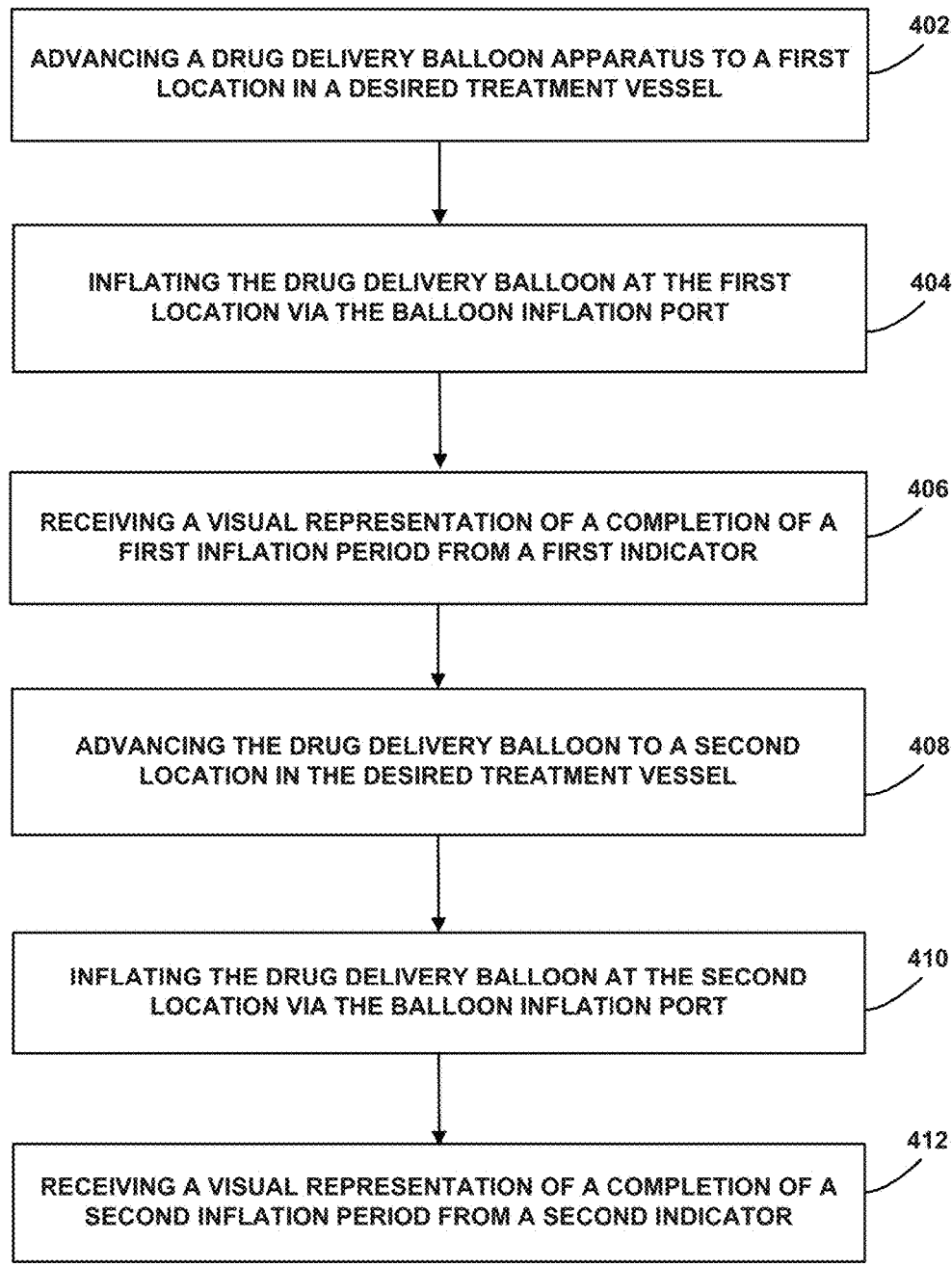

FIG. 24 is another flow chart depicting functions that can be carried out in accordance with example embodiments of the disclosed methods.

DETAILED DESCRIPTION OF THE INVENTION

As used herein and unless otherwise indicated, the terms "a" and "an" are taken to mean "one", "at least one" or "one or more". Unless otherwise required by context, singular terms used herein shall include pluralities and plural terms shall include the singular.

All scientific and technical terms used in this application have meanings commonly used in the art unless otherwise specified.

As used herein, "about" means+/−5% of the recited dimension or unit.

All embodiments of any aspect of the invention can be used in combination, unless the context clearly dictates otherwise.

In a first aspect, the invention provides formulations comprising:

a biocompatible hydrophilic polymer having a thickness of between about 1 μm and about 1 mm and an elastic modulus of between about 0.05 MPa and about 1000 MPa; and a therapeutic disposed within the hydrophilic polymer, wherein the polymer provides for release of about 0% to about 30% of the therapeutic within about 1 minute after introduction of the formulation into physiological conditions, and wherein the polymer provides for release of at least about 50% to about 100% of the therapeutic within about 20 minutes after introduction of the formulation into physiological conditions.

The inventors have surprisingly discovered that the formulations of the present invention can be used, for example, tailor drug release characteristics from a medical device, such as a drug-eluting balloon, in such a way that drug loss can be minimized or prevented during the passage of the device (for example, before inflating a balloon at a diseased site) and then, a significant amount of drug can be delivered at the targeted diseased site during a short time of deployment (such as the time of balloon inflation at the diseased site). Thus, the invention provides a significant improvement over prior formulations used to control release of therapeutic from a drug-eluting devices such as drug-eluting balloons.

As used herein, a "therapeutic" is any compound that can provide a therapeutic benefit, (other than the polymer in which the therapeutic is disposed).

As used herein, "physiological conditions" mean deployment of the formulation in vivo (i.e.: the formulation coated on, for example, a medical device, and deployed into a target vessel), or simulated physiological conditions in vitro, such as immersion into a saline solution that approximates physiological saline. In one embodiment, simulated physiological conditions in vitro comprise immersion in a phosphate-buffered saline (PBS) solution such as those disclosed in the examples that follow.

The formulations of the invention comprise a biocompatible hydrophilic polymer having a thickness of between about 1 μm and about 1 mm and an elastic modulus of between about 0.05 MPa and about 1000 MPa. In one embodiment, the polymer is not cross-linked; in another embodiment, the polymer is cross-linked. The polymers are hydrophilic, and thus when exposed to physiological conditions begin to break down, thus releasing the therapeutic disposed within the formulation (i.e., the therapeutic is primarily within the formulation). By varying the thickness and composition of the polymers, the polymer releases the therapeutic at a controlled rate within the recited ranges. The polymer may comprise a single polymer layer or multiple polymer layers where each layer may comprise the same polymer and polymer concentration, or they layers may differ in polymer composition and/or concentration. In various embodiments, the polymer may be between about 1 μm and about 1 mm, about 10 μm and about 1 mm, about 25 μm and about 1 mm, about 50 μm and about 1 mm, about 1 μm and about 750 μm, about 10 μm and about 750 μm, about 25 μm and about 750 μm, about 50 μm and about 750 μm, about 1 μm and about 500 μm, about 10 μm and about 500 μm, about 25 μm and about 500 μm, about 50 μm and about 500 μm, about 1 μm and about 200 μm, about 5 μm and about 200 μm, about 10 μm and about 200 μm, about 20 μm and about 200 μm, about 25 μm and about 200 μm, about 50 μm and about 200 μm, about 75 μm and about 200 μm, and about 100 μm and about 200 μm. The thickness of the polymer may be, for example, appropriate for coating of balloons and subsequent folding of balloons to facilitate loading of the coated balloon into a balloon catheter for subsequent delivery to a patient.

The elastic modulus of the polymer is between about 0.05 MPa and about 1000 MPa. As is known to those of skill in the art, the "elastic modulus" is the measure of stiffness or rigidity of a material. The elastic modulus of the polymers may be, for example, no greater than the elastic module of a balloon on which it is to be coated, thus permitting the balloon to inflate, and is great enough to permit the formulation to remain adhered to a medical device on which it is coated, such as a balloon. The elastic modulus will vary depending on the polymer employed; it is well within the level of those of skill in the art to choose a polymer with an appropriate elastic modulus based on the teachings herein. In various embodiments, the polymer elastic modulus may range between about 0.3 MPa and about 1000 MPa, about 0.3 MPa and about 800 MPa, about 0.3 MPa and about 600 MPa, or about 0.3 MPa and about 485 MPa.

The formulations of the present invention provide for release of about 1% to about 30% the therapeutic within about 1 minute after introduction of the formulation into physiological conditions, and release of at least about 50% to about 100% of the therapeutic within about 20 minutes after introduction of the formulation into physiological conditions. As used herein, "provides for" means that once placed in physiological conditions, the formulation releases the recited percentage of therapeutic.

In various embodiments, the formulations provide for release within about 1 minute after introduction of the formulation into physiological conditions of:
about 1% to about 30% the therapeutic,
about 1% to about 25% the therapeutic,
about 1% to about 20% the therapeutic,
about 1% to about 15% the therapeutic,
about 1% to about 10% the therapeutic,
about 1% to about 5% the therapeutic,
about 1% to about 2.5% the therapeutic,
about 5% to about 30% the therapeutic,
about 5% to about 25% the therapeutic,
about 5% to about 20% the therapeutic,
about 5% to about 15% the therapeutic,
about 5% to about 10% the therapeutic,
about 10% to about 30% the therapeutic,
about 10% to about 25% the therapeutic,
about 10% to about 20% the therapeutic, or
about 10% to about 15% the therapeutic.

For treatments using drug-coated balloons, the typical balloon tracking time (deployment to diseased site) is from 30 seconds to 1 minute. Thus, the formulations of the invention minimize therapeutic loss from the formulation during this tracking period, thus conserving therapeutic to be released at the diseased site.

In various further embodiments, the formulations provide for release of at least about 50% to about 100% of the therapeutic within about 20, 19, 18, 17, 16, 15, 14, 13, 12, 11, 10, 9, 8, 7, 6, 5, or 4 minutes after introduction of the formulation into physiological conditions. In other embodiments, the formulations provide for release of at least about 50% to about 95%, about 50% to about 90%, about 50% to about 85%, about 50% to about 80%, about 50% to about 75%, about 50% to about 70%, about 50% to about 65%, or about 50% to about 60%, about 60% to about 100%, about 60% to about 95%, about 60% to about 90%, about 60% to about 85%, about 60% to about 80%, about 60% to about 75%, about 60% to about 70%, about 70% to about 100%, about 70% to about 95%, about 70% to about 90%, about 70% to about 85%, or about 70% to about 80%, of the therapeutic within about 20, 19, 18, 17, 16, 15, 14, 13, 12, 11, 10, 9, 8, 7, 6, 5, or 4 minutes after introduction of the formulation into physiological conditions.

As disclosed herein, the formulations of the invention are useful for single-use or multiple use medical devices, such as balloon catheters. The typical time period of balloon inflation and treatment is approximately 3 minutes. Thus, in one embodiment for a single use (i.e.: balloon angioplasty at a single diseased vascular site), the tracking time is about 1 minute, and drug release occurs at the diseased site between 1-4 minutes after in vivo deployment of the balloon. In this embodiment, the polymer provides for release of at least about 50% to about 100% of the therapeutic within about 4 minutes after introduction of the formulation into physiological conditions. In other embodiments, the formulations provide for release of at least about 50% to about 95%, about 50% to about 90%, about 50% to about 85%, about 50% to about 80%, about 50% to about 75%, about 50% to about 70%, about 50% to about 65%, or about 50% to about 60%, about 60% to about 100%, about 60% to about 95%, about 60% to about 90%, about 60% to about 85%, about 60% to about 80%, about 60% to about 75%, about 60% to about 70%, about 70% to about 100%, about 70% to about 95%, about 70% to about 90%, about 70% to about 85%, or about 70% to about 80%, of the therapeutic within about 4 minutes after introduction of the formulation into physiological conditions.

For multiple uses (i.e.: two or more diseased sites), the time over which release is desired increases. For two diseased sites, the time over which release is desired is about 8 minutes total (i.e.: about 1 minute tracking and then 3 minutes for balloon inflation and active agent release at the first diseased site; then about 1 minute tracking to the second diseased site and 3 minutes for balloon inflation and active agent release at the second diseased site). In this embodiment, the polymer provides for release of at least about 50% to about 100% of the therapeutic within about 8 minutes after introduction of the formulation into physiological conditions. In other embodiments, the formulations provide for release of at least about 50% to about 95%, about 50% to about 90%, about 50% to about 85%, about 50% to about 80%, about 50% to about 75%, about 50% to about 70%, about 50% to about 65%, or about 50% to about 60%, about 60% to about 100%, about 60% to about 95%, about 60% to about 90%, about 60% to about 85%, about 60% to about 80%, about 60% to about 75%, about 60% to about 70%, about 70% to about 100%, about 70% to about 95%, about 70% to about 90%, about 70% to about 85%, or about 70% to about 80%, of the therapeutic within about 8 minutes after introduction of the formulation into physiological conditions.

Similarly, for three diseased sites, the time over which release is desired is about 12 minutes total (i.e.: about 1 minute tracking and then 3 minutes for balloon inflation at each diseased site). In this embodiment, the polymer provides for release of at least about 50% to about 100% of the therapeutic within about 12 minutes after introduction of the formulation into physiological conditions. In other embodiments, the formulations provide for release of at least about 50% to about 95%, about 50% to about 90%, about 50% to about 85%, about 50% to about 80%, about 50% to about 75%, about 50% to about 70%, about 50% to about 65%, or about 50% to about 60%, about 60% to about 100%, about 60% to about 95%, about 60% to about 90%, about 60% to about 85%, about 60% to about 80%, about 60% to about 75%, about 60% to about 70%, about 70% to about 100%, about 70% to about 95%, about 70% to about 90%, about 70% to about 85%, or about 70% to about 80%, of the therapeutic within about 12 minutes after introduction of the formulation into physiological conditions.

It is well within the level of skill in the art to determine other appropriate release profiles in light of all circumstances (actual expected tracking time, inflation/release time that may differ from those described here), based on the teachings of the present invention. The arteries such as iliac artery, femoral artery, popliteal artery, tibial artery, and peroneal artery are found at different locations of the lower extremity. Hence, the time needed (in minutes) to advance a balloon catheter to the different arteries in the lower extremity may be different. The formulations disclosed herein are capable of carrying drug and releasing significant amount of drug at various time intervals, for example, between 1 to 20 minutes, or ranges therebetween. Such a control in drug release from balloons will aid clinicians in choosing appropriate drug-coated balloons for the arteries for a particular treatment.

As disclosed in the examples that follow, other drug-eluting balloons (DEBs) were compared with balloons coated with the formulations of the present invention for ability to release the therapeutic within 4 minutes (i.e.: single use). As demonstrated therein, paclitaxel release from other drug-eluting balloons was significantly less desirable from balloons coated with the formulations of the invention, with the other DEBs releasing a much larger percentage of the loaded paclitaxel during the first 1 minute (tracking period) and/or retaining a much higher percentage of paclitaxel after the therapeutic window of 4 minutes for balloon inflation and drug release. Thus, the formulations of the present invention clearly provide a significant improvement over prior formulations for use in, for example, drug-eluting balloons.

In one embodiment, the release of active agent from the formulation is measured using high performance liquid chromatography (HPLC), such as via the methods described in the examples that follow.

Any suitable hydrophilic polymer can be used in the formulations of the present invention. In one embodiment, the polymer comprises poly(ethylene oxide) (PEO), heparin, dextran, dextran sulfate (DS), polyethylene glycol (PEG), butyryl trihexyl citrate (BTC), heparin sulfate (HS), hyaluronic acid (HA), chondroitin sulfate (CS), or combinations thereof. The polymer may be present at any suitable concentration in the formulation to provide for a polymer with the desired thickness. In one embodiment, the polymer is present at a concentration of between about 1 $\mu g/mm^2$ and about 2000 $\mu g/mm^2$. In various non-limiting embodiments, the polymer is present at a concentration of between about 1 $\mu g/mm^2$ and about 1500 $\mu g/mm^2$, about 1 $\mu g/mm^2$ and about 1000 $\mu g/mm^2$, about 1 $\mu g/mm^2$ and about 750 $\mu g/mm^2$, about 1 $\mu g/mm^2$ and about 500 $\mu g/mm^2$, 10 $\mu g/mm^2$ and about 2000 $\mu g/mm^2$, 10 $\mu g/mm^2$ and about 1500 $\mu g/mm^2$, about 10 $\mu g/mm^2$ and about 1000 $\mu g/mm^2$, about 10 $\mu g/mm^2$ and about 750 $\mu g/mm^2$, about 10 $\mu g/mm^2$ and about 500 $\mu g/mm^2$, about 25 $\mu g/mm^2$ and about 2000 $\mu g/mm^2$, about 25 $\mu g/mm^2$ and about 1500 $\mu g/mm^2$, about 25 $\mu g/mm^2$ and about 1000 $\mu g/mm^2$, about 25 $\mu g/mm^2$ and about 750 $\mu g/mm^2$, or about 25 $\mu g/mm^2$ and about 500 $\mu g/mm^2$.

In one embodiment, the polymer comprises PEO. In one embodiment, the PEO has an average molecular weight range of between about 100 Da and about 10,000,000 Da. In various further embodiments, the PEO may have an average molecular weight range of between about 5,000 Da and about 10,000,000 Da, about 5,000 Da and about 5,000,000 Da, about 5,000 Da and about 1,000,000 Da, about 5,000 Da and about 500,000 Da, about 5,000 Da and about 200,000 Da, about 5,000 Da and about 100,000 Da, about 25,000 Da and about 10,000,000 Da, about 25,000 Da and about 5,000,000 Da, about 25,000 Da and about 1,000,000 Da, about 25,000 Da and about 500,000 Da, about 25,000 Da and about 200,000 Da, about 25,000 Da and about 100,000 Da, about 50,000 Da and about 10,000,000 Da, about 50,000 Da and about 5,000,000 Da, about 50,000 Da and about 1,000,000 Da, about 50,000 Da and about 500,000 Da, about 50,000 Da and about 200,000 Da, about 50,000 Da and about 150,000 Da, or about 100,000 Da.

In various further embodiments of the PEO polymer-based formulations, 1, 2, 3, or all 4 of the following are true:

(a) the elastic modulus is between about 308 MPa and about 485 MPa;

(b) the formulation possesses a strain at break of between about 2.3% and about 4.2%; and (c) the formulation possesses a tensile strength of between about 4.1 MPa and about 7.4 MPa.

As described in the examples that follow, exemplary PEO polymer-based formulations described therein possess these properties.

In another embodiment, the polymer comprises DS. In one embodiment, the DS has an average molecular weight of between about 100,000 Da and about 1,000,000 Da. In various further embodiments, the DS has an average molecular weight of between about 200,000 Da and about 1,000,000 Da, about 300,000 Da and about 1,000,000 Da, about 400,000 Da and about 1,000,000 Da, or about 500,000 Da and about 1,000,000 Da.

In various further embodiments of the DS polymer-based formulations, 1, 2, or all 3 of the following are true:

(a) the elastic modulus is between about 0.34 MPa and about 5.7 MPa;

(b) the formulation possesses a strain at break of between about 347% and about 490%; and (c) the formulation possesses a tensile strength of between about 0.10 MPa and about 0.5 MPa.

As described in the examples that follow, exemplary DS polymer-based formulations described therein possess these properties.

Figure 1:
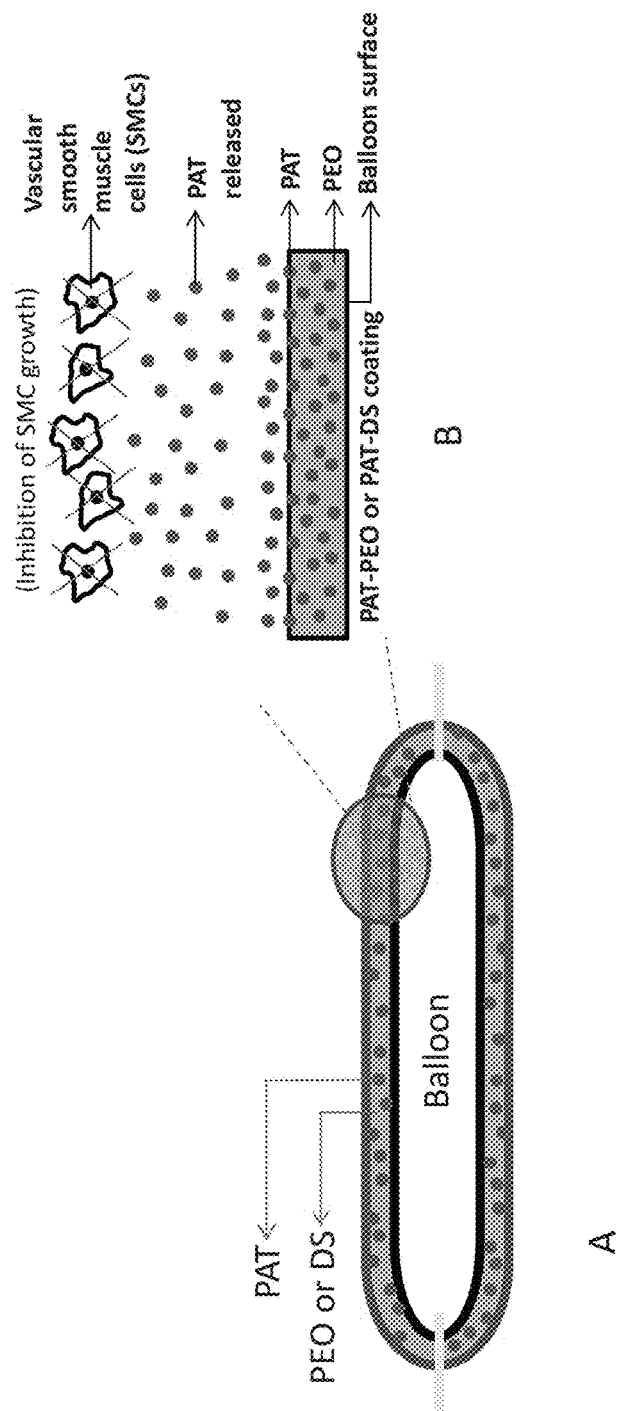
FIG. 1 is a drawing of a single-use embodiment of the formulations of the invention coated on a balloon. (A)

In one embodiment, the polymer comprises a single polymer layer, and the polymer provides for release of about 1% to about 30% of the therapeutic within about one minute after introduction of the formulation into physiological conditions, and release of at least about 50% to about 100% of the therapeutic within 4-12 minutes after introduction of the formulation into physiological conditions. This embodiment can be used in single use devices or multiple use devices (such as balloons coated with the formulations; see FIG. 1). By increasing the polymer layer thickness (i.e., increasing the polymer concentration increases the resulting polymer thickness), the release time is correspondingly increased. Thus, in one embodiment, the single polymer layer thickness is between about 10 µm and about 500 µm. In other embodiments, the single polymer thickness is between about 50 µm and about 500 µm, about 100 µm and about 500 µm, about 150 µm and about 500 µm, about 10 µm and about 400 µm, about 50 µm and about 400 µm, about 100 µm and about 400 µm, about 150 µm and about 400 µm, about 10 µm and about 300 µm, about 50 µm and about 300 µm, about 100 µm and about 300 µm, about 150 µm and about 300 µm, about 10 µm and about 200 µm, about 50 µm and about 200 µm, about 100 µm and about 200 µm, or about 150 µm and about 200 µm. In various further embodiments, the single layer provides for release of at least about 50% to about 100% of the therapeutic within 4, 5, 6, 7, 8, 9, 10, 11, or 12 minutes. In various further embodiments, the single layer polymer provides for release of about 50% to about 95%, about 50% to about 90%, about 50% to about 85%, about 50% to about 80%, about 50% to about 75%, about 50% to about 70%, about 50% to about 65%, or about 50% to about 60%, about 60% to about 100%, about 60% to about 95%, about 60% to about 90%, about 60% to about 85%, about 60% to about 80%, about 60% to about 75%, about 60% to about 70%, about 70% to about 100%, about 70% to about 95%, about 70% to about 90%, about 70% to about 85%, or about 70% to about 80%, of the therapeutic within 4, 5, 6, 7, 8, 9, 10, 11, or 12 minutes after introduction of the formulation into physiological conditions.

Alternatively, the formulations may comprise a plurality of polymer layers (see FIG. 2). In one embodiment, the plurality of polymer layers comprise at least a first polymer layer and a second polymer layer, wherein the first polymer layer provides for release of about 10% to about 60% of the therapeutic within about 4 minutes after introduction of the formulation into physiological conditions, and the second polymer layer provides for release of at least about another 10% to about 60% of the therapeutic within 8 minutes after introduction of the formulation into physiological conditions. In a further embodiment, the polymer further comprises a third polymer layer, wherein the third polymer layer provides for release of at least about another about 10% to about 60% of the therapeutic within about 12 minutes after introduction of the formulation into physiological conditions.

Each polymer layer may comprise the same or different polymers, at the same or different concentrations and thicknesses. If the polymer layers are the same, then each layer may be the same thickness, since diffusion of the therapeutic from the innermost layer will be delayed due to its position under the second layer (and third payer when present). Thus, this embodiment permits easier preparation of the formulation, since the same liquid formulation can be used to coat a medical device of interest (such as a balloon) multiple times to achieve the multiple layer embodiment of the formulation. Alternatively, the release profile can be further modified by including layers of different polymer concentration and/or composition. Based on the teachings herein, it is well within the level of those of skill in the art to prepare multiple layer embodiments of the formulations of the invention suitable for an intended purpose.

In another embodiment of any embodiment of the invention, the formulation further comprises an inert polymer layer. The inert polymer layer may be present atop the polymer in a single polymer layer embodiment (for example, to limit burst release that might occur during the tracking period), or between polymer layers (i.e.: between the first and second polymer layer, and/or between the second and third polymer layer (when present), etc.) in the multiple polymer layer embodiments. As used herein, and "inert" polymer layer is a polymer layer that does not include a therapeutic. The inert polymer may be any suitable biocompatible hydrophilic polymer. In various embodiments, the inert polymer layer may comprise poly(ethylene oxide) (PEO), heparin, dextran, dextran sulfate (DS), polyethylene glycol (PEG), butyryl trihexyl citrate (BTC), heparin sulfate (HS), hyaluronic acid (HA), chondroitin sulfate (CS), or combinations thereof. The inert polymer may be the same or different than the polymers layers it is atop or between. In specific embodiments, the inert polymer layer comprises PEO or DS, or a combination thereof. The insert layer may be any suitable thickness for an intended purpose. In one embodiment, the inert layer is between about 0.1 um and about 50 um in thickness. In various other embodiments, the inert layer may be between about 0.1 um and about 40 um, about 1 um and about 50 um, about 0.1 um and about 30 um, about 0.1 um and about 20 um, about 1 um and about 20 um, and about 6 um and about 35 um.

In a further embodiment, the inert layer and/or the polymer with therapeutic may comprise an excipient, which may help the therapeutic (when released from the polymer) to penetrate into the vascular wall at the diseased site (when used in conjunction with a balloon). Any suitable excipient may be used, including but not limited to iopromide, butyryl trihexyl citrate, shellac resin, aleuritic acid, polysorbate, sorbitol, urea, phospholipid based material, genistein, dimethyl sulfoxide, acetyltriethyl citrate, and lecithin.

In another embodiment, the polymer may further comprise a plasticizer. Any suitable plasticizer may be used, including but not limited to hydrophilic materials such as glycerol, ethylene glycol, diethylene glycol, triethylene glycol, tetraethylene glycol, polyethylene glycol, polyethylene glycol monomethyl ether, propylene glycol, sorbitol sorbitan solution, mannitol, xylitol, ethanolamine, urea, triethanolamine, and their derivatives; hydrophobic materials such as alkyl citrates, acetyl tributyl citrate, acetyl triethyl citrate, castor oil, diacetylated monoglycerides, dibutyl sebacate, diethyl phthalate, triacetin, tributyl citrate, triethyl citrate, and their derivative; acids such as acetic acid, formic acid, glycolic acid, L-lactic acid, D-lactic acid, D,L-lactic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, 5-hydroxyhexanoate, ε-caprolactone, 6-hydroxycaproic acid, γ-butyrolactone, β-butyrolactone, and their derivatives; alcohols such as 1-butanol, 2-butanol, ethanol, 2-methyl-1-butanol, 2-methyl-1-propanol, 1-pentanol, 1-propanol, 2-propanol, and their derivatives; esters such as ethyl acetate, ethyl formate, isopropyl acetate, methyl acetate, propyl acetate, phosphate ester, phthalic ester, and their derivatives; ethers such as anisole, tert-butylmethyl ether, ethyl ether, and their derivatives; hydrocarbons such as cumene, heptane, pentane, and their derivatives; ketones such as acetone, methylethyl ketone, methylisobutyl ketone and their derivatives, and others such as dimethyl sulfoxide, acetylated monoglycerides, trioctyl trimellitate, azelate, and their derivatives. Any suitable amount of plasticizer can be used as deemed appropriate for an intended use of the formulations. In one embodiment, the plasticier can be present in the polymer at 1 wt/wt % to 100 wt/wt %, or between about 1 wt/wt % and about 50 wt/wt %, about 1 wt/wt % and about 25 wt/wt %, about 1 wt/wt % to 15 wt/wt %, about 20 wt/wt %, about 15 wt/wt %, about 10 wt/wt %, about 5 wt/wt %, or about 1 wt/wt %.

In a second aspect, the invention provides formulations comprising poly(ethylene oxide) (PEO) having (a) a thickness of between about 1 μm and about 1 mm; (b) an average molecular weight range of between about 50,000 and about 200,000; and (c) an elastic modulus of between about 0.05 MPa and about 1000 MPa; and an therapeutic disposed within the PEO.

In a third aspect, the invention provides formulations comprising dextran sulfate (DS) having (a) a thickness of between about 1 μm and about 1 mm; (b) an average molecular weight range of between about 100,000 and about 1,000,000; and (c) an elastic modulus of between about 0.05 MPa and about 1000 MPa; and an therapeutic disposed within the DS.

All embodiments of the first aspect can be combined with the PEO-based formulations of this second aspect of the invention and the DS-based formulations of the third aspect of the invention.

Any suitable therapeutic can be disposed within the polymer as is appropriate for a given intended use. The therapeutic may be present in any amount suitable in light of the polymer used, the thickness of the polymer, the concentration of the polymer, the specific therapeutic, and the intended use. In one embodiment, the therapeutic comprises one or more compounds selected from the group consisting of alkylating agents, angiogenesis inhibitors, antibodies, antimetabolites, antimitotics, antiproliferatives, aurora kinase inhibitors, apoptosis promoters, activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, growth factor inhibitors, heat shock protein (HSP)-90 inhibitors, demethylating agents, histone deacetylase (HDAC) inhibitors, hormonal therapies, immunologicals, inhibitors of apoptosis proteins (IAPB) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteasome inhibitors, purine analogs, pyrimidine analogs, receptor tyrosine kinase inhibitors, retinoids/deltoids plant alkaloids, small inhibitory ribonucleic acids (siRNAs), and topoisomerase inhibitors, and derivatives and combinations thereof.

In specific embodiments, the therapeutic may comprise one or more compound selected from the group consisting of: docetaxel, doxorubicin, irinotecan, paclitaxel, paclitaxel albumin bound particles, doxorubicin HCL liposome, adecatumumab, blinatumomab, siRNA-based therapeutics, altretamine, apaziquone, bendamustine, brostallicin, busulfan, carboquone, carmustine (BCNU), chlorambucil, laromustine, cyclophosphamide, dacarbazine, decitabine, 5'-azacytidine, estramustine, fotemustine, glufosfamide, ifosfamide, lomustine (CCNU), mafosfamide, melphalan, mitobronitol, mitolactol, nimustine, nitrogen mustard N-oxide, ranimustine, temozolomide, thiotepa, bendamustine, treosulfan, rofosfamide; endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors; pemetrexed disodium, 5-azacitidine, capecitabine, carmofur, cladribine, clofarabine, cytarabine, cytarabine ocfosfate, cytosine arabinoside, decitabine, deferoxamine, doxifluridine, eflornithine, EICAR (5-ethynyl-1-.beta.-D-ribofuranosylimidazole-4-carboxamide), enocitabine, ethnylcytidine, fludarabine, 5-fluorouracil alone or in combination with leucovorin, gemcitabine, hydroxyurea, melphalan, mercaptopurine, 6-mercaptopurine riboside, methotrexate, trimetrexate, pralatraxate, mycophenolic acid, nelarabine, nolatrexed, ocfosfate, pelitrexol, pentostatin, raltitrexed, Ribavirin, triapine, trimetrexate, S-1, tiazofurin, tegafur, vidarabine; AT-101 ((−)gossypol), Bcl-2-targeting antisense oligonucleotide, Bcl-xL inhibitors, Bcl-w inhibitors, Bfl-1 inhibitors, N-(4-(4-(((4'-chloro(1,1'-biphenyl)-2-yl)methyl)piperazin-1-yl)benzoyl)-4-((((1R)-3-(dimethylamino)-1-((phenylsulfanyl)methyl)propyl)amino)-3-nitrobe-nzenesulfonamide) (ABT-737), N-(4-(4-((2-(4-chlorophenyl)-5,5-dimethyl-1-cyclohex-1-en-1-yl)methyl)pip-erazin-1-yl)benzoyl)-4-(((1R)-3-(morpholin-4-yl)-1-((phenylsulfanyl)methyl-)propyl)amino)-3-((trifluoromethyl)sulfonyl) benzenesulfonamide (ABT-263), GX-070 (obatoclax); Bcr-Abl kinase inhibitors, imatinib; CDK inhibitors, flavopyridol, seliciclib; EGFR inhibitors, anti-EGFR immunoliposomes, EGF-vaccine, cetuximab, IgA antibodies, gefitinib, erlotinib EGFR fusion protein, lapatinib; ErbB2 receptor inhibitors, canertinib, trastuzumab, lapatinib, petuzumab, ionafarnib, HER2 vaccines, nti-HER/2neu bispecific or trispecific antibodies; histone deacetylase inhibitors, romidepsin, trapoxin, suberoylanilide hydroxamic acid (SAHA), valproic acid; HSP-90 inhibitors, geldanamycin-human recombinant antibody to HSP-90, radicicol; activators of death receptor pathways, Apomab, conatumumab, lexatumumab, trastuzumab; platinum chemotherapeutics, cisplatin, oxaliplatin eptaplatin, lobaplatin, nedaplatin, carboplatin, satraplatin, picoplatin; VEGFR inhibitors including bevacizumab, axitinib pegaptamib, sorafenib, pazopanib, vatalanib sunitinib, vandetanib; topoisomerase inhibitors, aclarubicin, 9-aminocamptothecin, amonafide, amsacrine, becatecarin, belotecan, irinotecan hydrochloride, camptothecin, dexrazoxine, diflomotecan, edotecarin, epirubicin, etoposide, exatecan, abraxane, irenotecan, 10-hydroxycamptothecin, gimatecan, lurtotecan, mitoxantrone, orathecin, pirarbucin, pixantrone, rubitecan, sobuzoxane, SN-38, tafluposide, topotecan; bevacizumab, CD40-specific antibodies, denosumab, cetuximab, zanolimumab, lintuzumab, edrecolomab, rituximab, ticilimumab, trastuzimab; anastrozole, exemestane, arzoxifene, bicalutamide, cetrorelix, degarelix, deslorelin, trilostane, dexamethasone, flutamide, raloxifene, fadrozole, toremifene, fulvestrant, letrozole, formestane, glucocorticoids, doxercalciferol, sevelamer carbonate, lasofoxifene, leuprolide acetate, megesterol, mifepristone, nilutamide, tamoxifen citrate, abarelix, prednisone, finasteride, rilostane, buserelin, luteinizing hormone releasing hormone (LHRH)), trilostane, modrastanefosrelin, goserelin; interferon alpha, interferon alpha-2a, interferon alpha-2b, interferon beta, interferon gamma-1a, interferon gamma-1b, interferon gamma-n1.; IFN-alpha), oxidized glutathione, tasonermin, tositumomab, alemtuzumab, cytotoxic lymphocyte antigen 4, decarbazine, denileukin, epratuzumab, lenograstim, lentinan, leukocyte alpha interferon, imiquimod, anti-CTLA-4, melanoma vaccine, mitumomab, molgramostim, gemtuzumab ozogamicin, filgrastim, oregovomab, pemtumomab sipuleucel-T, sargaramostim, sizofilan, teceleukin, ubenimex, Tetrachlorodecaoxide (TCDOaldesleukinthymalfasin, daclizumab, 90Y-Ibritumomab tiuxetan; ofatumumab; biological response modifiers agents including krestin, lentinan, sizofuran, picibanil, ubenimex; pyrimidine analogs include cytarabine (ara C or Arabinoside C), cytosine arabinoside, doxifluridine, fludarabine, 5-FU (5-fluorouracil), floxuridine, gemcitabine, ratitrexed, triacetyluridine troxacitabine; purine analogs including thioguanine and mercaptopurine; antimitotic agents including batabulin, epothilone D, N-(2-((4-hydroxyphenyl)amino)pyridin-3-yl)-4-methoxybenzenesulfonamide, ixabepilone, docetaxel, patupilone, larotaxel, vinflunine, synthetic epothilone; and other chemotherapeutic agents such as lovastatin, poly I:poly C12U, exisulind, pamidronic acid, arglabin, L-asparaginase, atamestane (1-methyl-3,17-dione-androsta-1,4-diene), tazarotene, mitumomab, tumor necrosis factorcelmoleukin, histamine dihydrochloride, cyclophosphamide; hydroxydoxorubicinvincristine, prednisone, cyproterone acetate, cumbrestatin A4P, dacarbazine, dactinomycin, 5,6-dimethylxanthenone-4-acetic acid (DMXAA), eniluracil, squalamine lactate, exatecan mesylate, enzastaurin, epithilone B, halofuginone, histerelin, hydroxycarbamide, ibandronic acid, cintredekin besudotox, IL-13-pseudomonas exotoxin, interferon-alpha, interferon-gamma, mifamurtide, lonafarnib, 5,10-methylenetetrahydrofolate, miltefosine (hexadecylphosphocholine), trimetrexate glucuronate, pentostatin, rubitecan, pegaspargase, PEG Interferon A, phenoxodiol, procarbazine, rebimastat, catumaxomab, lenalidomide, efaproxiral, lanreotide, acitretin, staurosporine (talabostat, bexarotene, DHA-paclitaxel, canfosfamide, temilifene, temozolomide, tesmilifene, thalidomide, thymitaq (2-amino-3,4-dihydro-6-methyl-4-oxo-5-(4-pyridylthio) quinazoline dihydrochloride), bosentan, tretinoin (Retin-A), tetrandrine, arsenic trioxide, ukrain (derivative of alkaloids from the greater celandine plant), vitaxin (anti-alphavbeta3 antibody), motexafin gadolinium, atrasentan, paclitaxel poliglumex, trabectedin, dexrazoxane, zolendronic acid, crizotinib, zorubicin, sirolimus, limus family drugs, and combinations thereof.

In one embodiment, the therapeutic comprises paclitaxel and/or paclitaxel albumin bound particles. As will be understood by those of skill in the art, "paclitaxel" includes any version of paclitaxel, including solid and particulate forms, as well as paclitaxel injectable solutions (such as a solution wherein each mL contains 6 mg paclitaxel, 527 mg polyoxyl 35 castor oil, 49.7% (v/v) dehydrated alcohol, and 2 mg citric acid, sold by Hospira (Lake Forest, Ill.). In one embodiment, the paclitaxel and/or paclitaxel albumin bound particles are present in the formulation at about 0.1 µg/mm$^2$ to about 30 µg/mm$^2$; in various embodiments, the paclitaxel and/or paclitaxel albumin bound particles are present in the formulation at about 0.25 µg/mm$^2$ to about 30 µg/mm$^2$, about 0.5 µg/mm$^2$ to about 30 µg/mm$^2$; about 1 µg/mm$^2$ to about 30 µg/mm$^2$, about 0.1 µg/mm$^2$ to about 25 µg/mm$^2$, about 0.25 µg/mm$^2$ to about 25 µg/mm$^2$, about 0.5 µg/mm$^2$ to about 25 µg/mm$^2$; about 1 µg/mm$^2$ to about 25 µg/mm$^2$, about 0.1 µg/mm$^2$ to about 20 µg/mm$^2$, about 0.25 µg/mm$^2$ to about 20 µg/mm$^2$, about 0.5 µg/mm$^2$ to about 20 µg/mm$^2$; or about 1 µg/mm$^2$ to about 20 µg/mm$^2$.

In another aspect, the present invention provides medical devices comprising the formulation of any aspect, embodiment, or combination of embodiments of the invention disposed on a surface of the medical device. The medical device may be any suitable medical device from which it would be desirable to release drugs within the short time frames permitted by the formulations of the invention. In various embodiments, the medical device may be balloon catheters, drug-eluting stents, vascular grafts, heart valves, pacemakers, artificial heart, ventricular assist devices, cardiopulmonary bypass, orthopedic devices, fracture fixation devices, dental devices, neural devices, stent grafts, heart-lung machines, hemodialysis machines, ocular implants and devices, and cochlear implants and devices. As will be understood by those of skill in the art, the overall dimensions of the formulation (i.e.: length, etc.) on the device surface will be those that are appropriate for the medical device on which the formulation is to be disposed. The formulation may be present disposed on an outer surface, an inner surface, over the entirety, or over a portion of the medical device. The formulation adheres to the surface of the medical device and thus can be used to coat medical devices for implantation into a patient in need of the medical device and the therapeutic present within the formulation, including for use in methods of the invention disclosed herein.

In a particular embodiment, the medical device comprises a balloon portion of a balloon catheter. The formulation may be present across the entire outer surface of the balloon, or a portion thereof that is suitable to permit therapeutic release from the balloon when inflated at a diseased site within the vasculature of a patient. In a further specific embodiment, the polymer comprises a single layer of PEO, and wherein the thickness of the PEO layer is between about 50 µm and about 500 µm. In another specific embodiment, the polymer comprises a single layer of DS, and wherein the thickness of the DS layer is between about 50 µm and about 500 µm. In a further embodiment, the therapeutic comprises paclitaxel and/or paclitaxel albumin bound particles, alone or in combination with one or more other therapeutics. In each of these embodiments, the single polymer layer thickness may alternatively be any of those disclosed for the formulation embodiments disclosed herein, and the therapeutic may alternatively be any suitable therapeutic.

In all aspect and embodiments of the devices of the invention, it will be understood by those of skill in the art that additional components may be present to improve one or more properties of the resulting device for an intended use. The formulation may be disposed directly on the device surface, or may be disposed indirectly on the surface. For example, additional components may be present to further improve adherence of the formulations to the medical devices. Balloons (and other medical devices) are typically made up of hydrophobic materials. However, most balloons, for example, are coated (in whole or in part) with hydrophilic coating to reduce friction and to sustain lubricity for easy tracking into the blood vessel. The specific adhesive properties of the formulation may vary depending on the properties of the balloon (or other device) surface on which it is disposed. The balloon surface may be hydrophobic (without any hydrophilic coating) or hydrophilic (with a hydrophilic coating over the entire surface or any suitable portion thereof). In one embodiment, the device surface is hydrophobic (in whole or in part) and the device further comprises a coating comprising an adhesion promoter directly disposed on the surface, with the formulation disposed directly on the adhesion promoter, and indirectly (and possibly directly) also the surface (i.e.: the formulation may contact the surface indirectly via the adhesion promoter, and possibly directly if the adhesion promoter is only disposed on a portion of the device surface). In this embodiment, the adhesion promoter serves to improve (directly or indirectly) adhesion of the formulation to the device surface. Any suitable adhesion promoter can be used, including but not limited to poly(p-xylylene) polymers (such as PARYLENE®) used as moisture and dielectric barriers, organosilanes, and organotitanates. In another embodiment, the adhesion promoter comprises paclitaxel or particle-bound paclitaxel (without any polymer); paclitaxel is a hydrophobic compound but is highly adhesive to a number of different material surfaces, and thus may interact directly with the hydrophobic surface and the hydrophilic polymer in the formulation, thus promoting adhesion of the formulation to the surface. It will be understood by those of skill in the art that, in those embodiments in which paclitaxel is the therapeutic present in the formulation, it will help promote adherence of the formulation to the surface through paclitaxel-hydrophobic surface interactions.

In other embodiments, the device (such as a balloon) surface is hydrophilic (in whole or in part). In this embodiment, the adhesion promoter may comprise a hydrophilic polymer (without therapeutic); in various embodiments, the hydrophilic polymer may be PEO, DS, or any other suitable hydrophilic polymer. The polymer may further be cross-linked to provide more stability to the coating. In another embodiment, the biocompatible polymer in the formulation is negatively charged (such as PEO and/or DS), and a positively charged polymer or material can be present as an adhesion promoter on the device/balloon surface. This embodiment improves adhesion of the formulation to the device surface due to the electrostatic interactions between positively charged material and negatively charged polymer in the formulation. In this embodiment, the polymer adhesion promoter and the formulation can be deposited one over the other multiple times to build a multiple layer (i.e.: layer-by-layer approach, where the adhesion promoter can also act as an inert layer, as described herein). In another embodiment, albumin-bound paclitaxel may serve as the adhesion promoter; albumin-bound paclitaxel is a hydrophilic formulation, and can be applied this directly on the surface (hydrophobic or with a hydrophilic coating).

In another embodiment, the device (such as a balloon) surface can be treated with gas plasma (or other technique) to obtain a variety of surface functional groups (different types of surface chemistry), prior to application of the formulation. In this case, the formulation is either physically deposited due to secondary bonding interactions with the modified surface, or covalently attached (primary bonding) to the functionalized device (such as a balloon) surface to improve adhesion.

In another embodiment, the device/balloon surface can be roughened or textured to increase the surface area. The formulation is thus disposed on the roughened or texture surface to improve adhesion (i.e., increase surface area provides more sites for the attachment of formulation on the balloon surface).

In another embodiment, biodegradable metallic biomaterials including but not limited to magnesium, magnesium alloys, iron, iron alloys, or any other biodegradable metals can be coated on top of the formulation in whole or in part to provide enhanced stability to the formulation, and to make the formulation easier to handle. In a further embodiment, other metallic biomaterials including but not limited to titanium, stainless steel, and cobalt-chromium alloys can be coated on the top of the formulation in whole or in part to provide enhanced stability to the formulation, and to make the formulation easier to handle. These metallic biomaterials can be coated on the formulation in any suitable manner; in one embodiment, the coatings comprise different patterns (arrays) that not only to provide enhanced stability to the formulation and make the formulation easier to handle, but also may serve to further control and/or tailor the therapeutic release (as discussed for the formulation arrays above). Any suitable technique for depositing the metallic biomaterials can be used. In one embodiment sputter coating is used to deposit the metallic biomaterials to produce a very thin metallic biomaterial coating of nanometer thickness. As will be understood by those of skill in the art based on all of the teachings herein, these metallic biomaterial coatings may also serve as an inert layer (as defined herein) disposed atop the formulation.

In another embodiment, the medical device comprises an array of the formulation of aspect, embodiment, or combination of embodiments of the invention disposed on a surface of the medical device, wherein the array comprises:

one or more positions comprising a first formulation position; and one or more positions comprising a second formulation position;

wherein the first formulation position provides for release of about 10% to about 60% of the therapeutic within about 4 minutes after introduction of the formulation into physiological conditions, and the second formulation position provides for release of at least about another about 10% to about 60% of the therapeutic within about 8 minutes after introduction of the formulation into physiological conditions.

In this embodiment, the polymer is patterned on the medical device, such that different positions on the device comprise different polymers with different release rates, different concentrations of the same polymer such that the different positions have different release rates, or combinations thereof. Thus, the "first formulation position" comprises one or multiple positions on the device that permit release at a faster rate than the release rate from the one or multiple positions that make up the "second formulation position". In a further embodiment, the array further comprises one or more positions comprising a third formulation position, wherein third formulation position provides for release of at least about another 10% to about 60% of the therapeutic within about 12 minutes after introduction of the formulation into physiological conditions. In one embodiment, each formulation position comprises the same polymer, wherein the concentration of the polymer in the first formulation position is less than the concentration of the polymer in the second formulation position, and wherein the concentration of the polymer in the second formulation position is less than the concentration of the polymer in the third formulation position when present, thus providing for the different release profiles. In one such embodiment, each formulation position comprises PEO, and the first formulation position comprises PEO at a concentration of between about 1 μg/mm$^2$ and 200 μg/mm$^2$; the second formulation position comprises PEO at a concentration of between about 10 μg/mm$^2$ and 300 μg/mm$^2$; and the third formulation position, when present, comprises PEO at a concentration of between about 25 μg/mm$^2$ and 500 μg/mm$^2$. In a further such embodiment, each formulation position comprises DS, and wherein the first formulation position comprises DS at a concentration of between about 1 μg/mm$^2$ and 200 μg/mm$^2$; the second formulation position comprises DS at a concentration of between about 10 μg/mm$^2$ and 300 μg/mm$^2$; and the third formulation position, when present, comprises DS at a concentration of between about 25 μg/mm$^2$ and 500 μg/mm$^2$.

In another embodiment, the first formulation position, the second formulation position, and the third formulation position when present do not all comprise the same polymer.

The arrays can be patterned on the medical device using any suitable procedure, including but not limited to masking techniques that are known to those of skill in the art (i.e.: a masked device is dipped into a formulation coating solution, or sprayed with a formulation coating solution).

In another aspect, the invention provides methods for using the medical devices of any aspect, embodiment, or combination of embodiments of the invention, wherein the medical device comprises a balloon, the method comprising inflating the balloon at a first location in a target blood vessel in a subject in need thereof for a first time period such that a first amount of the therapeutic is delivered to the first location in the target vessel;

deflating the balloon and moving the balloon catheter to a second location in the target blood vessel; and inflating the balloon at the second location for a second time period such that a second amount of the therapeutic is delivered to the second location in the target vessel.

The methods of this aspect of the invention provide multiple uses of the balloon, and thus much more efficient delivery of therapeutics, such as therapeutics to inhibit smooth muscle cell proliferation associate with angioplasty, to subjects with multiple diseased states in a target vessel, than is possible with current methods and devices. In one embodiment, the subject is suffering from one or more of coronary artery disease, peripheral vascular disease, carotid artery disease, or cerebral artery disease. Thus, the methods can be used to treat a patient suffering from one or more of coronary artery disease, peripheral vascular disease, carotid artery disease, or cerebral artery disease. In other embodiments, the balloon can be deflated and the balloon catheter moved to a third location in the target blood vessel, and the balloon can be inflated at the third location for a third period of time such that a third amount of the therapeutic is delivered to the second location of the target vessel. As will be understood by those of skill in the art, the process can be repeated further times as appropriate in light of the particular formation used. In a particular embodiment, the therapeutic comprises paclitaxel and/or paclitaxel albumin bound particles.

In another aspect, the invention provides methods of manufacturing a drug-coated medical device comprising:

(a) dipping a medical device into a solution comprising between about 10 weight percent and about 25 weight percent of a hydrophilic polymer and between about 0.6 weight percent and about 1.5 weight percent of a therapeutic to form a dipped medical device; and (b) drying the dipped medical device at about 50 degrees Celsius for between about 1 minute and about 96 hours to form the drug-coated medical device.

In various embodiments, the drying time in step (b) may be between about 1 hour and about 96 hours, about 1 hour and about 48 hours, about 1 hour to about 30 hours, about 1 hour to about 4 hours, about 4 hours and about 96 hours, about 4 hour and about 48 hours, about 4 hours to about 30 hours, about 4 hour, about 30 hours, about 48 hours, or about 96 hours. In one embodiment, the polymer comprises PEO and the drying time is between about 1 hour and about 4 hours. In another embodiment, the polymer comprises DS and the drying time is between about 1 minute and about 48 hours. In another embodiment, steps (a) and (b) are repeated a desired number of times to form a multi-layer drug-coated medical device, such as those disclosed herein. In a further embodiment, the medical device is a balloon portion of a balloon catheter, and wherein the balloon is inflated prior to step (a). In a still further embodiment, the balloon is inflated with a water/saline solution and wherein the water/saline solution is at a temperature of between about 37° C. to about 80° C.

In another aspect, the invention provides methods of manufacturing a drug-coated medical device comprising:

(a) placing a mask with a design on a surface of the medical device;

(b) applying a coating of a drug to the surface of the medical device to form a wet coated medical delivery device;

(c) drying the coated medical delivery device at about 50° C. for between about 1 minute and about 96 hours to form a dry coated medical device; and (d) removing the mask from the surface of the medical device thereby forming a drug-coated medical device.

In these different aspects, inflating the balloons with a water/saline solution warmer than 37° C. speeds up release kinetics. The water/saline solution may be prepared by a nurse at the desired temperature, may be drawn from a warm water bath, or an indeflator (inflation device; see below) could be operated (such as via battery) in such a way as to warm the water/saline solution before a physician inflates the angioplasty balloon. The indeflator may have a number of indicators on it that let the physician know when the treatment is done and he/she can move on to the next location (timer, color-indicator, thermocouple, etc.).

The spray-coating method of manufacturing a drug-delivery device comprise (a) placing the medical device between about 1 mm and about 100 mm away from a nozzle; and (b) using the nozzle to spraying the medical device with a coating comprising a polymer/therapeutic solution as discussed above to form the drug-coated medical device. The method may further comprise drying the drug-coated medical device in nitrogen for about 30 minutes and in air for about 15 minutes. Tables 1A and 1B show spray coating parameters for stent and balloon coating, respectively.

TABLE 1A

Spray coating parameters optimized for stent coating.

| Parameters | Values |
| --- | --- |
| Distance from nozzle tip to stent | 0.35 in |
| Ultrasonic power | 0.7 W |
| Syringe pump dispense rate | 0.02 mL/min |
| Focusing gas pressure | 0.5 psi |
| Drying gas pressure | 2 psi |
| Rotation rate | 70 rpm |
| Horizontal translation speed | 0.1 in/s (2.5 mm/s) |
| Number of loops | 120 loops |
| Drying time in nitrogen | 30 min |
| Drying time in air | 15 min |

TABLE 1B

Spray coating parameters range that is suitable for balloon coating.

| Parameters | Values |
| --- | --- |
| Distance from nozzle tip to balloon | 1-100 mm |
| Ultrasonic power | 0.1-10 W |
| Syringe pump dispense rate | 0.01-1 mL/min |
| Focusing gas pressure | 1-50 KPa |
| Drying gas pressure | Not required |
| Rotation rate | 10-1000 rpm |
| Horizontal translation speed | 0.1-500 mm/s |
| Number of loops | 10-1000 loops |
| Drying time in nitrogen | Not required |
| Drying time in air | Not required |

In various embodiments, the drying time in step (c) may be between about 1 hour and about 96 hours, about 1 hour and about 48 hours, about 1 hour to about 30 hours, about 1 hour to about 4 hours, about 4 hours and about 96 hours, about 4 hour and about 48 hours, about 4 hours to about 30 hours, about 4 hour, about 30 hours, about 48 hours, or about 96 hours. In one embodiment, the polymer comprises PEO and the drying time is between about 1 hour and about 4 hours. In another embodiment, the polymer comprises DS and the drying time is between about 1 minute and about 48 hours. In another embodiment, the coating of the drug is sprayed on the surface of the medical device to form the wet coated medical delivery device. In another embodiment, the medical device is dipped in the drug to form the wet coated medical delivery device. For example, a poly(ethylene oxide)/paclitaxel solution may be dried for about 1 hour after 4 different dippings. For dextran sulfate/paclitaxel solutions used to make polymer films, the drying time may depend on the type of solvent. When ethanol is used as the solvent, the drying time may be about 30 hours. When DMSO is used as the solvent, the drying time may be about 48 hours. For dextran sulfate coatings on balloons, the drying times are in minutes.

A mask may be used to create a pattern on a surface of the medical device. This method comprises: (a) placing a mask with a design on a surface of the medical device; (b) applying a coating of a drug to the surface of the medical device to form a wet coated medical delivery device; (c) drying the coated medical delivery device at about 50 degrees Celsius for between about 1 minute and about 96 hours to form a dry coated medical device; and (d) removing the mask from the surface of the medical device thereby forming a drug-coated medical device. The coating of the drug may be sprayed on the surface of the medical device to form the wet coated medical delivery device or the medical device may be dipped in the drug to form the wet coated medical delivery device.

In another aspect, the invention provides methods of manufacturing a drug-coated balloon portion of a balloon catheter comprising:

(a) inflating the balloon with a pressure of about 1-8 atm (or 6-8 atm);

(b) dipping the balloon in a coating solution comprising a biocompatible hydrophilic polymer and an therapeutic for about 1 second to about 4 hours (or between about 1 minute to about 4 hours, about 1 minute to about 2 hours, about 1 minute to about 1 hour, or about 1 minute) to form a wet coated balloon;

(c) drying the wet coated balloon in air at about 50° C. for about 10 minutes to about 4 hours to form a dry coated balloon;

(d) dipping the dry coated balloon in the coating solution of step (b) for about 1 second to about 1 hour to form a doubly wet coated balloon;

(e) drying the doubly wet coated balloon in air at about 50° C. for about 10 minutes to about 4 hours to for a doubly dry coated balloon; and (f) repeating steps (d) and (e) 1 more time to 20 more times to form the drug-coated balloon.

In another aspect, the invention provides methods of manufacturing a drug-coated balloon portion of a balloon catheter comprising:

(a) inflating the balloon with a pressure of about 1-8 atm (or 6-8 atm);

(b) dipping the balloon in a coating solution comprising a biocompatible hydrophilic polymer and an therapeutic for about 1 second to about 4 hours to form a first wet coated balloon;

(c) removing the wet coated balloon from the coating solution;

(d) dipping the wet coated balloon in a solvent selected from the group consisting of ethanol, dimethyl sulfoxide (DMSO), methanol, acetone, dimethyl formamide (DMF), acetonitrile, chloroform, methylene chloride, tetrahydrofuran, ethyl acetate, or a mixture thereof for about 1 second to about 4 hours (or between about 1 minute to about 4 hours, about 1 minute to about 2 hours, about 1 minute to about 1 hour, or about 1 minute);

(e) repeating step (d) 1-10 more times, wherein new solvent is used each time, in order to form a coated and dehydrated balloon;

(f) dipping the coated and dehydrated balloon in a solution of solvent and glycerol for about 1 second to about 4 hours (or between about 1 minute to about 4 hours, about 1 minute to about 2 hours, about 1 minute to about 1 hour, or about 1 minute);

(g) repeating step (f) with a solution of solvent and glycerol to form a second wet coated balloon; and (h) drying the second wet coated balloon for about 1 minute to 4 hours in order to for the drug-coated balloon.

In all aspect and embodiments of the methods for making devices of the invention, it will be understood by those of skill in the art that additional steps may be carried out to improve one or more properties of the resulting device for an intended use. For example, additional steps may be taken to further improve adherence of the formulations to the medical devices. Balloons (and other medical devices) are typically made up of hydrophobic materials. However, most balloons, for example, are coated (in whole or in part) with hydrophilic coating to reduce friction and to sustain lubricity for easy tracking into the blood vessel. The specific adhesive properties of the formulation may vary depending on the properties of the balloon (or other device) surface on which it is disposed. The balloon surface may be hydrophobic (without any hydrophilic coating) or hydrophilic (with a hydrophilic coating over the entire surface or any suitable portion thereof). In one embodiment, the device surface is hydrophobic (in whole or in part) and the methods further comprise coating the surface (in whole or in part) with an adhesion promoter prior to applying the formulation. In this embodiment, the adhesion promoter serves to improve (directly or indirectly) adhesion of the formulation to the device surface. Any suitable adhesion promoter can be used, including but not limited to poly(p-xylylene) polymers (such as PARYLENE®) used as moisture and dielectric barriers, organosilanes, and organotitanates. In another embodiment, the adhesion promoter comprises paclitaxel or particle-bound paclitaxel (without any polymer); paclitaxel is a hydrophobic compound but is highly adhesive to a number of different material surfaces, and thus may interact directly with the hydrophobic surface and the hydrophilic polymer in the formulation, thus promoting adhesion of the formulation to the surface. It will be understood by those of skill in the art that, in those embodiments in which paclitaxel is the therapeutic present in the formulation, it will help promote adherence of the formulation to the surface through paclitaxel-hydrophobic surface interactions.

In other embodiments, the device (such as a balloon) surface is hydrophilic (in whole or in part). In this embodiment, the adhesion promoter may comprise a hydrophilic polymer (without therapeutic); in various embodiments, the hydrophilic polymer may be PEO, DS, or any other suitable hydrophilic polymer. The polymer may further be cross-linked to provide more stability to the coating. In another embodiment, the biocompatible polymer in the formulation is negatively charged, and a positively charged polymer or material can be coated on the device/balloon surface. Then, the formulation can be applied to improve adhesion due to the electrostatic interactions between positively charged material and negatively charged polymer in the formulation. In this embodiment, the polymer adhesion promoter and the formulation can be deposited one over the other multiple times to build a multiple layer (i.e.: layer-by-layer approach, where the adhesion promoter can also act as an inert layer, as described herein). In another embodiment, albumin-bound paclitaxel may serve as the adhesion promoter; albumin-bound paclitaxel is a hydrophilic formulation, and can be applied this directly on the surface (hydrophobic or with a hydrophilic coating).

In another embodiment, the device (such as a balloon) surface can be treated with gas plasma (or other technique) to obtain a variety of surface functional groups (different types of surface chemistry), prior to application of the formulation. In this case, the formulation can be either physically deposited due to secondary bonding interactions with the modified surface, or covalently attached (primary bonding) to the functionalized device (such as a balloon) surface to improve adhesion.

In another embodiment, the device/balloon surface can be roughened or textured to increase the surface area. The formulation can then be applied on the roughened or texture surface to improve adhesion (i.e., increase surface area provides more sites for the attachment of formulation on the balloon surface).

In another embodiment, biodegradable metallic biomaterials including but not limited to magnesium, magnesium alloys, iron, iron alloys, or any other biodegradable metals can be coated on top of the formulation in whole or in part to provide enhanced stability to the formulation, and to make the formulation easier to handle. In a further embodiment, other metallic biomaterials including but not limited to titanium, stainless steel, and cobalt-chromium alloys can be coated on the top of the formulation in whole or in part to provide enhanced stability to the formulation, and to make the formulation easier to handle. These metallic biomaterials can be coated on the formulation in any suitable manner; in one embodiment, the coatings comprise different patterns (arrays) that not only to provide enhanced stability to the formulation and make the formulation easier to handle, but also may serve to further control and/or tailor the therapeutic release (as discussed for the formulation arrays above). Any suitable technique for depositing the metallic biomaterials can be used. In one embodiment sputter coating is used to deposit the metallic biomaterials to produce a very thin metallic biomaterial coating of nanometer thickness. As will be understood by those of skill in the art based on all of the teachings herein, these metallic biomaterial coatings may also serve as an inert layer (as defined herein) disposed atop the formulation.

FIG. 21 illustrates a device 100 used to inflate a drug delivery balloon, in accordance with another aspect of the invention. As shown in FIG. 21, the device 100 may include a housing 102 defining a chamber, the housing 102 having a distal end 104 and a proximal end 106. The device 100 may also include a plunger rod 108 positioned at the distal end 104 of the housing 102. The plunger rod 108 may be axially moveable within the chamber. In one example, the plunger rod 108 may include threads 110 interact with corresponding threads in the chamber. The housing 102 may be positioned within a cover 112, as shown in FIG. 21. In such an example, a distal end 113 of the cover 112 may include corresponding threads that interact with the threads 110 of the plunger rod 108. The device 100 may further include a tube 114 coupled to the proximal end 106 of the housing 102 and having a lumen configured for fluid communication with the housing 102. In such examples, a user may rotate the plunger rod 108 in a clockwise direction to move the plunger rod 108 towards the proximal end 106 of the housing 102. Such a movement may force a solution positioned within the housing 102 towards the proximal end 106 of the housing 102, and into the lumen of the tube 114. In yet another example, the proximal end of the plunger rod 108 may include a gasket to seal a solution positioned within the housing 102. In such an example, a user may simply move the plunger rod 108 towards the proximal end 106 of the housing 102 to force the solution positioned within the housing 102 into the lumen of the tube 114. Other examples are possible as well.

The device 100 may further include a pressure gauge 116 positioned between the housing 102 and the tube 114. The pressure gauge 116 may be used to determine a pressure of a solution within the lumen of the tube 114. Further, the device 100 may include a heating element 118 positioned adjacent to the housing 102. In one example, the heating element 118 comprises a resistance wire surrounding the housing 102. In such an example, the resistance wire comprises a material selected from the group consisting of nichrome, iron-chromium-aluminum alloys, copper alloys, or nickel-chrome alloys. Further, in such an example, the device 100 may further include a power source 120 coupled to the heating element 118. The power source 120 may be configured to provide a current to the resistance wire to thereby heat the solution positioned within the housing 102.

The device 100 may further include one or more indicators 122 coupled to the device 100. The one or more indicators 122 may be configured to provide a visual representation of one or more time periods. In one example, the one or more indicators 122 comprise a timer, as shown in FIG. 21. The timer may include a control 124 configured to start the timer. As such, a user may stop and start the timer for a given time period using the control 124. In another example, at least one of the one or more indicators 122 is configured to display one or more colors. For example, at least one indicator of the one or more indicators may be configured to display a first color (e.g., green) during a first portion of a given time period, and the at least one indicator may be configured to display a second color (e.g., red) during a second portion of the given time period. As such, the colored indicators may provide a user with an advance warning that a time period is coming to a close. In such an example, the one or more indicators 122 may include one or more light-emitting diodes (LEDs). In yet another embodiment, the one or more indicators 122 may provide one or more auditory indications of a completion of the one or more time periods.

The device 100 may further include a thermometer positioned within the chamber of the housing 102. The thermometer may be used to detect a temperature of a solution positioned within the housing 102. In such an example, the one or more indicators 122 may provide the one or more visual representations in response to a change in temperature detected by the thermometer. Further, the device 100 may include a temperature readout display 126 coupled to the housing 102 to provide a visual representation of a temperature detected by the thermometer.

The device 100 may further include a balloon inflation port coupled to and configured for in fluid communication with the tube 114, and a drug delivery balloon coupled to and configured for fluid communication with the tube 114. In such an example, the tube 114 may further include a connector 128 used to couple the tube 114 to the balloon inflation port. The connector 128 may be a luer-lock connector, a threaded connector, or some other type of connector. In such an example, an outer surface of the drug delivery balloon may include a drug formulation. The drug formulation may comprise any of the formulations described above. Such a drug delivery balloon may have an inflated diameter in the range from about 1 mm to about 40 mm. In one example, the drug delivery balloon may have a constant diameter, while in another example, the drug delivery balloon may have a variable diameter or a tapered diameter. Further, such a drug delivery balloon may have a length from about 20 mm to about 300 mm. In such an example, the one or more time periods may comprise one or more inflation periods for the drug delivery balloon. As such, the one or more indicators 122 provide a visual representation of one or more inflation periods for the drug delivery balloon. In one example, the one or more indicators 122 comprise a first indicator configured to provide a visual representation of a first inflation period for the drug delivery balloon, and a second indicator configured to provide a visual representation of a second inflation period for the drug delivery balloon. In another example, the one or more indicators 122 further comprise a third indicator configured to provide a visual representation of a third inflation period for the drug delivery balloon.

FIG. 22 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 202, the method involves heating a solution in the chamber of the device to a desired temperature via the heating element. The solution in the chamber of the device may be a saline contrast mixture, for example. In one example, the desired temperature is in the range from about 37° C. to about 45° C. At block 204, the method involves delivering the drug delivery balloon apparatus to a first location in a desired treatment vessel. The drug delivery balloon apparatus may be introduced and delivered in a standard coaxial manner, via over-the-wire or rapid exchange techniques, as examples. At block 206, the method involves inflating the drug delivery balloon at the first location via a balloon inflation port. In one embodiment, the drug delivery balloon may be inflated by injecting a saline contrast mixture, for example. The saline contrast mixture may be advanced from the chamber of the housing, through the lumen, into the balloon inflation port from the lumen, into the drug delivery balloon until the drug delivery balloon is inflated. The pressure gauge may be used to detect a pressure of the drug delivery balloon. The pressure exerted on the target vessel wall may range between about 0 ATM to about 12 ATM. In a specific embodiment, the pressure exerted on the target vessel wall may range between about 0.25 ATM and about 3.0 ATM. At block 208, the method involves receiving a visual representation of a completion of a first inflation period from the one or more indicators coupled to the device. The ability to control the inflation temperature of the inflation solution may be advantageous to adjust a rate at which a drug solution on the drug delivery balloon degrades.

The method may further include delivering the drug delivery balloon apparatus to a second location in the desired treatment vessel, inflating the drug delivery balloon at the second location via the balloon inflation port, and receiving a visual representation of a completion of a second inflation period from the one or more indicators coupled to the device. In yet another example, the method may further include delivering the drug delivery balloon apparatus to a third location in the desired treatment vessel, inflating the drug delivery balloon at the third location via the balloon inflation port, and receiving a visual representation of a completion of a third inflation period from the one or more indicators coupled to the device.

FIG. 23 illustrates a drug delivery balloon apparatus 300, in accordance with another aspect of the invention. As shown in FIG. 23, the drug delivery balloon apparatus 300 may include a housing 302 having a first lumen and a second lumen. The drug delivery balloon apparatus 300 may further include a catheter 304 having a first end 306 coupled to the housing 302. The drug delivery balloon apparatus 300 may further include a balloon inflation port 308 coupled to one or more of the housing 302 and the first lumen. The balloon inflation port 308 may further include a connector used to couple the balloon inflation port 308 to another device or lumen. Such a connector may be a luer-lock connector, a threaded connector, or some other type of connector. The drug delivery balloon apparatus 300 may further include a guidewire port 310 coupled to one or more of the housing 302 and the second lumen. The guidewire port 310 may be configured to receive guidewire 312 to advance the drug delivery balloon apparatus 300 to a desired treatment vessel. The second lumen may be sized to receive a guidewire having a diameter in the range of about 0.008 inches to about 0.05 inches. As with the balloon inflation port 308, the guidewire port 310 may further include a connector used to couple the guidewire port 310 to another device or lumen. Such a connector may be a luer-lock connector, a threaded connector, or some other type of connector.

The drug delivery balloon apparatus 300 may further include a drug delivery balloon 314 coupled to a second end 316 of the catheter 304 and configured for fluid communication with the first lumen of the housing 302. In such an example, an outer surface of the drug delivery balloon 308 may include a drug formulation. The drug formulation may comprise any of the formulations described above. The drug delivery balloon 314 may have an inflated diameter in the range from about 1 mm to about 40 mm. In one example, the drug delivery balloon may have a constant diameter, while in another example, the drug delivery balloon may have a variable diameter or a tapered diameter. Further, such a drug delivery balloon may have a length from about 20 mm to about 300 mm. The drug delivery balloon apparatus 300 may further include one or more indicators 318 coupled to the housing 302 of the drug delivery balloon apparatus 300. The one or more indicators 318 may be configured to provide a visual representation of one or more inflation periods for the drug delivery balloon 314. In one example, the one or more inflation periods for the drug delivery balloon 314 comprise at least two inflation periods.

In one example, the one or more indicators 318 comprise a timer. Such a timer may be manually operable by a user via a control configured to start the timer, for example. The user may start the timer when an inflation period begins, and subsequently check the timer until the desired end of the inflation period. In another example, at least one of the one or more indicators 318 is configured to display one or more colors. For example, at least one indicator of the one or more indicators may be configured to display a first color (e.g., green) during a first portion of a given inflation period, and the at least one indicator may be configured to display a second color (e.g., red) during a second portion of the given inflation period. As such, the colored indicators may provide a user with an advance warning that the inflation period is coming to a close. In such an example, the one or more indicators 122 may include one or more light-emitting diodes (LEDs). In yet another embodiment, the one or more indicators 318 may provide one or more auditory indications of a completion of the one or more inflation periods for the drug delivery balloon 314.

In another example, the drug delivery balloon apparatus 300 may further include a pressure sensor coupled to the catheter 304. In such an example, drug delivery balloon apparatus 300 may include a pressure transducer line to electrically connect the pressure sensor to a power source and/or a computing device configured to display data from the pressure sensor. In one example, such a computer device may be integrated within the housing 302 of the drug delivery balloon apparatus 300. In another example, the pressure sensor may be configured to wirelessly communication with the computing device configured to display data from the pressure sensor. In such an example, the one or more indicators 318 may be configured to provide the one or more visual representations in response to a change in pressure detected by the pressure sensor.

For example, the pressure sensor may detect a pressure of a desired treatment vessel, and if the pressure in the desired treatment vessel drops below a threshold level, the one or more indicators 318 maybe configured to provide the visual representations. In another example, the drug delivery balloon apparatus 300 may further include a thermometer coupled to the catheter. In such an example, the one or more indicators 318 may be configured to provide the one or more visual representations in response to a change in temperature detected by the thermometer.

In yet another example, the one or more indicators 318 comprise a first indicator configured to provide a visual representation of a first inflation period for the drug delivery balloon 300, and a second indicator configured to provide a visual representation of a second inflation period for the drug delivery balloon 300. In another example, the one or more indicators 318 further comprise a third indicator configured to provide a visual representation of a third inflation period for the drug delivery balloon 300.

FIG. 24 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 402, the method involves advancing the drug delivery balloon apparatus described above to a first location in a desired treatment vessel via the catheter. The drug delivery balloon apparatus may be introduced and delivered to the first location in a standard coaxial manner, via over-the-wire or rapid exchange techniques, as examples.

At block 404, the method involves inflating the drug delivery balloon at the first location via the balloon inflation port. In one embodiment, the drug delivery balloon may be inflated by injecting a saline contrast mixture, for example, into the balloon inflation port. The saline contrast mixture may then be advanced through the first lumen to the drug delivery balloon until the drug delivery balloon is inflated. In another embodiment, the drug delivery balloon may be inflated using any other suitable fluid medium.

At block 406, the method involves receiving a visual representation of a completion of a first inflation period from a first indicator. The first inflation period may range from about 1 minute to about 4 minutes. At block 408, the method involves advancing the drug delivery balloon to a second location in the desired treatment vessel. As discussed above, the drug delivery balloon may be advanced to the second location in a standard coaxial manner, via over-the-wire or rapid exchange techniques, as examples. At block 410, the method involves inflating the drug delivery balloon at the second location via the balloon inflation port. As discussed above, the drug delivery balloon may be inflated using a saline contrast mixture, or any other suitable fluid medium. At block 412, the method involves receiving a visual representation of a completion of a second inflation period from a second indicator. The second inflation period may range from about 1 minute to about 4 minutes.

The method may further include advancing the drug delivery balloon to a third location in the desired treatment vessel, inflating the drug delivery balloon at the third location via the balloon inflation port, and receiving a visual representation of a completion of a third inflation period from a third indicator.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

EXAMPLES

Example 1

In this example, the use of dextran sulfate (DS) polymer was investigated as a platform to control the drug release from balloons. More specifically, dextran sulfate coatings were developed as a drug delivery platform for balloons to avoid significant drug loss during the typical time period of balloon tracking (1 min), and then to immediately deliver a clinically relevant dose of drug during the typical time period of balloon inflation and treatment (from 1 min to 4 min). The characterizations using SEM, FTIR, and DSC showed that the films prepared were smooth and homogenous with PAT molecularly dispersed in the bulk of DS matrix in amorphous form. An investigation on the interaction of smooth muscle cells (SMCs) with control-DS and PAT-DS films showed that both films inhibited SMC growth, with a superior inhibitory effect observed for PAT-DS films. PAT-DS coatings were then produced on balloon catheters. The integrity of coatings was well-maintained when the balloons were either deflated or inflated. In this study, up to 2.2 µg/mm$^2$ of PAT was loaded on the balloons using the DS platform. Drug elution studies showed that only 10-20% of the total PAT loaded was released from the PAT-DS coated balloons during the typical time period of balloon tracking (1 min) and then ~80% of the total PAT loaded was released during the typical time period of balloon inflation and treatment (from 1 min to 4 min). Thus, this study demonstrated the use of DS as a platform to control drug delivery from balloons.

Materials

Dextran sulfate sodium salt, MW ca>500,000 Da was purchased from Alfa Aesar (USA). Absolute ethanol (200 proof), dimethyl sulfoxide (DMSO), glycerol (≥99.5%), HPLC-grade water and acetonitrile, phosphate buffered saline with 0.05% Tween-20 (PBS/T-20), and fluorescein diacetate (FDA) were all purchased from Sigma-Aldrich (USA). Paclitaxel was purchased from Chemietek (Indianapolis, Ind.). All the chemicals were used as received.

Preparation of Paclitaxel Loaded Dextran Sulfate Films

Paclitaxel (PAT) loaded dextran sulfate (DS) films (PAT-DS) were prepared by a solvent-casting method. A polymer-drug solution was prepared with 25 w/v % of DS, 0.27 w/w % of paclitaxel (PAT), and 10 w/w % of glycerol (plasticizer) in a solvent mixture of deionized water (di-H$_2$O) and ethanol or DMSO. For example, to prepare a typical PAT-DS film, 7.5 g of DS and 750 µs of glycerol were initially dissolved in 27 mL of di-H$_2$O and stirred at 400 rpm for 3 h. In parallel, a solution of PAT was prepared by sonicating 20 mg of PAT in 3 mL of ethanol or DMSO for 15 min. Thus prepared PAT solution was added to the DS solution and the polymer-drug mixture was stirred at 400 rpm for 18 h. After that, the solution was heated at 50° C. for 1 h with continuous stirring. The solution was then poured into a glass petri-dish (9 cm in diameter) and immediately transferred to a vacuum oven, which was preheated at 50° C., and maintained under vacuum at a pressure of −20 inHg. The films prepared using ethanol as a solvent was taken out after 30 h while the films prepared using DMSO was taken out after 48 h. The PAT-DS films were peeled off from the petri-dish and cut into specimens of appropriate sizes for different characterizations. The PAT-DS films prepared using the solvents ethanol and DMSO are denoted in this study as PAT-DS-1 and PAT-DS-2, respectively. Control DS films (Ctrl-DS) were also prepared using the same method without incorporating PAT. The Ctrl-DS films prepared using the solvents ethanol and DMSO are denoted in this study as Ctrl-DS-1 and Ctrl-DS-2, respectively.

Characterizations

Both the Ctrl-DS and PAT-DS films prepared in this study were characterized using scanning electron microscopy (SEM), Fourier transform infrared (FTIR) spectroscopy, and differential scanning calorimetry (DSC).

A Quanta 450 SEM (FEI, USA) was used to observe the surface morphology as well as the cross-sectional morphology of the films at an accelerating electron voltage of 30 KV. Prior to SEM imaging, all the samples were sputter-coated with a 15 nm thick layer of gold-palladium. A Nicolet 6700 FTIR spectroscopy (Thermo Scientific, USA) equipped with an attenuated total reflection (ATR) accessory was used to characterize the film surfaces. All the IR spectra presented here were collected at 512 scans with a spectral resolution of 4 cm$^{-1}$. A DSC Q200 (TA Instruments, USA) was used to characterize the thermal properties of all the films prepared in this study. For this characterization, the film samples weighing 8-10 mg were sealed in an aluminum pan and heated from 0 to 350° C. at a scanning rate of 10° C./min. All the measurements were carried out in a chamber purged with nitrogen gas at a flow rate of 40 mL/min.

Mechanical Properties

A MTS insight electromechanical apparatus (MTS Systems Corp., Eden Prairie, Minn.) equipped with a 100 N load cell was used to carry out the tensile test for Ctrl-DS and PAT-DS films (n=3 each) prepared in this study. For this characterization, the films were cut into rectangular specimens of 5 cm×1 cm. A length of 1 cm from each end of the specimen was gripped to obtain a stressed region of 3 cm×1 cm. The specimens were then pulled at a rate of 50 mm/min until they break. A plot of tensile stress (MPa) vs. strain (%) was obtained for each specimen using TESTWORKS® 4 software.

High Performance Liquid Chromatography (HPLC) A Waters HPLC system equipped with a Waters 2489 UV/Vis detector was used in this study. A Nova-Pak C18 column of 4 µm particle size was used and a 10 µL volume of the sample was injected for the analysis. The HPLC protocol was followed as reported previously.[3] Briefly, a mobile phase of water/acetonitrile (45:55, v/v) at a flow rate of 1 mL/min was used. The UV detector was set at the wavelength of 227 nm, and the column temperature was maintained at 35° C. A linear plot with the correlation coefficient (R$^2$) of 0.9997 was used for the calibration range of 0.003-20 µg/mL.

Drug Release Studies of PAT-DS Films

For the drug release studies, the PAT-DS films (1 cm×1 cm, n=6) were immersed in 40 mL of PBS/T-20 solution in a circulating water bath at 37° C. by holding the specimen carefully using a tweezer. As a standard procedure, tween-20 was added to PBS to maintain sink conditions by increasing the solubility of PAT in PBS. The specimens were taken out of the solution at several pre-determined time points (15 s, 30 s, 1 min, 2 min, and 5 min) and transferred to a fresh PBS/T-20 solution until the next time point. After 5 min, the tweezer used for holding the specimens was immersed in the solution for two more minutes (5 to 7 min), and manually shaken well to transfer any of the undissolved films attached to the tweezer into the solution. Prior to HPLC analysis, as a standard procedure, 2 mL of ethanol (EtOH) was added to the PBS/T-20 solutions collected in the polypropylene tubes to remove any PAT adsorbed on the surfaces of tubes during drug-elution studies. The high performance liquid chromatography (HPLC) protocol for determining PAT was followed.

Smooth Muscle Cell (SMC) Culture

Human aortic smooth muscle cells (HASMCs, catalog no. 354-05a) and SMC growth medium (catalog no. 311-500) were purchased from Cell Applications (San Diego, Calif.). The SMCs in passage 4-6 were cultured in the growth medium in a humidified incubator supplied with 5% $CO_2$ and maintained at 37° C. The following experiment was carried out to study the interaction of SMCs with the Ctrl-DS and PAT-DS films prepared in this study. A density of $15 \times 10^3$ cells (in 1 mL of growth medium) was allowed to grow in the wells of a 24-well tissue culture plate. After 24 h, the used medium was removed from each well and 1 mL of fresh medium was added. Then, the Ctrl-DS and PAT-DS films were added individually to the cells grown in the wells. On day-1 (after 24 hours of adding films to the cells), the used media were removed and 1 mL of fresh growth media was added to the wells. After that, the media were changed on days-3 and 5. For the control experiment, the cells were allowed to grow in the wells without adding any films. Also, to evaluate the dose responses of Ctrl-DS and PAT-DS films on the growth of SMCs, two different sizes (0.5 cm×0.5 cm and 1 cm×1 cm) of films were used in this experiment.

SMC Viability, Proliferation, Morphology, and Phenotype Studies

The viability and proliferation of SMCs were measured using resazurin fluorometric assay. For observing cell morphology, the SMCs were stained with fluorescein diacetate and imaged using fluorescence microscopy. The phenotype of SMCs was studied by immunofluorescence using smooth muscle α-actin primary antibody, goat anti-mouse IgG-FITC secondary antibody, and propidium iodide for staining the nucleus. The immunofluorescence protocol was carried out.

SMC Morphology Study

A 1 mg/mL concentration of FDA in acetone was prepared as a stock solution. The stock solution was stored at 4° C. prior to use. To obtain the working solution, 200 µL of the stock solution was added to 1800 µL of DPBS. On day-1, 3, and 5, the used media were removed and the cells were washed twice with 1 mL of cold DPBS (stored at 4° C.). Then a mixture of 1000 µL of DBPS and 60 µL of FDA working solution was added to each well. The cells were then incubated in dark at 4° C. for 15 min. The fluorescent labelled cells were then imaged using an Axiovert 200 M fluorescence microscope (Carl Zeiss, Thornwood, N.Y.).

Preparation of PAT-DS Coatings on Balloons

Three different PAT-DS coating solutions were prepared with low, medium, and high doses of PAT. Each of these solutions was prepared with 75 w/v % of DS and 10 w/w % of glycerol (plasticizer) in a solvent mixture of di-$H_2O$ and ethanol. The w/w % of PAT was 0.27, 0.54, and 0.81 for low, medium, and high doses. To prepare each of the coating solution, DS was initially dissolved in 9 mL of di-$H_2O$ and stirred at 100 rpm for 3 h. After that, the solution of PAT in 1 mL of ethanol was added to the DS solution, and the drug-polymer mixture was allowed to stir at 100 rpm for 18 h.

Angioplasty balloon catheters (ev3 Inc., USA) of 4 mm in diameter × 20 mm in length were used in these experiments. Initially, the balloons were inflated with a pressure of 6-8 psi. Then, the inflated balloons were dipped in the coating solutions for 30 sec. After that, the coated balloon was slowly taken out of the solution and immediately dipped into 100% ethanol for 1 min for dehydration. This procedure of dipping in ethanol for 1 min was repeated thrice more with fresh ethanol used each time. Then, the coated and dehydrated balloon was dipped in a solution mixture of ethanol and glycerol (9:1, v/v) for 1 min twice with fresh solution mixture used each time. After that, the balloons were dried in a laminar airflow hood for 30 min.

SEM Imaging of PAT-DS Coated Balloons

The SEM images of PAT-DS coated balloons were taken at three different stages: as-coated, deflated, and inflated positions. An accelerated electron voltage of 1 KV was used to obtain SEM images at several different areas of the balloons. For determining the thickness of PAT-DS coating on balloons, the coated balloons were carefully cut for cross-section, and sputter-coated with a 15 nm thick gold palladium coating. The cross-sectional images were obtained using an accelerated electron voltage of 15 KV.

Drug Elution Studies of PAT-DS Coated Balloons

The coated balloons were deflated prior to drug elution studies. Then, the balloons were immersed in 40 mL of PBS/T-20 solution in a circulating water bath at 37° C. The balloons were taken out of the solution at time points 30 sec and 1 min, and transferred to a fresh PBS/T-20 solution until the next time point. After 1 min time point, when the balloon was transferred to the fresh PBS/T-20 solution, it was inflated with a pressure of 6-8 psi in PBS/T-20 solution. Then, the balloons were taken out of the solution at other time points 2 min, 3 min, 4 min, 5 min, and 7 min, and transferred to fresh PBS/T-20 solution for every time point used in this study. After 5 min time point and until 7 min, the balloon was manually shaken well to completely retrieve the residual PAT-DS present on the balloon.

Statistical Analysis

The experimental data collected are reported as mean±standard deviation. A one-way analysis of variance (ANOVA) was used to determine the statistical significance at $p < 0.05$. Unless otherwise mentioned, three samples were used for each sample group at each time point in every cell-based experiment used in this study.

Results

Characterization of Ctrl-DS and PAT-DS films

FIG. 3 shows the SEM images of surfaces and cross-sections of Ctrl-DS and PAT-DS films. Both the surfaces and the cross-sections of the films were carefully examined for their smoothness, homogeneity, and presence of any defects. The Ctrl-DS films were transparent in appearance. The surfaces of Ctrl-DS-1 (FIG. 3A) and Ctrl-DS-2 (FIG. 3B) were smooth and homogeneous with no surface defects observed. The cross-section of Ctrl-DS-1 (FIG. 3E) predominantly showed a fibrous-like morphology while the cross section of Ctrl-DS-2 (FIG. 3F) showed a relatively flat morphology with few fibrous-like protrusions. The PAT-DS films were whitish in appearance due to the incorporation of PAT. The surfaces of PAT-DS-1 (FIG. 3C) and PAT-DS-2 (FIG. 3D) were also smooth, homogeneous, and defect-free. The cross-sections of both PAT-DS-1 (FIG. 3G) and PAT-DS-2 (FIG. 3H) films appeared much smoother when compared to that of their respective control DS films. Unlike Ctrl-DS films, no fibrous-like morphology was observed in the cross-sections of PAT loaded DS films (FIG. 3 G,H). This could suggest that the PAT loaded act as a filler between DS polymer molecules to provide a smoother morphology. Also, no PAT crystals (typically exists in needle or plate-like morphologies) were observed in the cross-sections of PAT-DS films (FIG. 3 G,H). This suggested that the PAT was molecularly dispersed in the DS matrix.

All the FTIR spectra obtained in this study were interpreted using several references from the literature, and chemical structures of DS and PAT were determined (data not shown). The FTIR spectrum of dextran sulfate powder contained the following characteristic bands (cm$^{-1}$): 3479 v(O—H), 2949 v(C—H), 1634 δ(HOH), 1457 and 1386 δ(C—H), 1220 $v_s$(S=O), 1200-1000 complex band v(C—O) and v(C—C), 981 $v_{as}$(S=O), 932 γ(C—H), 800 v(O—S—O), 800-600 complex band γ(C—H). The FTIR spectrum of PAT powder contained the following characteristic bands (cm$^{-1}$): 3440 v(O—H), 2944 v(C—H), 1732 and 1704 v(C=O) of ester group, 1649 v(C=O) of amide group, 1369 δ(C—H), 1200-1000 complex band v(C—O) and v(C—C), 1000-600 complex band γ(C—H).

The FTIR spectra of Ctrl-DS and PAT-DS films were determined (data not shown). In these spectra, the characteristic peaks of DS were observed around the same positions as that of DS powder. This suggested that the chemical structure of DS was not altered either when the polymer was made into a film or after the PAT was incorporated into the DS. The sulfate groups (SO$_3$) in DS is primarily responsible for the anticoagulant activity of the polymer. The presence of peaks for the S=O group at 1221 and 981 cm$^{-1}$, and the peak for O—S—O group at 800 cm$^{-1}$ in both Ctrl-DS and PAT-DS showed that the functional groups providing the anticoagulant properties are not affected in the films prepared. A new peak was observed at 952 cm$^{-1}$ in the films prepared using DMSO as a solvent. This peak was assigned to the rocking vibration of —CH$_3$ groups of DMSO. This suggested that a trace amount of DMSO was present in Ctrl-DS-2 and PAT-DS-2 films. Also, no peaks for PAT were observed for the PAT-DS films. This suggested that the PAT was not present on the surface of PAT-DS, and was successfully incorporated into bulk of the DS matrix.

The DSC thermograms of DS powder, PAT powder, Ctrl-DS films, and PAT-DS films were determined (data not shown). For the DS powder, three peaks were observed: (a) an endothermic peak for the glass transition temperature ($T_g$) at 133° C.; (b) an exothermic peak for the crystallization temperature ($T_c$) at 210° C.; and (c) a small endothermic peak for the melting temperature ($T_m$) at 272° C. This suggested that the DS powder used in this study was semicrystalline. For the PAT powder, an endothermic melting peak was observed at 225° C., which was immediately followed by an exothermic decomposition peak at 237° C. For the Ctrl-DS-1 film, the peak for $T_g$ slightly reduced to 124° C. whereas the peak for $T_c$ increased to 226° C. when compared to those of DS powder. Also, the peak for $T_m$ slightly increased to 279° C. An endothermic peak for the evaporation of glycerol was observed at 290° C. The area under the peaks for both $T_g$ and $T_m$ were much larger for Ctrl-DS-1 when compared to those of DS powder. This suggested that the degree of amorphous and crystalline regions in the film was significantly increased when compared to that of powder. After the incorporation of PAT, a doublet peak with a very small shoulder peak at 127° C. and a broad diffuse peak at 148° C. were observed for the $T_g$ of DS and the $T_m$ of amorphous form of PAT, respectively. In the literature, when the peak for $T_g$ of a polymer disappears or becomes very small after the incorporation of drug, it is attributed to the immobility of polymer chains due to the formation of intermolecular bonding interactions between the polymer and the drug.[15] This suggested that, in this study, the PAT formed intermolecular hydrogen bonding interactions with DS and prevented polymer chain mobility. It has been previously shown in the literature that the melting point of amorphous form of PAT (~150° C.) is significantly lesser than that of its crystalline form (~225° C.). This suggested that the PAT was present in amorphous form inside the DS matrix. Also, a peak for the evaporation of glycerol was observed in these films at 293° C. For the Ctrl-DS-2 film, the $T_g$ was slightly increased to 138° C. when compared to that of the powder. The $T_c$ was significantly reduced for these films with dual exothermic peaks observed at 168° C. and 176° C., and the $T_m$ was observed at 270° C. For the PAT-DS-2, the endothermic peak at 135° C. was broadened with tailing. This could be due to the overlap of peaks for $T_g$ of DS and $T_m$ of amorphous form of PAT, as observed in PAT-DS-1. The other peaks for $T_c$ and $T_m$ for PAT-DS-2 were observed at the positions similar to those of Ctrl-DS-2.

Mechanical Properties of Ctrl-DS and PAT-DS Films

FIG. 4 shows the stress-strain curves of Ctrl-DS and PAT-DS films prepared in this study. In the literature, based on the shape of stress-strain curves, polymers are generally classified under five categories: (a) hard-tough; (b) soft-tough; (c) hard-brittle; (d) soft-weak; (e) soft-tough.[17] "Hard" refers to high tensile strength and modulus while the "soft" refers to low tensile strength and modulus. The polymers that show high elongation are classified as "tough" whereas the polymers that show low elongation are classified as "brittle". If the polymer has moderate elongation, then it is classified as "strong" or "weak" depending on its tensile strength. Based on this standard classification, the films prepared in this study are categorized. All the Ctrl-DS and PAT-DS films prepared in this study showed a low modulus (<10 MPa), indicating that the material is soft, and a high elongation before fracture (>380%), indicating that the material is tough. Thus, all the films prepared in this study can be categorized under "soft-tough" category. FIG. 4b shows the tensile strength (MPa), strain at break (%), and modulus (MPa) for all the Ctrl-DS and PAT-DS films. The values obtained for PAT-DS-1 and PAT-DS-2 films were similar to their respective Ctrl-DS films. This showed that the incorporation of PAT did not affect the mechanical properties of DS films. However, the films prepared using different solvents showed significant difference in the values. The films prepared using ethanol showed much higher tensile strength and modulus than that of the films prepared using DMSO. On the other hand, the films prepared using DMSO showed better elongation (higher strain at break %). Nevertheless, it is important to note that all the Ctrl-DS and PAT-DS films prepared in this study exhibited excellent elongation (>380%) irrespective of type of solvents used to prepare them. These results showed that the films developed are promising as a coating for drug-coated balloons since the coating needs to be expanded when the balloon is inflated at the treatment site.

Drug Release from PAT-DS Films

The total amount of PAT loaded in PAT-DS-1 and PAT-DS-2 films (1 cm×1 cm) were determined as 1.4±0.3 µg/mm$^2$, and 1.6±0.3 µg/mm$^2$, respectively. The cumulative release of PAT is provided in FIG. 5A. Only a trace amount (0.2 µg/mm$^2$) of PAT was released until 1 min. After that, most of the drug loaded (1.2 µg/mm$^2$) was released by 5 min. This suggested that the PAT-DS films completely dissolved by 5 mins. After 5 min, only a trace amount (0.1 µg/mm$^2$) of PAT was retained. Several clinical studies in the literature have shown that a dose of 1 µg/mm$^2$ was effective in inhibiting neointimal hyperplasia.

SMC Viability and Proliferation

FIG. 6A shows the viability of SMCs treated with Ctrl-DS and PAT-DS films (specimen size: 0.5 cm×0.5 cm). The dose of DS in Ctrl-DS films of 0.5 cm×0.5 cm was determined as 30 mg. The doses of DS and PAT in PAT-DS films of 0.5 cm×0.5 cm were determined as 30 mg and 37 µg, respectively. For the control experiment, the cells were allowed to grow in the wells without any films (Ctrl-well). At all the time points (day—1, 3, and 5), the number of viable cells for Ctrl-DS-1, Ctrl-DS-2, PAT-DS-1, and PAT-DS-2 were significantly lesser than that of the Ctrl-well. This suggested that all the films prepared in this study effectively inhibited the growth of SMCs. Also, the number of cells for PAT-DS films was significantly lesser than that of the Ctrl-DS films. This showed that the PAT released from DS films successfully inhibited the growth of SMCs. The percentage of increase or decrease in the proliferation of SMCs from day-1 to day-5 was determined and is provided in FIG. 6B. Both the Ctrl-DS and PAT-DS films significantly inhibited the proliferation of SMCs. Also, the inhibitory rate was significantly greater for PAT-DS films when compared to Ctrl-DS films. This shows that the PAT incorporated DS films provide greater inhibitory effect on cell growth than Ctrl-DS films.

The viability of SMCs treated with Ctrl-DS and PAT-DS films (specimen size: 1 cm×1 cm) is shown in FIG. 7A. The dose of DS in Ctrl-DS films of 1 cm×1 cm was determined as 118 mg. The doses of DS and PAT in PAT-DS films of 1 cm×1 cm were determined as 118 mg and 147 µg, respectively. Similar to the results obtained for the specimen size of 0.5 cm×0.5 cm, the number of viable cells for all the Ctrl-DS and PAT-DS films were significantly lesser than that of Ctrl-well. However, unlike 0.5 cm×0.5 cm specimens, no significant difference in the number of viable cells was observed between Ctrl-DS and PAT-DS films of 1 cm×1 cm specimen size. The proliferation of SMCs was also significantly inhibited for all the Ctrl-DS and PAT-DS films (FIG. 7B). Also, unlike 0.5 cm×0.5 cm specimens, no significant difference in the proliferation was observed between most of the Ctrl-DS films and PAT-DS films of 1 cm×1 cm. These results suggested that the doses of DS and PAT used in the films play a vital role in determining the degree of inhibition of SMC growth.

SMC Morphology

Fluorescence microscopy images of FDA-stained SMCs in Ctrl-well as well as the cells treated with Ctrl-DS and PAT-DS films (0.5 cm×0.5 cm) were obtained (data not shown). The cells in the Ctrl-well were elongated and showed its characteristic spindle-shape with a typical hill-and-valley morphology. The cells treated with Ctrl-DS films also showed the characteristic spindle shape to a larger extent. However, some cells were discoid (flat circular) in shape. The cells treated with PAT-DS films showed greater reduction in its number and confluence. Also, the cells were discoid in shape. On day 5, the confluence of SMCs in Ctrl-well, Ctrl-DS-1, Ctrl-DS-2, PAT-DS-1, and PAT-DS-2 was estimated to be 80-85%, 35-40%, 40-45%, <5%, and 5-10%, respectively. These results are in excellent agreement with the quantitative data to show that both Ctrl-DS and PAT-DS films inhibited the growth of SMCs with superior inhibitory effect observed for PAT-DS films.

There were only very few cells present for any of the Ctrl-DS or PAT-DS films. Also, the cells predominantly showed the uncharacteristic discoid shape for all the films. The confluence of SMCs in Ctrl-well, Ctrl-DS-1, Ctrl-DS-2, PAT-DS-1, and PAT-DS-2 on day 5 was estimated to be 80-85%, <5%, 5-10%, <1%, and <1%, respectively. These results are also in excellent agreement with the quantitative data to show that both Ctrl-DS and PAT-DS films exhibit dose-dependent inhibitory effect.

SMC Phenotype Study

Smooth muscle (SM) α-actin is a protein present in the cytoplasm of SMCs and plays a vital role in regulating cell shape and movement. The expression of SM α-actin is strong for the well growing SMCs whereas the expression is weak for the damaged cells.[7] Also, the α-actin filaments are oriented along the cell axis in well growing SMCs whereas the filaments are disarranged in damaged SMCs.[7] The immunofluorescence microscopy images of SMCs in the Ctrl-well showed strong SM α-actin expression (data not shown). Also, the filaments were oriented along the cell axis. The cells showed similar strong expression of SMC α-actin for the Ctrl-DS films of 0.5 cm×0.5 cm. However, the expression was poor for the Ctrl-DS films of 1 cm×1 cm. The cells treated with PAT-DS films, irrespective of the specimen size, showed weaker SM α-actin expression with the filaments disarranged in circumferential orientation. Also, some of the cells treated with PAT-DS films (1 cm×1 cm) even showed the complete absence of SM α-actin with only the nucleus present. These results further confirmed that the Ctrl-DS films, especially at higher doses, can show strong inhibitory effect. The PAT-DS films, irrespective of the doses, were effective in greatly inhibiting SMC growth.

PAT-DS Coatings on Balloons

FIGS. 8 A-C and 8D-F shows the SEM images of bare balloons (without PAT-DS coating) in inflated and deflated positions, respectively. The images of inflated position show that the balloons are fully expanded whereas the images of deflated position show the flaps of balloon due to deflation. FIGS. 8G-I, 8J-L, and 8M-O shows the SEM images of as-coated, deflated, and inflated positions of PAT-DS coated balloons with low dose of PAT incorporated, respectively. These images showed that the PAT-DS coating was uniform, smooth, and homogeneous on the balloons. The integrity of PAT-DS coating on the balloons was well-maintained without delamination, crack formation, or any mechanical defects when the balloons were either deflated or inflated. Similar results were also observed for PAT-DS coatings on the balloons with medium and high doses of PAT incorporated (FIG. 9). FIG. 10 A-C shows the cross-sectional SEM images of PAT-DS coated balloons. The thickness of PAT-DS coatings were determined as 122±6 µm, 144±10 µm, and 148±22 µm for low, medium, and high doses of PAT incorporated, respectively.

Drug Release from PAT-DS Coated Balloons

The standard time frame required for drug transfer from the balloons for treating peripheral vascular disease is 3 minutes. Therefore, the balloon inflations of up to 180 seconds are recommended for peripheral artery devices. Hence, 3 minutes is used as the typical time for balloon inflation and treatment (after the initial 1 minute time point—which is the typical time period for balloon tracking) in the drug release studies conducted using PAT-DS coated balloons.

The total amount PAT loaded on the PAT-DS coated balloons for low, medium and high doses of PAT incorporated were determined as 0.7±0.03 µg/mm², 1.2±0.1 µg/mm², and 2.2±0.2 µg/mm², respectively. The cumulative release and the percentage of PAT released at different time points are provided in FIGS. 11A and 11B, respectively. Only 10-20% of the total drug loaded was released for up to 1 min. Then, ~80% of the total drug loaded was released between 1 min and 4 min (for a total time interval of 3 mins). After 4 min, only 5-10% of the drug was retained. This suggested that the PAT-DS coatings have the potential to be used in DCBs to reduce early drug loss during the typical time period of balloon tracking (up to 1 min) and then to immediately deliver a clinically relevant dose of drug during the typical time period of balloon inflation and treatment (from 1 min to 4 min).

Discussion

In this example, PAT incorporated DS films were prepared by solvent-casting method using solvents such as water/ethanol and water/DMSO. Differences in tensile strength and modulus were observed between the PAT-DS films prepared by water/ethanol and water/DMSO. However, no significant differences in the film elasticity, drug elution or cell response were observed between the films prepared by different solvent combinations. In this example, both the control DS and PAT-DS films have shown a dose-dependent inhibitory effect. Although the higher dose of DS can provide an inhibitory effect, which is comparable to that of PAT-DS, the incorporation of PAT is still beneficial for providing long-term inhibitory effect especially in in vivo conditions. This is due to (a) rapid uptake of PAT in the vessel wall because of the lipophilic nature of the drug; (b) prolonged retention of PAT in the vessel wall because of the hydrophobic nature of the drug. Also, once the DS is released, it could be washed away in the blood stream due to its hydrophilic properties. Hence, the use of PAT in DCBs is helpful for providing inhibitory effect over a long period of time.

Although there was a difference in the thickness observed between the two-dimensional (2D) PAT-DS films (600-800 μm) and PAT-DS coatings (120-150 μm) on the balloons, it did not affect the mechanical or drug release properties of PAT-DS coatings on the balloons. The integrity of PAT-DS coatings on balloons was well-maintained without any mechanical defects when the balloons were either deflated or inflated, suggesting that the PAT-DS coatings have the required mechanical properties to withstand the stress created during balloon inflation or deflation. The drug release studies of PAT-DS coated balloons showed that only a minimal amount (10-20%) of the total drug loaded was released during the typical time period of balloon tracking (1 min) while most of the remaining drug (~80%) was released during the typical time period of balloon inflation and treatment (from 1 min to 4 min, for a total time interval of 3 mins). This was in agreement with the drug release profiles observed for 2D PAT-DS films, which were totally dissolved in 5 mins. The total amount of drug loaded on the balloons can be adjusted by varying the concentration of drug in the coating solutions used. Hence, irrespective of the coating procedure (dip-coating followed by dehydration and rapid drying vs. solvent casting) and coated surface (balloons vs. glass petri dish), the PAT-DS platform showed promising results for applications in DCBs.

Conclusions

In this study, PAT-DS films, and PAT-DS coatings on balloons were prepared, characterized, and investigated for their applications in DCBs. A solvent-casting method was used to prepare PAT-DS films using solvents, water/ethanol and water/DMSO. SEM showed that all the PAT-DS films prepared were smooth and homogeneous with PAT molecularly dispersed in the DS matrix. FTIR showed that the PAT was successfully incorporated into the bulk of DS with negligible amount of drug present on the film surface. DSC showed that the PAT was present in amorphous form inside the DS matrix. Although some differences in the tensile properties were observed between the films prepared by ethanol and DMSO, all the films showed excellent ductility, which is an important property for using this material as a coating for DCBs. Both the Ctrl-DS and PAT-DS films inhibited the growth of SMC in a dose-dependent manner with the superior inhibitory effect observed for PAT-DS films. The PAT-DS coatings on the balloon catheters showed an excellent integrity without any mechanical defects observed when the balloons were either deflated or inflated. A PAT dose of up to 2.2 μg/mm$^2$ was loaded on the balloons using DS platform. Only 10-20% of the total drug loaded was released from the PAT-DS coated balloons during the typical time period of balloon tracking (1 min). This was immediately followed by a delivery of ~80% of the total drug loaded during the typical time period of balloon inflation and treatment (from 1 min to 4 min). Thus this study demonstrated the use of PAT-DS as a drug delivery platform for DCBs.

Example 2

This example is focused on developing paclitaxel (PAT) loaded polyethylene oxide (PEO) films (PAT-PEO) as a controlled drug delivery carrier for DCBs. An array of PAT-PEO films were developed in this study to provide tailored release of >90% of drug only at specific time intervals, which is the time frame for carrying out balloon-based therapy. The characterizations of PAT-PEO films using SEM, FTIR, and DSC showed that the films developed were homogenous and the PAT was molecularly dispersed in the PEO matrix. Mechanical tests showed that most PAT-PEO films developed were flexible and ductile, with yield and tensile strengths not affected after PAT incorporation. The viability, proliferation, morphology, and phenotype of smooth muscle cells (SMCs) interacted with control-PEO and PAT-PEO films were investigated. All control-PEO and PAT-PEO films showed a significant inhibitory effect on the growth of SMCs, with the degree of inhibition strongly dependent on the w/v % of the polymer used. The w/v % of PEO and wt % of PAT were varied to obtain different groups of PAT-PEO films that show tailored release of >90% of drug only at specific time intervals. The PAT-PEO coating was produced on the balloons. The integrity of PAT-PEO coating was well maintained without any mechanical defects occurring during balloon inflation or deflation. The drug release studies showed that only 15% of the total PAT loaded was released from the balloons within the initial 1 min (typical balloon tracking time), whereas 80% of the PAT was released between 1 min and 4 min (typical balloon treatment time). Thus, this study demonstrated the use of PEO as an alternate drug delivery system for the balloons.

Materials

Poly(ethylene oxide) (PEO, average My 100,000 Da), ethanol (200 proof), methanol, phosphate-buffered saline with 0.05 wt % tween-20 (PBS/T-20), Dulbecco's phosphate-buffered saline (DPBS), fluorescein diacetate (FDA), tris-buffered saline (TBS), propidium iodide (PI), HPLC-grade water and acetonitrile, urea, polysorbate, sorbitol, and shellac were all purchased from Sigma-Aldrich (USA). Iodixanol (contrast agent) was purchased from GE Healthcare Inc. (Princeton, N.J.). Paclitaxel (PAT) was purchased from ChemieTek (Indianapolis, Iowa). All chemicals purchased were used as received.

Preparation of PAT Loaded PEO Films and Control PEO Films

PAT loaded PEO (PAT-PEO) films were prepared in this study using the solvent casting method. Initially, the PEO (10%, w/v) was dissolved in de-ionized water (di-H$_2$O) by stirring the polymer in the solvent at 200 rpm for 6 hrs. In parallel, a solution of PAT was prepared in ethanol by sonicating the drug in the solvent for 5 mins thrice. The PAT solution (10 mg/mL) prepared was then added dropwise into the PEO solution at 1.5 wt %, and the drug-polymer mixture was stirred at 200 rpm for 18 hrs. The drug-polymer mixture solution was then poured into a petridish (8.8 cm in diameter) and heated in an oven at 50° C. under vacuum (−20 inHg) for 48 hrs. The oven was then turned off and the samples were left inside the oven for 30 mins to slowly cool the samples. The petridish was then removed from the oven and the PAT-PEO films formed were peeled off using a razor. The PAT-PEO films were then cut into specimens of varying sizes for performing different characterizations.

Similar experiments were carried out for preparing PAT-PEO films with 15, 20, and 25 w/v % of PEO. However, there was no change made in the concentration (10 mg/mL) or volume (3 mL) of PAT solution that was added to the different w/v % PEO. This led to PAT loadings of 1.0, 0.75, and 0.6 wt % in PEO (15%, w/v), PEO (20%, w/v), and PEO (25%, w/v) films, respectively. Thus, the PAT-PEO films prepared in this study with 10 w/v % of PEO and 1.5 wt % of PAT, 15 w/v % of PEO and 1.0 wt % of PAT, 20 w/v % of PEO and 0.75 wt % of PAT, and 25 w/v % of PEO and 0.6 wt % of PAT are referred to as PAT-PEO-10, PAT-PEO-15, PAT-PEO-20, and PAT-PEO-25, respectively. Table 2A shows the polymer weight, solvent volume, drug solution volume, and stirring speed used in the preparation of these four different groups of PAT-PEO films.

loose to handle at a time point, it was permanently placed in the PBS/T-20 solution used for that respective time point without transferring to the next time point. The time point at which the film was permanently placed in the PBS/T-20 solution was regarded as the final time point for that particular group of PAT-PEO film. The final time points for PAT-PEO-10, PAT-PEO-15, PAT-PEO-20, and PAT-PEO-25 groups were 2 min, 5 min, 5 min, and 7 min, respectively. The PBS/T-20 samples collected at each time point were then used for determining the amount of PAT released using high performance liquid chromatography (HPLC). Prior to HPLC analysis, 1 mL of ethanol was added to the plastic tubes in which the PBS/T-20 samples were collected and shaken well for 30 seconds. This ethanol addition step was carried out as a standard procedure to remove any PAT that was physically bound to the plastic tube surfaces[9, 10]. The HPLC method for determining PAT released was carried out as reported previously[11, 12].

Characterization of PAT-PEO and Control PEO Films

All PAT-PEO and control PEO films prepared in this study were characterized using scanning electron microscopy (SEM), optical surface profilometry (OSP), Fourier trans-

TABLE 2A

Polymer weight, solvent volume, drug solution volume, and stirring speed used in the preparation of four different groups of PAT-PEO films.

| PAT-PEO film groups | PEO (wt/vol %) | PAT (wt %) | Weight of PEO (grams) | Volume of di-H$_2$O (mL) | Volume of PAT solution in mL (drug concentration is 10 mg/mL) | Stirring speed* during mixing (rpm) |
|---|---|---|---|---|---|---|
| PAT-PEO-10 | 10 | 1.5 | 2 | 17 | 3 | 200 |
| PAT-PEO-15 | 15 | 1 | 3 | 17 | 3 | 200 |
| PAT-PEO-20 | 20 | 0.75 | 4 | 17 | 3 | 175 |
| PAT-PEO-25 | 25 | 0.6 | 5 | 17 | 3 | 50 |

*Stirring speed was decided depending on the viscosity of the solution. For instance, a stirring speed of 200 rpm was required for an even mixing of PAT-PEO-10 solution. However, for PAT-PEO-25, which is highly viscous when compared to other PAT-PEO solutions, the stirring speed has to be significantly reduced to 50 rpm for even mixing. Control PEO films (without PAT loaded) were also prepared at four different w/v % (10, 15, 20, and 25). The protocols for preparing these control films were similar to the above mentioned procedure without the addition of PAT (Table 2B).

TABLE 2B

Polymer weight, solvent volume, and stirring speed used in the preparation of four different groups of control PEO films.

| Control PEO film groups | PEO (wt/vol %) | PAT (wt %) | Weight of PEO (grams) | Volume of di-H$_2$O (mL) | Volume of PAT solution in mL (drug concentration is 10 mg/mL) | Stirring speed during mixing (rpm) |
|---|---|---|---|---|---|---|
| PEO-10 | 10 | 0 | 2 | 20 | 0 | 200 |
| PEO-15 | 15 | 0 | 3 | 20 | 0 | 200 |
| PEO-20 | 20 | 0 | 4 | 20 | 0 | 175 |
| PEO-25 | 25 | 0 | 5 | 20 | 0 | 50 |

Drug-Elution Studies

For the drug-elution studies, the PAT-PEO film specimens (0.5 cm×0.5 cm) were immersed in 25 mL of PBS/T-20 solution and incubated in a circulating water bath (Thermo Scientific, USA) at 37° C. As a standard protocol, Tween-20, a non-ionic surfactant, was added in the release medium to increase the solubility of PAT in PBS and to maintain sink conditions [9, 10]. At each pre-determined time point (30 sec, 1 min, 2 min, 3 min, 5 min, and 7 min), the films were taken out of the solution and transferred to a fresh PBS/T-20 solution. Due to the inherent water solubility of PEO, the films started to turn loose at different time points depending on the group of PAT-PEO film. When the films turned too form infrared spectroscopy (FTIR), and differential scanning calorimetry (DSC). A Quanta 450 SEM (FEI, USA) was used to image the morphology of surfaces as well as the cross-sections of PAT-PEO and control PEO films. For SEM imaging, 10 kV and 30 kV accelerating voltages were used for obtaining surface and cross-sectional images, respectively. Prior to SEM analysis, the films were sputter-coated with a 15 nm thick gold-palladium to avoid surface charging. A Wyko NT8000 OSP (Broker Corporation; operated at Michigan Metrology, LLC) was used in this study to obtain 3D topography images of control PEO and PAT-PEO specimens. A Nicolet 6700 FTIR spectroscopy (Thermo Scientific, USA) equipped with an attenuated total reflection (ATR) accessory was used to characterize the surfaces of PAT-PEO and control PEO films. The FTIR spectra of PAT and PEO in powder forms were also obtained. All FTIR spectra were collected at 1024 scans with a spectral resolution of 4 cm$^{-1}$. All collected spectra were analyzed using OMNIC® software. A Q200 DSC (TA instruments, New Castle, Del.) was used in this study to characterize all PAT-PEO and control PEO films. PEO and PAT in powder forms were also characterized using DSC. For this characterization, a sample weighing 8-10 mg was sealed in an aluminum plan and heated to 300° C. at a scan rate of 10° C./min. As a reference, an empty aluminum pan was used. All DSC measurements were carried out under nitrogen gas at a flow rate of 40 mL/min.

Mechanical Testing of PAT-PEO and Control PEO Films

An MTS insight electromechanical instrument (MTS System Corp., Eden Prairie,

MN) was used in this study to characterize all PAT-PEO and control PEO film specimens (1 cm×7 cm, n=3 for each sample group). The thickness of the specimens was determined using SEM. The specimens were gripped at a length of 1 cm from each end and stretched to failure using a 100 N load cell at 50 mm/min extension rate. A TESTWORKS® 4 software was used to determine the elastic modulus, strain at break, peak load, and tensile strength from the stress-strain curves obtained for the films.

Characterization of PAT-PEO Films Post Drug-Elution Studies

To determine the drug delivery mechanism, the PAT-PEO films used in the drug-elution studies were characterized using FTIR and DSC to observe the changes occurred in the chemical composition and crystallinity of the films, respectively. Also, the films were immersed in 2 mL of PBS/T-20 at 37° C., and real-time images were obtained using phase contrast microscopy to observe the morphological changes of the films.

Smooth Muscle Cell (SMC) Cultures

Human aortic smooth muscle cells (HASMCs, catalog no. 354-05a) and smooth muscle cell growth medium (catalog no. 311-500) were obtained from Cell Applications (San Diego, Calif.). The cells were cultured in the growth medium at 37° C. in a humidified 5% $CO_2$ incubator. The cells obtained from passages four to six were used in this study. Initially, a density of 15×10$^3$ cells (in 1000 µL of growth medium) was allowed to grow in the wells of a 24-well tissue culture plate for 24 hrs. The used media were then removed and 1000 µL of fresh growth media were added to the wells. Then, PAT-PEO or control-PEO film specimens (1 cm×1 cm) were added to the cells grown in the wells. After 18 hrs (on day-1), the used media were removed and 1000 µL of fresh growth media were added to the wells. The media were changed again on day-3 and day-5. A control experiment was also carried out as the cells were allowed to grow in the wells in the absence of either PAT-PEO or control-PEO films.

Smooth Muscle Cell Viability and Proliferation

The resazurin cell viability assay kit (trademark name AlamarBlue) was purchased from Biotium (Hayward, Calif.) and used to quantitatively measure the viability and proliferation of cells [13, 14]. At pre-determined time points (day-1, 3, and 5), the used media were removed and a solution containing the mixture of resazurin (100 µL) and cell culture medium (900 µL) was added to the cells. Then, the cells were incubated in the solution at 37° C. in the dark for 6 hrs. The fluorescence of the solution was measured using a Tecan INFINITE® M200 microplate reader (Tecan Group Ltd, Mannedorf, Switzerland) at excitation and emission wavelengths of 530 nm and 590 nm, respectively. The fluorescence of the blanks (cell growth medium and resazurin, without cells) was also obtained and the value was subtracted from the fluorescence values of the experimental samples. The values reported here are the corrected fluorescence values. For the cell viability and proliferation study, three samples were used for each of the eight groups (four groups of PAT-PEO and four groups of control PEO) at each time point (1, 3, and 5 days). Therefore, 72 samples were used in this part of the study.

Smooth Muscle Cell Morphology

The morphology of SMCs was characterized as reported previously[13, 14]. Briefly, a stock solution of fluorescein diacetate (FDA) was prepared at a concentration of 1 mg/mL in acetone. The working solution was prepared by adding 100 µL of the prepared FDA stock solution to 900 µL of DPBS. After 1, 3, and 5 days, the used media were removed, and a solution containing 60 µL of the FDA working solution and 1000 µL of DPBS was added to the cells. Then, the cells were incubated in the solution at −20° C. in the dark for 15 min. An AXIOVERT® 200 M inverted fluorescence microscope (Carl Zeiss Microscopy, Thornwood, N.Y.) was used to image the cells. For the morphology study also, three samples were used for each of the eight sample groups at each of the three time points. Hence, 72 samples were used for this part of the study as well. The fluorescence images were obtained at a minimum of four different spots on each sample and the representative images of each sample group are provided here. The SMC size was quantitatively determined by calculating its aspect ratio using the ImageJ software. The aspect ratio of cells was defined as the ratio of length of major axis to the length of minor axis, with 1.0 being a complete circle. For each experimental group at each time point, three images were used for analysis. In each image, an aspect ratio of at least 10 cells was calculated. Hence, a total of 30 cells per group per time point was measured for the analysis.

Smooth Muscle Cell Phenotype

Triton X-100, goat serum, α-actin antibody (1A4), and goat anti-mouse IgG-FITC were all purchased from Santa Cruz Biotechnology (Santa Cruz, Calif.). The SMC phenotype was characterized as reported previously[14]. Briefly, the cells treated with control PEO films or PAT-PEO films or no films (control wells) were allowed to grow for 3 days. Then, the cells were washed with DPBS twice and fixed using 4% paraformaldehyde (Affymetrix, Santa Clara, Calif.) at room temperature (RT) for 10 min. The cells were then washed with DPBS five times for 3 min each and incubated in a permeabilizing solution (0.1% Triton X-100 in tris-buffered saline) for 25 min at RT. The cells were subsequently washed with DPBS followed by incubating in blocking buffer (10% of goat serum in permeabilizing solution) for 25 min at RT. Then, the cells were washed with DPBS and incubated in α-actin primary antibody diluted 1:50 with 1.5% goat serum in DPBS for 90 min at RT. After washing with DPBS five times for 5 min each, the cells were incubated in goat anti-mouse IgG-FITC secondary antibody diluted 1:75 with 1.5% goat serum in DPBS for 60 min at RT in the dark. The cells were then washed with DPBS five times for 5 min each and incubated in 2% propidium iodide (PI) in DPBS for 15 min at RT in the dark to stain the nucleus. A laser scanning confocal microscope (Nikon, Melville, N.Y.) was then used to image the cells. The immunofluorescence microscopy images obtained were analyzed for the quantification of smooth muscle α-actin in the cells using ImageJ software as described previously [15-17]. Briefly, the fluorescence intensity of the green color stained α-actin was measured. Also, the fluorescence intensity of the background (spots in the images where there are no cells) was measured. Once the integrated density of the cell was calculated, the corrected total cell fluorescence (CTCF) was determined using the following formula: CTCF=Integrated density−(Area of selected cell×Mean fluorescence of background readings). The CTCF determined was used as a proxy for the amount of SM alpha-actin in the cells as described previously [15-17]. For each group, at least 15 cells were used for analysis.

Preparation of PAT-PEO Coating on Balloons

The PAT-PEO solution was prepared as described above with 10 w/v % of PEO and 4.5 wt % of PAT. Angioplasty balloon catheters (ev3 Inc., USA) of 2 mm in diameter×20 mm in length were used for the experiments. The balloons were initially inflated with an air pressure of 6-8 atm. Then, the inflated balloons were dipped in the prepared PAT-PEO solution (PAT concentration—4.5 mg/mL) for 1 min followed by transferring them into an oven and heat treated in air at 50° C. for 1 hr. The balloons were then taken out and dipped again in PAT-PEO solution for 15 sec followed by heat treatment in air at 50° C. for 1 hr. This step was again repeated twice.

Preparation of Control DCBs Using Currently Available DCB Coating Combinations

Currently available coating combinations of DCBs include PAT only (without any excipient), and drug-excipient combinations such as PAT-urea, PAT-polysorbate/sorbitol, PAT-shellac, and PAT-contrast agent [18]. In this study, five control DCBs were prepared using these coating combinations. Except the control PAT only (without any excipient), all other drug-excipient combination solutions were prepared with a ratio of 1:1 (drug:excipient). The solvents used for preparing these solutions are either ethanol only (for PAT only and PAT-shellac) or ethanol:di-$H_2O$ (50:50, v/v, for PAT-urea, PAT-polysorbate/sorbitol, and PAT-contrast agent). The concentration of PAT in all these solutions was kept as 4.5 mg/mL. The balloons were coated with these solutions using the same dip coating procedure as described in section 2.8.

SEM Imaging of PAT-PEO Coated Balloons and Control DCBs

The PAT-PEO coated balloons (section 2.8) and the five control DCBs prepared were imaged using a SEM at three different positions including as-coated position, deflated position, and inflated position. Also, a bare balloon without any coatings was imaged in its inflated and deflated positions. An accelerated voltage of 1 kV was used to obtain the images at several different locations of the balloons.

Drug-Elution Studies of PAT-PEO Coated Balloons and Control DCBs

The PAT-PEO coated balloons and control DCBs were deflated prior to drug-elution studies. Then, the deflated balloons were immersed in 50 mL of PBS/T-20 solution and incubated in a circulating water bath at 37° C. The balloons were removed from the solution and transferred to a fresh PBS/T-20 solution at pre-determined time points (30 sec, 1 min, 2 min, 3 min, 4 min, 5 min, and 7 min). After the 1 min time point, the balloons were inflated with an air pressure of 6-8 atm and remained inflated for the time points thereafter. After 7 min, the balloons were taken out and sonicated in a 20 mL solution containing di-$H_2O$ and ethanol (50:50, v/v) for 1 min to remove any residual drug present on the balloon. All solutions collected were analyzed for the amount of PAT released using HPLC.

Statistical Analysis

All experiments conducted in this study were repeated at least thrice using different film batches. The experimental data collected in this study are presented as mean±standard deviation. A one-way analysis of variance (ANOVA) was used to determine the statistical significance at $p<0.05$.

Results

Drug Release from PAT-PEO Films

FIG. 12A shows the percentage of PAT released at different time point intervals for the four different groups of PAT-PEO films prepared in this study. For PAT-PEO-10, the percentage of drug released was less than 3% for up to 1 min. However, the remaining ~97% of the drug was released from this group of films between 1-2 min. For PAT-PEO-15, only <4% of the drug was released by 2 min. However, the remaining ~90% of the drug was released from this group of films between 2-3 min. For PAT-PEO-20, only ~6% of the drug was released for up to 3 min. However, the remaining ~94% of the drug was released from this group of films between 3-5 min. Similarly, for PAT-PEO-25, only <8% of the drug was released for up to 5 min. However, the remaining ~92% of the drug was released from this group of films between 5-7 min. These results strongly demonstrated that the release of PAT from PEO films can be tailored to deliver ≥90% of drug only at specific time intervals of interest with <10% of the drug released at any other time points.

The total amount of PAT loaded in different groups of PAT-PEO films is provided in Table 3. FIG. 12B shows the amount of drug released from four different groups of PAT-PEO films at different time points. For PAT-PEO-10, a drug dose of 4.5±0.2 µg/mm$^2$ was released between 1-2 min. Similarly, for PAT-PEO-15, PAT-PEO-20, and PAT-PEO-25, the drug doses of 2.5±0.5 µg/mm$^2$, 3.2±0.1 µg/mm$^2$, and 3.0±0.4 µg/mm$^2$ were released between 2-3 min, 3-5 min, and 5-7 min, respectively. Only a trace amount of drug (<0.3 µg/mm$^2$) was released from all these groups of films at any other time points used in the study. Several clinical studies in the literature have previously shown that a dose of 2 to 3 µg/mm$^2$ was effective in successfully inhibiting restenosis in patients with peripheral vascular disease [6, 18, 19]. Based on these literature, the doses of PAT released from PAT-PEO films prepared in this study are clinically relevant for inhibiting restenosis.

TABLE 3

Total amount of drug (µg/mm$^2$) loaded in PAT-PEO films.

| Sample group | rug loaded (µg/mm$^2$) |
|---|---|
| PAT-PEO-10 | 4.6 ± 0.2 |
| PAT-PEO-15 | 2.8 ± 0.5 |
| PAT-PEO-20 | 3.4 ± 0.2 |
| PAT-PEO-25 | 3.2 ± 0.5 |

SEM Characterization of Control PEO and PAT-PEO Films

FIG. 13 shows the SEM images of surfaces and cross-sections of control PEO and PAT-PEO films prepared in this study. The surfaces of both the control PEO and PAT-PEO films were homogenous with small fissures present on the surfaces (FIG. 13A-H). Also, all PAT-PEO film surfaces (FIG. 13E-H) appeared smoother than their corresponding control PEO film surfaces (FIG. 13A-D). The cross-sections of control and PAT-PEO films were also homogenous (FIG. 13I-P). Using SEM cross-sectional images, the thickness of PEO-10, PEO-15, PEO-20, PEO-25, PAT-PEO-10, PAT-PEO-15, PAT-PEO-20, and PAT-PEO-25 films was determined as 263±64 µm, 342±74 µm, 445±77 µm, 517±45 µm, 200±43 µm, 322±36 µm, 413±18 µm, and 495±26 µm, respectively. Similar to the surface, the cross-sections of PAT-PEO films (FIG. 13 M-P) were smoother than that of their corresponding control PEO films (FIG. 13 I-L). This could suggest that the PAT acted as a filler by bridging the space between PEO polymeric chains to smoothen the PAT-PEO films. Also, no PAT crystals were present on the surface of PAT-PEO films (FIG. 13 E-H). This suggested that the PAT was successfully incorporated into the bulk of PEO films. The cross-sections of PAT-PEO films also did not show the presence of PAT crystals (FIG. 13 M-P). This suggested that the PAT was molecularly dispersed in PEO with no crystals formed inside the films irrespective of the type of PAT-PEO films prepared in this study.

OSP Characterization of Control PEO and PAT-PEO Films

3D OSP topography images of control and PAT-PEO films were generated (data not shown). These images showed how the PEO crystals were distributed on the films. For the PEO-10 and PEO-15 films, the crystals were loosely scattered with some crystals merging together. However, for the PEO-20 and PEO-25 films, the crystals were densely packed with many of them merging together. For the PAT-PEO-10 and PAT-PEO-15 films, the crystals were denser than that of their corresponding control PEO films. For the PAT-PEO-20 and PAT-PEO-25 films, the crystals were larger and denser than that of their corresponding control PEO films. Table 4 shows the average surface roughness ($S_a$) of control PEO and PAT-PEO films. Irrespective of control PEO or PAT-PEO films, the surface roughness of the films prepared with 20 and 25 w/v % of the polymer was four times lower than that of the films prepared with 10 and 15 w/v % of the polymer. This suggested that the films prepared with higher w/v % (20 and 25) are smoother than that of the films prepared with lower w/v % (10 and 15). Also, the surface roughness of PAT-PEO films was lower than that of their corresponding control-PEO films especially when the films were prepared with higher w/v % (20 and 25). This result further emphasizes that the addition of PAT improves the smoothness of the films.

TABLE 4

Average surface roughness ($S_a$) of control PEO films and PAT-PEO films measured at 511 µm × 510 µm field of view.

| Sample group | $S_a$ (µm) |
|---|---|
| PEO-10 | 10.3 ± 2.8 |
| PEO-15 | 11.2 ± 3.0 |
| PEO-20 | 2.7 ± 0.3 |
| PEO-25 | 2.3 ± 0.6 |
| PAT-PEO-10 | 9.1 ± 2.4 |
| PAT-PEO-15 | 9.3 ± 0.6 |
| PAT-PEO-20 | 0.9 ± 0.1 |
| PAT-PEO-25 | 1.3 ± 0.2 |

FTIR Characterization of Control PEO and PAT-PEO Films

FTIR spectra of PEO and PAT in powder forms were obtained (data not shown). For the PEO powder, a large peak observed at 2878 $cm^{-1}$ was assigned for the C—H stretching of methylene groups in the polymer. The peaks for scissoring, wagging, twisting, and rocking modes of —$CH_2$ groups were observed at 1466 $cm^{-1}$, 1359 and 1341 $cm^{-1}$, 1279 and 1241 $cm^{-1}$, and 961 and 841 $cm^{-1}$, respectively. The three peaks observed at 1145, 1094, and 1059 $cm^{-1}$ were assigned for the C—O—C stretches of PEO. For the PAT powder, the strong peaks for the C=O functionality of ester, ketone, and amide groups were observed at positions 1733, 1704, and 1645 $cm^{-1}$, respectively. Also, the peaks for the fingerprint region of PAT were observed at 1241, 1176, 1071, 985, and 704 $cm^{-1}$. The IR peaks and their positions of PEO and PAT powders are in well agreement with the literature [20-23].

The IR peaks and their positions observed for all PEO films prepared in this study are in excellent agreement with those of PEO powder. This indicated that the incorporation of PAT did not affect the chemical structure of PEO. Also, no IR peaks for PAT were observed in the spectra of PAT-PEO films. This is also in agreement with the SEM results that the PAT was incorporated into the bulk of PEO films and was not present on the film surfaces.

DSC Characterization of Control PEO and PAT-PEO Films

DSC thermograms of PEO and PAT in powder forms were obtained. The melting point of PEO powder was observed at 69° C. For PAT powder, an endothermic melting peak was observed at 221° C., which was immediately followed by an exothermic decomposition peak at 231° C. For the control PEO films and PAT-PEO films, there was no significant shift in the melting point of PEO. This suggested that the crystallinity of PEO was not affected either when the polymer was made into a film or after the drug was incorporated into the polymer film. Also, no peak for PAT was observed in any of the PAT-PEO films. This is because of the less weight percentages of drug loaded (1.5%, 1%, 0.75%, and 0.6%) in the polymer. Previous studies have shown that the DSC peak for the drug loaded in the polymer was absent when the wt % of drug loaded was lesser than 5% [24].

Mechanical Properties

FIG. 14 shows the stress-strain curves of control PEO and PAT-PEO films prepared in this study. Elastic modulus is the measure of stiffness or rigidity of a material. A stiff material has a high elastic modulus while a flexible material has a low elastic modulus. In this study, after the incorporation of PAT in PEO, the PAT-PEO-10 had a 23% higher elastic modulus than that of control PEO-10 (Table 5). However, PAT-PEO-15, 20, and 25 had a 10%, 29%, and 21% smaller elastic modulus than that of control PEO-15, 20, and 25, respectively. These results suggested that the incorporation of drug in PEO increases the flexibility of films except for the films prepared with 10 w/v % of polymer. Strain at break is the measure of ductility of materials. PAT-PEO-10, 15, 20, and 25 films showed 140%, 29%, 74%, and 62% increased strain at break when compared to their corresponding control PEO films (Table 5). This suggested that the incorporation of drug makes the films more ductile. The peak load is directly related to yield strength, which determines how much stress a sample can withstand before it plastically deforms. The peak load for PAT-PEO-10 was significantly greater (53%) than that of PEO-10 (Table 5). However, for the films prepared with 15, 20, and 25 w/v % of polymer, no significant difference in peak load was observed between control PEO and PAT-PEO. These results suggested that the incorporation of drug did not negatively affect the yield strength of the material. Tensile strength is the maximum amount of stress that a material can withstand before breaking. Hence, the greater the tensile strength, the stronger the material. The tensile strength for PAT-PEO-10 was significantly greater (97%) than that of PEO-10 (Table 5). This suggested PAT-PEO-10 was stronger than PEO-10. However, for the films prepared with 15, 20, and 25 w/v % of polymer, no significant difference in tensile strength was observed between control PEO and PAT-PEO. These results suggested that the incorporation of drug did not negatively affect the strength of the films.

TABLE 5

Mechanical properties of control PEO films and PAT-PEO films.

| Sample group | Elastic modulus (MPa) | Strain at break (%) | Peak load (lbf) | Tensile strength (MPa) |
| --- | --- | --- | --- | --- |
| PEO-10 | 279 ± 21 | 1.5 ± 0.1 | 1.9 ± 0.2 | 3.3 ± 0.4 |
| PEO-15 | 399 ± 39 | 2.4 ± 0.2 | 4.1 ± 0.5 | 5.3 ± 0.7 |
| PEO-20 | 527 ± 72 | 1.9 ± 0.3 | 6.5 ± 1.2 | 6.5 ± 1.2 |
| PEO-25 | 541 ± 43 | 2.1 ± 0.5 | 6.4 ± 0.1 | 5.5 ± 0.1 |
| PAT-PEO-10 | 342 ± 34 | 3.6 ± 0.6 | 2.9 ± 0.4 | 6.5 ± 0.9 |
| PAT-PEO-15 | 358 ± 49 | 3.1 ± 0.8 | 3.4 ± 0.4 | 4.7 ± 0.6 |
| PAT-PEO-20 | 373 ± 46 | 3.3 ± 0.1 | 5.0 ± 0.8 | 5.3 ± 0.8 |
| PAT-PEO-25 | 426 ± 58 | 3.4 ± 0.4 | 6.0 ± 0.8 | 5.4 ± 0.7 |

Characterization of PAT-PEO Films Post Drug-Elution Study

FTIR characterization of PAT-PEO-10, PAT-PEO-15, PAT-PEO-20, and PAT-PEO-25 films were collected after 1 min, 2.5 min, 3.15 min, and 6 min of drug-elution studies, respectively, are provided in FIG. 15A. The peaks for the different functionalities of PEO such as C—H (2918 cm$^{-1}$), —CH (1457, 1355, 1245, and 948 cm$^{-1}$), and C—O—C (1081 cm$^{-1}$) were observed. This shows that the chemical structure of PEO molecules was not altered in the specimens (loose disintegrated films) collected after drug-elution studies. These results suggested that the drug release from PAT-PEO films occurred due to dissolution of films and not due to biodegradation of polymer. A broad peak observed at 3370 cm$^{-1}$ was due to H$_2$O molecules absorbed in the films during its immersion in PBS/T-20 solution. Also, the peaks observed at 1645 cm$^{-1}$ and 1733 cm$^{-1}$ were assigned to the C=O functionality of amide and ester groups of PAT delivered from the films, respectively. FIG. 15B shows the DSC thermograms of PAT-PEO films collected after the drug-elution studies. The thermograms showed two peaks between 100° C. and 125° C. due to evaporation of free and bonded water from the films. However, no melting peak for the PEO crystals was observed at 65-70° C. This strongly suggested that all PEO crystals were disintegrated under the conditions used for drug-elution studies. These results further emphasized that the drug was delivered from the PAT-PEO films due to dissolution of films. FIG. 15C shows the real-time images of PAT-PEO films obtained using phase contrast microscopy at different time points. Prior to its immersion in PBS/T-20, the films were intact as it appeared mostly dark. The films absorbed most of the light and reflected little to appear mostly dark. However, after immersion in PBS/T-20, the PAT-PEO-10, 15, 20, and 25 films disintegrated at 2, 3, 5, and 7 mins, respectively, as it is evident from the images which were mostly bright. The disintegrated films absorbed very little light to appear mostly bright. Thus, these results were in excellent agreement with FTIR and DSC to suggest that the drug was delivered from PAT-PEO films mainly due to dissolution of films.

Cell Viability and Proliferation

The viability and proliferation of SMCs treated with control PEO films, PAT-PEO films, and no films (control wells) are provided in FIG. 16. The cells in the control well containing no films proliferated profusely from one time point to the other. It was interesting to observe that all of the control PEO films significantly inhibited (64%-76% decrease) the growth of SMCs compared to that of control wells. Also, for the control PEO films, an increase in the inhibitory effect was observed as the w/v % of PEO increased. This suggested that the PEO alone (without the drug) can significantly inhibit the growth of SMCs with greater inhibition rate observed for the films with larger w/v % of the polymer. For PAT-PEO, all films significantly inhibited (79%-86% decrease) the growth of SMCs when compared to that of the control well. Also, most of the PAT-PEO films showed greater inhibitory effect (35%-50% decrease) than their corresponding control PEO films (day-5 in FIG. 16). Although the wt % of drug was lesser (0.6%) in PAT-PEO-25, these films showed maximum inhibitory effect when compared to that of all other films prepared in this study. This could be due to the combined effect of larger w/v % of polymer and the presence of drug. Thus, these results demonstrated that the PAT-PEO films prepared in this study effectively inhibited the growth of smooth muscle cells.

Cell Morphology

Fluorescent microscopy images of FDA stained SMCs treated with control PEO films, PAT-PEO films, and no films (control wells) at days 1, 3, and 5 were obtained (data not shown). In the control well, the SMCs were elongated with its characteristic spindle-shape and hill-and-valley morphology. The cells treated with control PEO films mostly showed an irregular morphology on day-1. However, by day-5, the cells treated with control PEO films started to show the normal spindle-shaped morphology. This could suggest that PEO alone may not provide the long-term inhibitory effect. Hence, the incorporation of anti-proliferative agents is crucial for providing long-term inhibitory effect to these films. Also, an increasing number of normal spindle-shaped cells were observed for the films prepared with lower w/v % (10 and 15) of polymer than the films prepared with higher w/v % (20 and 25) of polymer. (This further emphasizes that higher w/v % of polymer has greater inhibitory effect on SMCs. For all PAT-PEO films, the cells displayed an uncharacteristic discoid (flat circular) morphology for all time points used in this study. After 5 days, the confluency of SMCs in the control well, control PEO-10, 15, 20, and 25 films were estimated as 90-95%, 50-60%, 50-60%, 20-25%, and 20-25%, respectively. For all four PAT-PEO groups, very few viable cells were only observed after day-5 with <10% confluency. These qualitative data are in excellent agreement with the quantitative results described herein On day-1, the aspect ratio of SMCs treated with PAT-PEO films (1.3-1.5) and most PEO films (1.7-2.0 for PEO-15, 20, and 25) are twice smaller than that of the controls (no films) (5.0±2.0). The range of aspect ratio of the cells in controls remained same for up to day-5. Similarly, the range of aspect ratio of the cells treated with PAT-PEO films remained same for up to day-5. However, the cells treated with control PEO films showed an increase in aspect ratio from day-1 to day-5. On day-5, there was no significant difference observed in the aspect ratio of cells treated with control PEO films and controls.

Cell Phenotype

Smooth muscle (SM) α-actin is a cytoskeletal protein that is primarily responsible for the motility, structure, and integrity of SMCs [25]. A strong expression of SM α-actin is usually observed for well growing SMCs. Also, the α-actin filaments orient along the cell axis in well growing SMCs. However, when the cells are damaged, the expression of SM α-actin will be poor [14]. Also, the α-actin filaments are typically disarranged in damaged SMCs. In this study, immunofluorescence microscopy images of SMCs treated with control PEO, PAT-PEO, and no films (control wells) were obtained (data not shown). The cells in the control well showed a stronger SM α-actin expression (intense staining) with the α-actin filaments oriented along the cell axis. This suggested the healthy state of SMCs in control wells. However, the SM α-actin expression was weaker (less intense staining) for all control PEO films. Also, the cells showed a disarrangement of actin filaments with an irregular orientation. This result showed the inhibitory effect of control PEO films on SMC growth. For PAT-PEO films, very few cells showed the expression of SM α-actin. Also, the expression was very weak with α-actin filaments disarranged in circumferential orientation. This result strongly suggested that PAT-PEO films effectively inhibited the growth of SMCs. The expression of SM α-actin in the cells treated with control PEO films and PAT-PEO films was decreased by half when compared to that of controls (data not shown). No significant difference in the SM α-actin was observed between the different groups of control PEO films or PAT-PEO films. However, the expression observed for all PAT-PEO films was significantly lesser than that of PEO-10 and PEO-15. Also, expression for PAT-PEO-25 was significantly lesser than that of PEO-20 and PEO-25 as well. These results are in agreement with the literature as PAT has been shown to significantly decrease the expression of SM α-actin [26, 27].

PAT-PEO Coatings on Balloons

FIGS. 17 A-C and D-F show the SEM images of bare balloons (without any coatings) in inflated and deflated positions, respectively. These images show that the balloons were fully expanded in its inflated position and were showing flaps in its deflated position. FIGS. 17 G-I, J-L, and M-O shows the SEM images of PAT-PEO coated balloons in as-coated, deflated, and inflated positions, respectively. These images showed that the PAT-PEO coating was smooth, uniform, and homogeneous on the balloon surface (FIG. 17 G-I). Also, the integrity of PAT-PEO coating on the balloons was well maintained without any mechanical defects occurring during inflation or deflation (FIG. 17 J-O). The thickness (200 μm-500 μm) of the PAT-PEO films increases as the w/v % (10% to 25%) of the polymer increases Currently Available Drug-excipient Combination Coatings on Balloons FIGS. 18 A-E, F-J, and K-O show the SEM images of control DCBs prepared using currently available drug-excipient combinations in as-coated, inflated, and deflated positions, respectively. These images showed that these coatings are not smooth, nonuniform, and inhomogeneous at several different spots on the balloon (FIG. 18 A-E). Also, these coatings undergo mechanical defects during balloon inflation or deflation to produce irregularities, ridges, cracks, fissures, and rough textures (FIG. 18 F-O).

Drug Release from PAT-PEO Coating on Balloon

For treatments using DCBs, the typical balloon tracking time is from 30 sec to 1 min. Once the balloon reaches the diseased site, a time frame of 2 min to 3 min is recommended for the treatment including balloon inflation and drug delivery [18]. Hence, in this study, the initial 1 min time is considered as the typical time period for balloon tracking, and the following 3 mins (from 1 min to 4 min) as the typical time period for treatment including inflation and drug delivery. The total amount of PAT loaded on the PAT-PEO coated balloons is $2.23\pm0.31$ μg/mm$^2$. The currently available DCBs carry drug doses in the range of 2 μg/mm$^2$ to 3 μg/mm$^2$ [18]. Hence, the total amount of PAT loaded on the balloons using the PEO platform is clinically relevant for controlling neointimal hyperplasia. The cumulative amount and percentage of PAT release from PAT-PEO coatings are provided in FIGS. 19A and 19A, respectively. Only 15% of the total PAT loaded was released from the balloons during the initial 1 min (typical balloon tracking time) whereas 80% of the drug was released during 1 min to 4 min (typical treatment time period) and only 5% of the drug was present on the balloons after 4 min as a residual drug.

Drug Release from Currently Available Drug-excipient Combination Coatings on Balloons The total amount of PAT loaded on the balloons using currently available drug-excipient combination coatings such as PAT only, PAT-urea, PAT-polysorbate/sorbitol, PAT-shellac, and PAT-contrast agent is $0.17\pm0.11$, $0.11\pm0.03$, $0.03\pm0.01$, $0.09\pm0.02$, and $0.05\pm0.4$ μg/mm$^2$, respectively. The cumulative release and percentage of PAT release from these coatings are provided in FIG. 19B-F and FIG. 20B-F, respectively. PAT only control showed that only 26% of the total PAT loaded was released between 1 min and 4 min while 13% of the drug was released during the initial 1 min and 61% of the drug was retained on the balloon after 4 min. For PAT-urea, only 15% of the total drug loaded was released between 1 min and 4 min while 13% was released during the initial 1 min and 72% was retained on the balloon after 4 min. For PAT-polysorbate/sorbitol, only 7% of the total drug loaded was released between 1 min and 4 min while 36% was released during the initial 1 min and 58% was retained on the balloon after 4 min. For PAT-shellac, only 18% of the total drug loaded was released between 1 min and 4 min while 40% was released during the initial 1 min and 42% was retained on the balloon after 4 min. For PAT-contrast agent, only 24% of the total drug loaded was released between 1 min and 4 min while 32% was released during the initial 1 min and 43% was retained on the balloon after 4 min.

Discussion

This study explores the use of polyethylene oxide (PEO) films for applications in DCBs. PEO used for drug delivery is either uncrosslinked or crosslinked depending on the applications. The pure uncrosslinked PEO is typically used in pharmaceutical products such as oral tablets, bioadhesives, and osmotic pump tablets, while the crosslinked PEO networks are used for applications in implants and medical devices. The reason that pure uncrosslinked PEO is not commonly used in implants and medical devices is that the polymer dissolves very quickly in water-based solutions. Therefore, it is not possible to use this system for delivering drugs for an extended period of time, which is the norm in most drug-eluting medical devices. It is this quick dissolution property that makes the uncrosslinked PEO a promising material for applications in DCBs. Furthermore, the physiochemical properties of PEO can be adjusted easily by varying the w/v % of polymer to tailor the drug release at any specific time intervals between 1 to 7 mins, which is the time frame required for interventionalists to carry out any basic or advanced clinical procedures involving angioplasty as well as balloon-based drug delivery. In this study, as evident from the SEM cross-sectional imaging, the thickness (200 μm-500 μm) of the PAT-PEO films increases as the w/v % (10% to 25%) of the polymer increases. The thicker the film, the longer the time it takes to dissolve and slowly deliver the drug. This has led to the delayed release of various PAT-PEO formulations prepared in this study.

The PAT-PEO coated balloons and five control DCBs were prepared using the same dip coating procedure and by keeping the same concentration of PAT in the coating solutions. SEM images showed that the PAT-PEO coating on the balloon was homogeneous and the coating integrity was well maintained without any mechanical defects occurring during balloon inflation or deflation. However, the coatings on the control DCBs were non-homogenous and several different types of mechanical defects were observed when the balloons were inflated or deflated. This shows the use of PEO as a mechanically robust coating for the balloons. The amount of PAT loaded on PAT-PEO coated balloons was 13 times, 20 times, 74 times, 24 times, and 45 times greater than the amount of PAT loaded on PAT-only, PAT-urea, PAT-polysorbate/sorbitol, PAT-shellac, and PAT-contrast agent control DBCs, respectively. This signifies the use of a polymer carrier such as PEO in carrying an adequate amount of drug on the balloons. If a different coating procedure such as spray coating is employed, it is possible to load more amount of PAT on the control DCBs. However, the accumulation of more PAT directly on a material surface without a polymer-based drug carrier could lead to the formation of loosely bound PAT crystals to provide a burst release. In this study, 80% of the PAT loaded on the PAT-PEO coated balloons was released between 1 min and 4 min (the typical time period of balloon inflation and treatment). For the same time period, the % of PAT released from PAT-only, PAT-urea, PAT-polysorbate/sorbitol, PAT-shellac, and PAT-contrast agent control DBCs were 26%, 15%, 7%, 18%, and 24%, respectively. This further demonstrates the role of PEO in controlling the delivery of drug from the balloons. Also, the PEO platform can potentially be used to deliver other PAT-excipient combinations that are currently used in DCBs.

Conclusions

Various PAT-PEO films were developed in this study for applications in DCBs with a motivation to reduce or prevent initial drug loss during balloon tracking and then to immediately deliver most of the drug within a very short time period of balloon inflation and treatment. The w/v % of PEO and wt % of PAT were varied in PAT-PEO films to tailor the drug release in such a way that >90% of drug was released only at specific time intervals. The SEM and FTIR collectively showed that the PAT-PEO films developed were homogeneous and the PAT was molecularly dispersed in the PEO matrix. DSC showed that the crystallinity of PEO was not affected after the incorporation of PAT. The PAT-PEO films developed were flexible and ductile with no effect observed on the yield or tensile strengths of the films after drug incorporation. The FTIR, DSC, and phase contrast microscopy characterizations of PAT-PEO films post drug-elution study showed the dissolution of PEO under physiological conditions as the primary mechanism for the delivery of PAT. The cell culture studies showed that both the control PEO and PAT-PEO films successfully inhibited the growth of SMCs with a superior inhibitory effect observed for PAT-PEO films. The PAT-PEO coating produced on the balloons was homogeneous and the integrity of coating was well maintained without mechanical defects occurring during balloon inflation and deflation. The drug release studies showed that only 15% of the total PAT loaded was released from the balloons during the typical balloon tracking time period (initial 1 min) while 80% of the PAT was released during the typical balloon treatment time period (from 1 min to 4 min), with only 5% of the PAT present on the balloon as a residual drug after 4 min. Thus, this study demonstrated the use of PEO as an alternate drug delivery platform for balloons.

Discussion

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

REFERENCES

1. Thukkani A K, Kinlay S. Endovascular Intervention for Peripheral Artery Disease. Circulation Research 2015; 116:1599-1613.
2. Waksman R, Pakala R. Drug-eluting balloon: the comeback kid? Circ Cardiovasc Interv 2009; 2:352-8.
3. De Labriolle A, Pakala R, Bonello L, Lemesle G, Scheinowitz M, Waksman R. Paclitaxeleluting balloon: from bench to bed. Catheter Cardiovasc Interv 2009; 73:643-52.
4. Byrne R A, Joner M, Alfonso F, Kastrati A. Drug-coated balloon therapy in coronary and peripheral artery disease. Nat Rev Cardiol 2014; 11:13-23.
5. Pastormerlo L E, Ciardetti M, Trianni G, Ravani M, Shlueter M, Vaghetti M, Coceani M, Rizza A, Berti S, Palmieri C. Drug Eluting Balloon: A Multipurpose Tool for Coronary Revascularization With Optimal Long-Term Follow-Up Results. Journal of Interventional Cardiology 2014; 27:574-579.
6. Lancaster S, Kakade S, Mani G. Microrough cobalt-chromium alloy surfaces for paclitaxel delivery: preparation, characterization, and in vitro drug release studies. Langmuir 2012; 28:11511-11526.
7. Lamichhane S, Gallo A, Mani G. A polymer-free paclitaxel eluting coronary stent: effects of solvents, drug concentrations and coating methods. Ann Biomed Eng 2014; 42:1170-84.
8. Lamichhane S, Lancaster S, Thiruppathi E, Mani G. Interaction of endothelial and smooth muscle cells with cobalt-chromium alloy surfaces coated with paclitaxel deposited selfassembled monolayers. Langmuir 2013; 29:14254-14264.
9. Kakade S, Mani G. A comparative study of the effects of vitamin C, sirolimus, and paclitaxel on the growth of endothelial and smooth muscle cells for cardiovascular medical device applications. Drug Des Devel Ther 2013; 7:529-544.
10. Cakic M, Nikolic G, Ilic L, Stankovic S. Synthesis and FTIR characterization of some dextran sulphates. Chemical Industry and Chemical Engineering Quarterly 2005; 11:74-78.
11. Nikolic G S, Cakic M, Mitic Z, Ilic L. Deconvoluted Fourier-transform LNT-IR study of coordination copper (II) compounds with dextran derivatives. Russian Journal of Coordination Chemistry 2008; 34:322-328.
12. Huang P, Dong A, Caughey W S. Effects of dimethyl sulfoxide, glycerol, and ethylene glycol on secondary structures of cytochrome c and lysozyme as observed by infrared spectroscopy. J Pharm Sci 1995; 84:387-392.
13. Gallo, A., & Mani, G. (2013). A stent for co-delivering paclitaxel and nitric oxide from abluminal and luminal surfaces: Preparation, surface characterization, and in vitro drug release studies. Applied Surface Science, 279, 216-232.
14. de Raucourt E, Mauray S, Chaubet F, Magia-Revel O, Jozefowicz M, Fischer AM. Anticoagulant activity of dextran derivatives. J Biomed Mater Res 1998; 41:49-57.
15. Thiruppathi E, Mani G. Vitamin-C Delivery from CoCr Alloy Surfaces Using Polymer-Free and Polymer-Based Platforms For Cardiovascular Stent Applications. Langmuir 2014; 30:6237-6249.
16. Stoebner, S. E., & Mani, G. (2012). Effect of processing methods on drug release profiles of anti-restenotic self-assembled monolayers. Applied Surface Science, 258(12), 5061-5072.
17. Chenier P J. Survey of Industrial Chemistry. Plastics. Newyork: Plenum Publishing Corporation; 2002.
18. Baba M, Pauwels R, Balzarini J, Arnout J, Desmyter J. Mechanism of inhibitory effect of dextran sulfate and heparin on replication of human immunodeficiency virus in vitro. Proc. Natl. Acad. Sci. USA 1988; 85:6132-6136.
19. Scheller B, Speck U, Abramjuk C, Bernhardt U, Bohm M, Nickenig G. Paclitaxel balloon coating, a novel method for prevention and therapy of restenosis. Circulation 2004; 110:810-814.
20. Mori T, Kinoshita Y, Watanabe A, Yamaguchi T, Hosokawa K, Honjo H. Retention of paclitaxel in cancer cells for 1 week in vivo and in vitro. Cancer Chemotherapy and Pharmacology 2006; 58:665-672.
21. Granada J F, Stenoien M, Buszman P P, Tellez A, Langanki D, Kaluza G L, Leon M B, Gray W, Jaff M R, Schwartz RS. Mechanisms of tissue uptake and retention of paclitaxel-coated balloons: impact on neointimal proliferation and healing. Open Heart 2014; 1:e000117.
22. Mani, G.; Macias, C. E.; Feldman, M. D.; Marton, D.; Oh, S.; Agrawal, C. M., Delivery of paclitaxel from cobalt-chromium alloy surfaces without polymeric carriers. Biomaterials 2010, 31 (20), 5372-5384.
23. Lamichhane, S.; Lancaster, S.; Thiruppathi, E.; Mani, G., Interaction of endothelial and smooth muscle cells with cobalt-chromium alloy surfaces coated with paclitaxel deposited self-assembled monolayers. Langmuir 2013, 29 (46), 14254-14264.

Example 3

Multi-use Balloons

Experimental Details

We incorporated nanoparticle albumin bound paclitaxel (abbreviated as nab-PAT, commercially available under the name "Abraxane®") into polyethylene oxide (PEO), and coated this formulation on the balloon. A 10 w/v % of PEO (0.5 g of PEO in 5 mL di-$H_2O$) was allowed to stir for 6 hours at 400 rpm stirring speed. Then, 225 mg of Abraxane® (containing 202.5 mg albumin and 22.5 mg paclitaxel (PAT)) was added to the PEO solution at 4.5 wt % and allowed to stir for an additional 18 hrs. In parallel, a balloon (4 mm×30 mm) was initially inflated with an air pressure of 6-8 atmospheres. Then, the inflated balloon was dipped in the prepared Abraxane®-PEO solution (PAT concentration—4.5 mg/mL) for 1 minute followed by transferring it into an oven and heat treated in air at 50° C. for 1 hour. The balloon was then taken out and dipped again in Abraxane®-PEO solution for 15 seconds followed by heat treatment in air at 50° C. for 1 hour. This step was again repeated twice.

The Abraxane®-PEO coated balloon was deflated prior to the drug-elution study experiments. The deflated Abraxane®-PEO coated balloon was immersed in 250 mL of PBS/Tween-20 solution and incubated in a circulating water bath at 37° C. The balloon was removed from the solution and transferred to a fresh PBS/Tween-20 solution at predetermined time points (1 minute, 4 minutes, 4.5 minutes, 7.5 minutes, 8 minutes, and 11 minutes). After the 1 minute time point, the balloon was inflated with an air pressure of 6-8 atmospheres and remained inflated between the 1 minute to 4 minute, 4.5 minute to 7.5 minute, and 8 minute to 11 minute time periods. Also, the balloon was deflated throughout the 4 minute to 4.5 minute and 7.5 minute to 8 minute time periods. After 11 minutes, the balloon was taken out and sonicated in a 50 mL of solution containing di-$H_2O$ and ethanol (50:50, v/v) for 1 minute to remove any residual drug present on the balloon. All solutions collected were analyzed for the amount of PAT released using High performance liquid chromatography (HPLC).

Results

The total drug loaded onto the balloon was 988 which was 2.6 µg/$mm^2$. Percentage of drug release at different time points are shown in Table 6.

TABLE 6

| Up to 1 minute | 1 minute to 4 minutes | 4 minutes to 4.5 minutes | 4.5 minutes to 7.5 minutes | 7.5 minutes to 8 minutes | 8 minutes to 11 minutes | Residual drug on the balloon after 11 minutes |
|---|---|---|---|---|---|---|
| 5% | 16% | 4% | 11% | 3% | 51% | 9% |

Up to 1 min = typical balloon tracking time period
1 minute to 4 minutes = typical balloon inflation and treatment time period at location # 1
4 minutes to 4.5 minutes = typical balloon tracking time period to move from location # 1 to location # 2
4.5 minutes to 7.5 minutes = typical balloon inflation and treatment time period at location # 2
7.5 minutes to 8 minutes = typical balloon tracking time period to move from location # 2 to location # 3
8 minutes to 11 minutes = typical balloon inflation and treatment time period at location # 3
After 11 minutes = residual drug present on the balloon surface after 11 mins.

Discussion

Only 5% of the drug was lost during the typical balloon tracking period (1 minute). Then, 16% of the drug (163 µg or 0.4 µg/$mm^2$) was released during the three minute inflation treatment period (1 minute to 4 minutes). After that, 11% of the drug (110 µg or 0.3 µg/$mm^2$) was released during the 4.5 minute to 7.5 minute time period. Then, 51% of the drug (503 µg or 1.3 µg/$mm^2$) was released during the 8 minute to 11 minute time period. Therefore, only 9% of the drug was retained on the balloon after 11 minutes. Hence, these results demonstrate feasibility for a multi-use balloon using Abraxane®-PEO coating for potentially treating three different arterial sections using the same single balloon. Thus, these results demonstrated the development of a multi-use balloon using Abraxane®-PEO as a coating.

We claim:

1. A medical device comprising a formulation disposed on a surface of the medical device, wherein the formulation comprises:
   about 10% to about 25% w/v of poly(ethylene oxide) (PEO) polymer, wherein the PEO has an average molecular weight between about 100,000 Da and about 200,000 Da;
   a therapeutic disposed within the formulation; and
   an inert polymer layer disposed atop the formulation.

2. The medical device of claim 1, wherein the formulation comprises an array of the formulation on the surface of the medical device, wherein the array comprises:
   one or more positions comprising a first formulation position; and
   one or more positions comprising a second formulation position, wherein the second formulation position comprises PEO having a higher % w/v than the first formulation position.

3. The medical device of claim 2, wherein the array further comprises one or more positions comprising a third formulation position, wherein third formulation position comprises PEO having a higher % w/v than the second formulation position.

4. The medical device of claim 1, wherein the formulation has a thickness between about 25 μm and about 100 μm.

5. The medical device of claim 1, wherein the medical device is selected from the group consisting of: balloon catheters, drug-eluting stents, vascular grafts, heart valves, pacemakers, artificial heart, ventricular assist devices, cardiopulmonary bypass, orthopedic devices, fracture fixation devices, dental devices, neural devices, stent grafts, heart-lung machines, hemodialysis machines, ocular implants and devices, and cochlear implants and devices.

6. The medical device of claim 5, wherein the medical device comprises a balloon portion of a balloon catheter.

7. The medical device of claim 1, wherein the therapeutic comprises paclitaxel and/or paclitaxel albumin bound particles.

8. The medical device of claim 4, wherein the medical device comprises a balloon portion of a balloon catheter.

9. The medical device of claim 8, wherein the formulation comprises an array of the formulation on the surface of the balloon portion of the balloon catheter, wherein the array comprises:

one or more positions comprising a first formulation position; and one or more positions comprising a second formulation position, wherein the second formulation position comprises PEO having a higher % w/v than the first formulation position.

10. The medical device of claim 8, wherein the therapeutic comprises paclitaxel and/or paclitaxel albumin bound particles.

11. The medical device of claim 9, wherein the therapeutic comprises paclitaxel and/or paclitaxel albumin bound particles.

12. The medical device of claim 1, wherein the formulation comprises about 10% to about 20% w/v of PEO polymer, wherein the PEO has an average molecular weight of between about 100,000 Da and about 200,000 Da.

13. The medical device of claim 1, wherein the formulation comprises about 10% to about 25% w/v of PEO polymer, wherein the PEO has an average molecular weight about 100,000 Da.

14. The medical device of claim 1, wherein the formulation comprises about 10% to about 20% w/v of PEO polymer, wherein the PEO has an average molecular weight of about 200,000 Da.

* * * * *